United States Patent [19]

Oshiro et al.

[11] Patent Number: 4,788,130
[45] Date of Patent: Nov. 29, 1988

[54] 1-AMINO-2,3-DIHYDRO-1H-INDENE COMPOUNDS

[75] Inventors: Yasuo Oshiro; Hiraki Ueda; Kazuyuki Nakagawa, all of Tokushima, Japan

[73] Assignee: Otsuka Pharmaceutical Co., Ltd., Tokyo, Japan

[21] Appl. No.: 770,677

[22] Filed: Aug. 29, 1985

[30] Foreign Application Priority Data

Aug. 31, 1984 [JP] Japan ................. 59-183514

[51] Int. Cl.$^4$ ................. A61K 31/135; A61K 31/495; C07D 131/02; C07D 295/14
[52] U.S. Cl. ................. 514/661; 514/317; 514/346; 514/629; 514/640; 546/206; 546/337; 564/180; 564/244; 564/253; 564/259; 564/265; 564/268; 564/270; 564/305; 564/428
[58] Field of Search ................. 546/206, 337; 564/253, 564/259, 265, 268, 270, 305, 428, 180, 244; 514/317, 346, 640, 629, 661,

[56] References Cited

U.S. PATENT DOCUMENTS

| | | | |
|---|---|---|---|
| 2,916,490 | 12/1959 | Schenck et al. | 564/428 |
| 3,637,740 | 1/1972 | Sayes | 564/428 |
| 3,655,561 | 4/1972 | Schick et al. | 564/428 |
| 4,134,997 | 1/1979 | Cannon et al. | 564/428 |

FOREIGN PATENT DOCUMENTS

| | | | |
|---|---|---|---|
| 76669 | 4/1983 | European Pat. Off. . | |
| 199862 | 9/1985 | Japan | 564/428 |
| 1187017 | 7/1967 | United Kingdom | 564/428 |
| 1164596 | 9/1969 | United Kingdom . | |
| 2135999 | 9/1984 | United Kingdom | 564/428 |

OTHER PUBLICATIONS

Aspro-Nicholas Ltd. Fine Chemicals Patents Journal 6, No. 34, French 4230M.
Aspro-Nicholas, Ltd. Fine Chemicals Patents Journal 6, No. 11.
Merchant et al. CA 88-74225r.
Bochis et al., CA 84-121829v.
Deana et al. CA 98-125575W.
Oka et al., CA 96-104758b.
Deana et al., J. Med Chem. 1983, 26, 580-585.
Oshiro et al., Chemical Abst. 104-68632d.
Takatori et al., Bulletin of the Chemical Society of Japan vol. 48(11), 3411-3412(1975).

Primary Examiner—Donald G. Daus
Assistant Examiner—Cecilia Shen
Attorney, Agent, or Firm—Finnegan, Henderson, Farabow, Garrett & Dunner

[57] ABSTRACT

Novel 2,3-dihydro-1H-indene derivatives and salts thereof represented by the general formula (1),

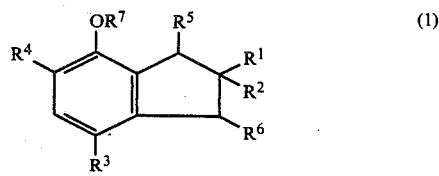

[wherein $R^1$ and $R^2$ are each a hydrogen atom, a lower alkyl group, a phenyl group which may have halogen atoms and/or alkyl groups as the substituents on the phenyl ring; $R^3$ is a halogen atom or a lower alkyl group; $R^4$ is a hydrogen atom, a halogen atom, a phenyl-lower alkyl group, a cycloalkyl-lower alkyl group or the like; $R^5$ is a hydroxyimino group, an alkylamino group or a group of the formula —$NHR^8$ (wherein $R^8$ is a hydrogen atom, a halogen-substituted lower alkanoyl group or the like); $R^6$ is a hydrogen atom or a phenyl group; and $R^7$ is a hydrogen atom or a lower alkyl group].

The 2,3-dihydro-1H-indene derivatives and salt thereof are useful as improving agents for treating anoxemic and hypoxic symptoms and syndromes accompanied therewith, cerebral activators, amnesia curative agents, presbyophrenia curative agents, treating agents for breathing arrest and improving agents for hypoxia accompanied with potassium cyanide poisoning, as well as useful as anti-inflammatory agents and hypotensive agents.

14 Claims, No Drawings

1-AMINO-2,3-DIHYDRO-1H-INDENE COMPOUNDS

FIELD OF THE INVENTION

The present invention relates to novel 2,3-dihydro-1H-indene derivatives and salts thereof having excellent activities for improving anoxemic and hypoxic symptoms and syndromes accompanied therewith, as well as having excellent anti-inflammatory, hypotensive, gastric juice secretion inhibitory actions, and further having excellent immunosupressive actions.

Thus, the novel 2,3-dihydro-1H-indene derivatives and salts thereof are useful as improving agents for treating anoxemic and hypoxic symptoms and syndromes accompanied therewith, cerebral activators, amnesia curative agents, presbyophrenia curative agents, treating agents for breathing arrest and improving agents for hypoxia accompanied with potassium cyanide poisoning, as well as they are useful as prophylactics for arrhythmia and heart failure caused by hypoxia, as well as they are useful as anti-inflammatory agents, hypotensive agents.

PRIOR ART AND PROBLEMS INVOLVED

Oxygen is one of the essential elements to the living body for sustaining the life through release of energies and metabolisms. In the living body, oxygen is converted into so-called "active oxygen radicals", for example, oxygen anion radicals, peroxide ion, hydroxy radical, etc. in various biochemical reactions, such as energy releasing reactions, enzymatic reactions, and other reactions causdd by exposures in ultraviolet rays and various radiations.

The active oxygen radicals are indeed useful for the actions of oxygenase and phagocytosis carried out by leucocytes. On the other hand, the active oxygen radicals promote peroxidation reaction of unsaturated fatty acids, such as oleic acid, linoleic acid, linolenic acid and arachidonic acid, etc. These unsaturated fatty acid and existing abundantly in the living body, and are the main constituents of the biomembranes. The peroxidation reaction of the unsaturated fatty acids produce peroxidized substances such as peroxidized lipids. Similar to the active oxygen radicals, said peroxidized substances also produce alkoxy radicals and hydroxy radicals which will attack the biomembranes and will result disorder of the biomembranes and deactivation of various useful enzymes working in the living body. Cf. "TAISHA" (Metabolisms), Vol. 15, No. 10, (1978), Special issue of active oxygen.

On the other hand, there are existing some other enzymes, such as superoxide dismutase (hereinafter referred to as "SOD"), catalase, glutathion peroxidase, etc. in the living body. These enzymes prevent the deactivation of metabolism from the attack of the active oxygen radicals. Additionally, there are existing several vitamins, such as tocopherols (vitamin E groups) having antioxidative activities in the living body.

Generally, the normal homeostasis of the living body is sustained by the actions of these enzymes and vitamins having antioxidative activities. However, sometimes the phylaxis mechanisms of the living body being suitably maintained by the actions of these enzymes and vitamins may be defected by certain reasons, and the formation of the active oxygen radicals in an amount exceeds to the ability of the phylaxis mechanism of the living body, as well as the formation and accumulation of the peroxidized substances are observed. In such cases that the phylaxis mechanism of the living body is defected, then several severe disorders such as various diseases caused by the aggregation of the platelets, inflammations, disorder of the liver, arteriosclerosis, hemolysis, senescene or presbyopherenia, retinosis, disorder of the lungs, disorders of the heart and the lungs caused by the actions of certain drugs, ischemic coronary heart disease and the like will be occurred accompanied with the progressive chain reactions of the peroxidation.

Hitherto, compounds having actions for scavenging the active oxygen radicals which are considered to be the main factors of the above-mentioned various diseases, and for preventing or lowering the formation and accumulation of the peroxidized substances in the living body were known and called as antioxidants. A number of studies on prophylaxis and curative effects by using these antioxidants have been reported in related literatures. As to enzymatic preparations containing SOD and other enzymes as mentioned previously are reported in "SUPEROXIDE TO IGAKU" (Superoxides and Medicine) by Yoshihiko Ohyanagi, pp. 137–141, (1981), published from Kyoritsu Publishing Co., Ltd. Further, as to other antioxidants, such as butylhydroxytoluene (BHT), butylhydroxyanisol (BHA), tocopherol (vitamin E) and others are reported in "IYAKU JOURNAL" (Pharmaceutical Journal), Vol. 19, No. 12, pp. 2351-2359 (1983) by Makoto Mino, and Hidetaka Tanaka; Ibid., Vol. 19, No. 5, pp. 909-914 (1983), by Toshihiko Suematus.

Some indane compounds having chemical structural formula similar to that of 2,3-dihydro-1H-indene derivative according to the present invention are known in prior art literatures, for example, U.S. Pat. No. 2,916,490 (M. Schenck, et al.), U.S. Pat. No. 3,637,740 (R. Sarges), Japanese Patent Pre-examination Application (Kokai) No. 245875 (1983) and J. Med. Chem., (1983), 26, pp. 580-585 (by A. A. Deana, et al.).

BRIEF SUMMARY OF THE INVENTION

The novel 2,3-dihydro-1H-indene derivatives and salts thereof of the present invention have excellent activities for scavenging the active oxygen radicals and for preventing or lowering the formation of the peroxidized lipids in the living body. Therefore, the 2,3-dihydro-1H-indene derivatives and salts thereof of the present invention are useful as preventive and curative agents for various diseases and disorders caused by excessive formation and accumulation of the active oxygen radicals, peroxidized substances such as peroxidized lipids in the living body, and/or the defects of prophylaxis mechanism of the living body, for example anti-arteriosclerotic agents, anti-inflammatory agents, analgesics, autoimmune disease curative agents, platelets aggregation inhibitory agents, hypotensive agents, anti-hyperlipemic agents, retinosis of immature infant and cataract preventive and curative agents. Furthermore, the 2,3-dihydro-1H-indene derivatives and salts thereof of the present invention are useful as improving and curative agents for disturbances of consciousness caused by cerebrovascular disorder (for example, cerebral hemorrhage, cerebral infarction, subarachnoidal hemorrhage and hypertensive encephalopathy), encephalitides, brain tumor, head injury, psychosis, metabolic disturbance, drug intoxication and disturbances caused by physical reasons, as well as are useful as treating and/or improving agents for sequelae caused by diseases, syndromes and symptoms, furthermore, aprosexia, hyperkinetic syndrome, speech disturbance and mental development retardation.

The 2,3-dihydro-1H-indene derivatives and salts thereof are also useful as antioxidants for oils and fats being contained in processed foods.

The 2,3-dihydro-1H-indene derivatives and salts thereof of the present invention are characterized as low toxicity with less side-effects.

An object of the present invention is to provide novel 2,3-dihydro-1H-indene derivatives and salts thereof represented by the general formula (1) mentioned below, having excellent pharmacological activities as mentioned above.

Another object of the present invention is to provide processes for preparing novel 2,3-dihydro-1H-indene derivatives and salts thereof represented by the general formula (1).

Further object of the present invention is to provide a pharmaceutical composition containing 2,3-dihydro-1H-indene derivative or salt thereof represented by the general formula (1) as the active ingredient.

DETAILED DESCRIPTION OF THE INVENTION 2,3-Dihydro-1H-indene derivatives and salts thereof of the present invention are novel compounds which have not been known in related literatures up to the date, and are represented by the general formula (1) as follows:

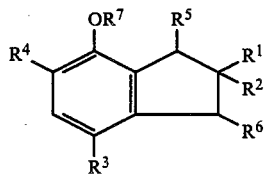

wherein $R^1$ and $R^2$ are each a hydrogen atom, a lower alkyl group, an unsubstituted phenyl group, a substituted phenyl group having at least one substituent selected from the group consisting of a halogen atom and a lower alkyl group on the phenyl ring, an unsubstituted cycloalkyl group, a substituted cycloalkyl group having at least one halogen atom as the substituent on the cycloalkyl ring, a cycloalkyl-lower alkyl group, a hydroxy group, a phenyl-lower alkoxy group, an unsubstituted phenyl-lower alkyl group or a substituted phenyl-lower alkyl group having at least one substituent selected from the group consisting of a halogen atom, a lower alkylenedioxy group and a lower alkoxy group on the phenyl ring;

$R^3$ is a halogen atom or a lower alkyl group;

$R^4$ is a hydrogen atom, a halogen atom, a phenyl-lower alkyl group, a cycloalkyl-lower alkyl group, a piperidinyl-lower alkanoylamino-lower alkyl group, a pyridinium-lower alkanoylamino-lower alkyl group or a lower alkyl group;

$R^5$ is a hydroxyimino group, an alkylamino group having 7 to 10 carbon atoms or a group of the formula —$NHR^8$ ((wherein $R^8$ is a hydrogen atom, a halogen-substituted lower alkanoyl group, a lower alkylamino-lower alkyl group, a phenyl-lower alkyl group or a group of the formula —A—B (wherein A is a lower alkylene group which may have at least one hydroxy group as the substituent, a group of the formula —CO—(D)$_l$— or —D—CO—, wherein D is a lower alkylene group, l is an integer of 0 or 1; B is a 5- or 6-membered saturated or unsaturated heterocyclic group which may have at least one substituent selected from the group consisting of a lower alkyl group which may have at least one hydroxy group as the substituent, an oxo group, a carboxy group, a lower alkoxycarbonyl group, a pyridyl group, a phthalimido group, a pyrrolidinylcarbonyl-lower alkyl group, an unsubstituted phenyl group, a substituted phenyl group having 1 to 3 substituents selected from the group consisting of a halogen atom, a lower alkyl group which may have at least one halogen atom as the substituent, a lower alkoxy group and a nitro group on the phenyl ring, a phenyl-lower alkyl group and a benzoyl group which may have at least one lower alkoxy group as the substituent on the phenyl ring)));

$R^6$ is a hydrogen atom or a phenyl group;

$R^7$ is a hydrogen atom or a lower alkyl group;

provided that, when $R^5$ is a hydroxyimino group, $R^6$ and $R^7$ are each a hydrogen atom, or when R is a group of the formula —$NHR^8$ (wherein $R^8$ is a hydrogen atom or a halogen-substitute lower alkanoyl group) and further $R^1$ and $R^2$ are each a hydrogen atom or a lower alkyl group, then $R^4$ should be neither a hydrogen atom, a lower alkyl group, a halogen atom, a nitro group, an amino group nor a lower alkanoylamino group.

In the present specification, the symbols of $R^1$, $R^2$, $R^3$, $R^4$, $R^5$, $R^6$ and $R^7$ are more specifically exemplified as follows.

As to the lower alkyl group, a straight chain-or branched chain alkyl group having 1 to 6 carbon atoms, such as methyl, ethyl, propyl, isopropyl, butyl, tert-butyl, pentyl, hexyl, 1-methylpropyl, 2-methylpropyl, 1,1-dimethylpropyl, 1-methylbutyl, 2-methylbutyl, 3-methylbutyl, 2,2-dimethylpropyl, 2,3-dimethylpropyl, 1-methylpentyl, 1,1-dimethylbutyl and 1-ethylbutyl groups can be exemplified.

As to the halogen atom, fluorine atom, chlorine atom, bromine atom and iodine atom can be exemplified.

As to the phenyl-lower alkyl group, a phenylalkyl group in which the alkyl moiety is a straight chain- or branched chain-alkyl group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups can be exemplified.

As to the cycloalkyl-lower alkyl group, a cycloalkylalkyl group having 3 to 8 carbon atoms in which the alkyl moietyl is a straight chain- or branched chain-alkyl group having 1 to 6 carbon atoms, such as cyclopropylmethyl, cyclobutylmethyl, cyclopentylmethyl, cyclohexylmethyl, cycloheptylmethyl, cyclooctylmethyl, 2-cyclohexylethyl, 1-cyclohexylethyl, 1-cyclohexylpropyl, 3-cyclopentylpropyl, 2-cyclopentylethyl, 4-cyclobutylbutyl, 5-cycloheptylpentyl, 6-cyclooctylhexyl, 1,1-dimethyl-2-cyclopropylethyl and 2-methyl-3-cyclopentylpropyl groups can be exemplified.

As to the halogen-substituted lower alkanoyl group, a straight chain- or branched chain-alkanoyl group having 1 to 6 carbon atoms and having 1 to 3 halogen atoms as the substituents, such as 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5- chloropentanoyl, 3-chloro-2-methylpropionyl, 6-bromohexanoyl and 5,6-dibromohexanoyl groups can be exemplified.

As to the alkylene group which may have at least one hydroxy group as the substituent, a straight chain- or branched chain-alkylene group having 1 to 6 carbon atoms and which may have at least one hydroxy group as the substituent, such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, 1-hydroxymethylene, 1-hydroxyethylene, 2-hydroxytrimethylene, 1-hydroxy-2-methyltrimethylene, 1-hydroxy-2,2-dimethyltrimethylene, 1-methyl-2-hydroxytrimethylene, 2-hydroxytetramethylene, 3-hydroxypentamethylene and 4-hydroxyhexamethylene groups can be exemplified.

As to the lower alkylene group, a straight chain- or branched chain-alkylene group having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups can be exemplified.

As to the 5- or 6-membered saturated or unsaturated heterocyclic ring group, such as piperazinyl, morpholino, thiomorpholino, piperidinyl, pyrrolidinyl, imidazolyl, pyridyl, pyrazolyl, isothiazol, isoxazolyl, pyrazinyl, pyrimidinyl, thienyl, furyl and pyranyl groups can be exemplified.

As to the lower alkoxycarbonyl group, a straight chain- or branched chain-alkoxycarbonyl group having 1 to 6 carbon atoms, such as methoxycarbonyl, ethoxycarbonyl, propoxycarbonyl, isoproxycarbonyl, butoxycarbonyl, tert-butoxycarbonyl, pentyloxycarbonyl and hexyloxycarbonyl groups can be exemplified.

As to the lower alkoxy group, a straight chain- or branched chain-alkoxy group having 1 to 6 carbon atoms, such as methoxy, ethoxy, propoxy, isopropoxy, butoxy, tert-butoxy, pentyloxy and hexyloxy groups can be exemplified.

As to the substituted phenyl group having 1 to 3 substituents selected from the group consisting of a halogen atom, a lower alkyl group which may have halogen atoms as the substituents, a lower alkoxy group and a nitro group on the phenyl ring, a substituted phenyl group having 1 to 3 substituents selected from the group consisting of a halogen atom, a straight chain- or branched chain alkyl group having 1 to 6 carbon atoms and which may have 1 to 3 halogen atoms as the substituents, a straight chain- or branched chain alkoxy group having 1 to 6 carbon atoms and a nitro group on the phenyl ring, such as 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-trifluoromethylphenyl, 3-trichloromethylphenyl, 4-chloromethylphenyl, 2-dibromomethylphenyl, 3-(2,2,2-trifluoroethyl)phenyl, 4-(1,2-dichloroethyl)phenyl, 2-(5-chloropentyl)phenyl, 3-(6-bromohexyl)phenyl, 4-(5,6-dibromohexyl)phenyl, 2-iodomethylphenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 2-methoxyphenyl, 3-methoxyphenyl, 4-methoxyphenyl, 2-ethoxypehnyl, 3-ethoxyphenyl, 4-ethoxyphenyl 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 2-nitrophenyl, 3-nitrophenyl, 4-nitrophenyl, 2,4-dinitrophenyl, 3-methyl-4-chlorophenyl, 2-chloro-6-methylphenyl and 2-methoxy-3-chlorophenyl groups can be exemplified.

As to the 5- or 6-membered saturated or unsaturated heterocyclic ring group which may have, as the substituents, selected from the group consisting of a lower alkyl group which may have hydroxy groups as the substituents, an oxo group, a carboxy group, a lower alkoxycarbonyl group, a pyridyl group, a phthalimido group, a pyrrolidinylcarbonyl-lower alkyl group, a phenyl group which may have 1 to 3 substituents selected from the group consisting of a halogen atom, a lower alkyl group which may have halogen atoms as the substituents, a lower alkoxy group and a nitro group on the phenyl ring, a phenyl-lower alkyl group and a benzoyl group which may have 1 to 3 lower alkoxy groups as the substituents on the phenyl ring, there can be exemplified 5- or 6-membered saturated or unsaturated heterocyclic ring group which may have, as the substituents, selected from the group consisting of a straight chain- or branched chain-alkyl group having 1 to 6 carbon atoms and which may have hydroxy groups as the substituents, an oxo group, a carboxy group, a straight chain- or branched chain-alkoxycarbonyl group having 1 to 6 carbon atoms, a pyridyl group, a phthalimido group, a pyrrolidinylcarbonyl-$C_{1-6}$-alkyl group, a phenyl group which may have 1 to 3 substituents selected from the group consisting of a halogen atom, a straight chain- or branched chain-alkyl group having 1 to 6 carbon atoms and which may have 1 to 3 halogen atoms as the substituents, a straight chain- or branched chain-alkoxy group having 1 to 6 carbon atoms and nitro group, on the phenyl ring, a phenyl-$C_{1-6}$-alkyl group, a benzoyl group which may have 1 to 3 $C_{1-6}$-alkoxy groups as the substituents on the phenyl ring, such as 4-methyl-1-piperazinyl, 4-butyl-1-piperazinyl, 4-ethyl-1-piperazinyl, 4-hexyl-1-piperazinyl, 3-ethyl-1-morpholino, 2-propyl-1-thiomorpholino, 4-methyl-1-piperidinyl, 3-ethyl-1-pyrrolidinyl, 5-methylimidazolyl, 3-methylpyridyl, 4-methylpyridyl, 3-methylpyrazolyl, 5-methylisothiazolyl, 5-ethylisoxazolyl, 3-methyl-2-pyrazinyl, 4-pentyl-2-pyrimidinyl, 5-propylthienyl, 5-methylfuryl, 4-hexylpyranyl, 4-(hydroxymethyl)-1-piperazinyl, 4-(1-hydroxyethyl)-1-piperazinyl, 4-(6-hydroxyphenyl)-1-piperazinyl, 2-(3-hydroxypropyl)-1-thiomorpholino, 3-(2-hydroxyethyl)-1-morpholino, 4-hydroxymethyl)-1-piperidinyl, 3-(2-hydroxyethyl)-1-pyrrolidinyl, 5-(hydroxymethyl)imidazolyl, 3-(hydroxymethyl)pyridyl, 4-(1-hydroxyethyl)pyridyl, 3-(hydroxymethyl)pyrazolyl, 5-(hydroxymethyl)isothiazolyl, 5-(2-hydroxyethyl)isoxazolyl, 3-hydroxymethyl-2-pyrazinyl, 4-(5-hydroxypentyl)-2-pyrimidinyl, 5-(3-hydroxypropyl)thienyl, 5-hydroxymethylfuryl, 4-(6-hydroxyhexyl)pyranyl, 2-oxo-1-pyrrolidinyl, 2-carboxy-1-pyrrolidinyl, 3-carboxy-1-pyrrolidinyl, 4-carboxy-1-pyrrolidinyl, 2-methoxycarbonyl-1-pyrrolidinyl, 2-ethoxycarbonyl-1-pyrrolidinyl, 3-propoxycarbonyl-1-pyrrolidinyl, 4-butoxycarbonyl-1-pyrrolidinyl, 2-hexyloxycarbonyl-1-pyrrolidinyl, 3-pentyloxycarbonyl-1-pyrrolidinyl, 4-(2-pyridyl)-1-piperazinyl, 4-phenyl-1-piperazinyl, 4-(2-chlorophenyl)-1-piperazinyl, 4-(3,5-dichlorophenyl)-1-piperazinyl, 4-(2,3-dichlorophenyl)-1-piperazinyl, 4-(2-methoxyphenyl)-1-piperazinyl, 4-(4-nitrophenyl)-1-piperazinyl, 4-(2,3-dimethylphenyl)-1-piperazinyl, 4-(2,4,5-trimethyl)-1-piperazinyl, 4-(3-methoxyphenyl)-1-piperazinyl, 4-(3- methylphenyl)-1-piperazinyl, 4-(4-bromophenyl)-1-piperazinyl, 4-(3-fluorophenyl)-1-piperazinyl, 4-(2-iodophenyl)- 1-piperazinyl, 4-(2-butoxyphenyl)-1-piperazinyl, 4-(3-pentyloxyphenyl)-1-piperazinyl, 4-(4-hexyloxyphenyl)-1-piperazinyl, 4-(3,4,5-trimethoxyphenyl)-1-piperazinyl, 4-(3-ethylphenyl)-1-piperazinyl, 4-(4-propylphenyl)-1-piperazinyl, 4-(3-pentylphenyl)-1-piperazinyl, 4-(4-hexylphenyl)-1-piperazinyl, 4-(3-butyl-phenyl)-1-piperazinyl, 4-benzyl-1-piperazinyl, 4-(2-phenylethyl)-1-piperazinyl, 4-(3-phenylpropyl)-1-piperazinyl, 4-(4-phenylbutyl)-1-piperazinyl, 4-(1,1-dimethyl-2-phenylethyl)-1-piperazinyl, 4-(5-phenylpentyl)-1-piperazinyl, 4-(6-phenylhexyl)-1-piperazinyl, 4-(2-methyl-3-phenylpropyl)-1-piperazinyl, 4-benzoyl-1-piperazinyl, 4-(2-methoxybenzoyl)-1-piperazinyl, 4-(3-methoxybenzoyl)-1-piprazinyl, 4-(4-methoxybenzoyl)-1-piperazinyl, 4-(2-ethoxybenzoyl)-1-piperazinyl, 4-(4-isopropoxybenzoyl)-1-piperazinyl, 4-(4-hexyloxybenzoyl)-1-piperazinyl, 4-(3,4-dimethoxybenzoyl)-1-piperazinyl, 4-(3,4,5-trimethoxybenzoyl)-1-piperazinyl, 4-(pyrrolidinylcarbonylmethyl)-1-piperazinyl, 4-[2-(pyrrolidinylcarbonyl)ethyl]-1-piperazinyl, 4-[1-(pyrrolidinylcarbonyl)ethyl]-1-piperazinyl, 4-[4-(pyrrolidinylcarbonyl)butyl]-1-piperazinyl, 4-[6-(pyrrolidinylcarbonyl)hexyl]-1-piperazinyl, 4-phthalimido-1-piperazinyl, 4-phthalimido-1-piperidinyl, 4-(2-trifluoromethylphenyl)-piperazinyl, 4-(3-trichloromethylphenyl)-1-piperazinyl, 4-(4-chloromethylphenyl)-1-piperazinyl, 4-[3-(2,2,2-trifluoroethyl)phenyl]-1-piperazinyl, 4-[4-(1,2-dichloroethyl)phenyl]-1-piperazinyl, 4-[2-(5-chloropentyl)phenyl]-1-piperazinyl, -[3-(6-bromohexyl)phenyl]-1-piperazinyl, 4-[4-(5,6-dibromohexyl)phenyl]-1-piperazinyl and 4-(2-iodomethylphenyl)-1-piperazinyl groups.

As to the piperidinyl-lower alkanoylamino-lower alkyl group, a piperidinylalkanoylaminoalkyl group in which the alkanoylamino moiety is a straight chain- or branched chain-alkanoylamino group having 2 to 6 carbon atoms, and the alkyl moiety is a straight chain- or branched chain-alkyl group having 1 to 6 carbon atoms, such as piperidinylacetylaminomethyl, (3-piperidinylpropionyl)aminomethyl, (4-piperidinylbutyryl)aminomethyl, (5-piperidinylpentanoyl)aminomethyl, (6-piperidinylhexanoyl)aminomethyl, 2-(piperidinylacetylamino)ethyl, 1-[(3-piperidinylpropionyl)amino]ethyl, 3-[(4-piperidinylbutyryl)amino]propyl, 4-[(5-piperidinylpentanoyl)amino]butyl, 1,1-dimethyl-2-[(6-piperidinylhexanoyl)amino]ethyl, 5-(piperidinylacetylamino)pentyl, 6-[(3-piperidinylpropionyl)amino]hexyl and 2-methyl-3-(piperidinylacetylamino)propyl groups can be exemplified.

As to the alkylamino group having 7 to 10 carbon atoms, a straight chain- or branched chain-alkylamino group having 7 to 10 carbon atoms, such as heptylamino, octylamino, nonylamino and decylamino groups can be exemplified.

As to the pyridinium-lower alkanoylamino-lower alkyl group, a pyridinium-alkanoylaminoalkyl group in which the alkanoylamino moiety is a straight chain- or branched chain alkanoylamino group having 2 to 6 carbon atoms, and the alkyl moiety is a straight chain- or branched chain-alkyl group having 1 to 6 carbon atoms, such as pyridinium acetylaminomethyl, (3-pyridinium propionyl)aminomethyl, (4-pyridinium butyryl)aminomethyl, (5-pyridinium pentanoyl)aminomethyl, (6-pyridinium hexanoyl)aminomethyl, 2-(pyridinium acetylamino)ethyl, 1-[(3-pyridinium propionyl)amino]ethyl, 3-[(4-pyridinium butyryl)amino]propyl, 4-[(5-pyridinium pentanoyl)amino]-butyl, 1,1-dimethyl-2-[(6-pyridinium hexanoyl)amino]ethyl, 5-(pyridinium acetylamino)pentyl, 6-[(3-pyridinium propionyl)amino]hexyl and 2-methyl-3-(pyridinium acetylamino)propyl groups can be exemplified.

As to the substituted phenyl group having at least one substituent selected from the group consisting of a halogen atom and a lower alkyl group on the phenyl ring, a substituted phenyl group having 1 to 3 substituents selected from the group consisting of a halogen atom and a straight chain- or branched chain-alkyl group having 1 to 6 carbon atoms on the phenyl ring, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 3-methyl-4-chlorophenyl and 2-chloro-6-methylphenyl groups can be exemplified.

As to the unsubstituted cycloalkyl group, a cycloalkyl group having 3 to 8 carbon atoms, such as cyclopropyl, cyclobutyl, cyclopentyl, cyclohexyl, cycloheptyl and cyclooctyl groups can be exemplified.

As to the substituted cycloalkyl group having at least one halogen atom as the substituent on the cycloalkyl ring, a cycloalkyl group having 3 to 8 carbon atoms and having 1 to 3 halogen atoms as the substituent on the cycloalkyl ring, such as 1-chlorocyclopropyl, 1-bromocyclobutyl, 2-chlorocyclobutyl, 1-chlorocyclopentyl, 2-bromocyclopentyl, 1-chlorocyclohexyl, 2-bromocyclohexyl, 3-fluorocyclohexyl, 1-chlorocycloheptyl, 2-bromocycloheptyl, 3-fluorocycloheptyl, 4-iodocycloheptyl, 1-chlorocyclooctyl, 2-bromocyclooctyl, 3-fluorocyclooctyl, 4-iodocyclooctyl, 1,2-dichlorocyclopentyl, 2,3-dibromocyclohexyl, 2,4-dichlorocycloheptyl, 3,4-dibromocyclooctyl, 2,3,4-trichlorocyclohexyl, and 2-bromo-4,4-dichlorocyclohexyl groups can be exemplified.

As to the phenyl-lower alkoxy group, a phenylalkoxy group in which the alkoxy moiety is a straight chain- or branched chain-alkoxy group having 1 to 6 carbon atoms, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy groups can be exemplified.

As to the substituted phenyl-lower alkyl group having at least one substituent selected from the group consisting of a halogen atom, a lower alkoxy group and a lower alkylenedioxy group on the phenyl ring, a substituted phenylalkyl group in which the alkyl moiety is a straight chain- or branched chain-alkyl group having 1 to 6 carbon atoms, and having 1 to 3 substituents selected from the group consisting of a halogen atom and a straight chain- or branched chain-alkoxy group having 1 to 6 carbon atoms on the phenyl ring, and having one straight chain- or branched chain-alkylenedioxy group having 1 to 4 carbon atoms on the phenyl ring, there can be exemplified, such as (2-chlorophenyl)methyl, 2-(3-chlorophenyl)ethyl, 1-(4-chlorophenyl)ethyl, 3-(2-fluorophenyl)propyl, 4-(3-bromophenyl)butyl, 1,1-dimethyl-2-(4-iodophenyl)ethyl, 5-(3,5-dichlorophenyl)pentyl, 6-(3,4-difluorophenyl)hexyl, 2-methyl-3-(3,4,5-trichlorophenyl)propyl, (2,6-dibromophenyl)methyl, (2-methoxyphenyl)methyl, 2-(3-ethoxyphenyl)ethyl, 1-(4-isopropoxyphenyl)ethyl, 3-(4-hexyloxyphenyl)propyl, 4-(3,4-dimethoxyphenyl)butyl, 1,1-dimethyl-2-(2,5-dimethoxyphenyl)ethyl, 5-(3,4,5-trimethoxyphenyl)pentyl, 6-(3-pentyloxyphenyl)hexyl, 2-methyl-3-(2-n-butyloxyphenyl)propyl, 3,4-methylenedioxybenzyl, 2-(2,4-methylenedioxyphenyl)ethyl, 1-(3,4-ethylenedioxyphenyl)ethyl, 3-(2,3-trimethylenedioxyphenyl)propyl, 4-(3,4-tetramethylenedioxyphenyl)butyl, 1,1-dimethyl-2-(3,4-methylenedioxyphenyl)ethyl, 5-(2,3-methylenedioxyphenyl)pentyl and 6-(3,4-ethylenedioxyphenyl)hexyl groups.

As to the lower alkylamino-lower alkyl group, an alkylaminoalkyl group in which the alkyl moiety is a straight chain- or branched chain-alkyl group having 1 to 6 carbon atoms, and the alkylamino moiety is an amino group having 1 to 2 straight chain- or branched chain-alkyl groups having 1 to 6 carbon atoms as the substituents, such as methylaminomethyl, 2-(ethylamino)ethyl, 1-(propylamino)ethyl, 3-(n-butylamino)propyl, 4-(pentylamino)butyl, 5-(hexylamino)pentyl, 6-(dimethylamino)hexyl, 2-methyl-3-(diethylamino)propyl, 1,1-dimethyl-2-(diisopropylamino)ethyl, 3-(dihexylamino)propyl, 4-(methylethylamino)butyl, 5-(methylpentylamino)pentyl, 6-(ethylpropylamino)hexyl, 2-methyl-3-(methylhexylamino)propyl and 1,1-dimethyl-2-(dimethylamino)ethyl groups can be exemplified.

As to the alkyl group which may have at least one hydroxy group as the substituent, a straight chain-or branched chain-alkyl group having 1 to 6 carbon atoms which may have at least one hydroxy group as the substituent, there can be exemplified, in addition to the above-mentioned lower alkyl groups, such as hydroxymethyl, 1-hydroxyethyl, 2-hydroxyethyl, 3-hydroxypropyl, 4-hydroxybutyl, 5-hydroxypentyl, 6-hydroxyhexyl, 2-methyl-3-hydroxypropyl and 1,1-dimethyl-2-hydroxyethyl groups.

As to the alkyl group which may have at least one halogen atom as the substituent, a straight chain-or branched chain-alkyl group having 1 to 6 carbon atoms which may have 1 to 3 halogen atoms as the substituents, there can be exemplified, in addition to the above-mentioned lower alkyl groups, such as trifluoromethyl, trichloromethyl, chloromethyl, bromomethyl, fluoromethyl, iodomethyl, difluoromethyl, dibromomethyl, 2,2,2-trifluoroethyl, 2,2,2-trichloroethyl, 2-chloroethyl, 1,2-dichloroethyl, 3,3,3-trichloropropyl, 4-fluorobutyl, 5-chloropentyl, 3-chloro-2-methylpropyl, 6-bromohexyl, 5,6-dibromohexyl and 2,2-dichloropentyl groups.

As to the benzoyl group which may have at least one alkoxy group as the substituents on the phenyl ring, a benzoyl group which may have 1 to 3 straight chain- or branched chain-alkoxy group having 1 to 6 carbon atoms on the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 4-hexyloxybenzoyl, 3,4-dimethoxybenzoyl, 3,4-diethoxybenzoyl, 3,4,5-trimethoxybenzoyl and 2,5-dimethoxybenzoyl groups can be exemplified.

As to the lower alkylenedioxy group, a straight chain- or branched chain-alkylenedioxy group having 1 to 4 carbon atoms in the alkylene moiety, such as methylenedioxy, ethylenedioxy, trimethylenedioxy and tetramethylenedioxy groups can be exemplified.

As to the cycloalkyl-lower alkyl group, a cycloalkylalkyl group in which the cycloalkyl moiety having 3 to 8 carbon atoms and the alkyl moiety having 1 to 6 carbon atoms, such as cyclopropylmethyl, 2-cyclobutylethyl, 1-cyclopentylethyl, 3-cyclopentylpropyl, 4-cyclohexylbutyl, 1,1-dimethyl-2-cycloheptylethyl, 5-cyclooctylpentyl, 6-cyclohexylhexyl and 2-methyl-3-cyclohexylpropyl groups can be exemplified.

As to the pyrrolidinylcarbonyl-lower alkyl group, a pyrrolidinylcarbonylalkyl group in which the alkyl moiety is a straight chain or branched chain alkyl group having 1 to 6 carbon atoms, such as pyrrolidinylcarbonylmethyl, 2-pyrrolidinylcarbonylethyl, 1-pyrrolidinylcarbonylethyl, 3-pyrrolidinylcarbonylpropyl, 4-pyrrolidinylcarbonylbutyl, 1,1-dimethyl-2-pyrrolidinylcarbonylethyl, 5-pyrrolidinylcarbonylpentyl, 6-pyrrolidinylcarbonylhexyl and 2-methyl-3-pyrrolidinylcarbonyl propyl groups can be exemplified.

The 2,3-dihydro-1H-indene derivatives and salts thereof according to the present invention can be prepared by various processes, and some of typical processes are shown as follows.

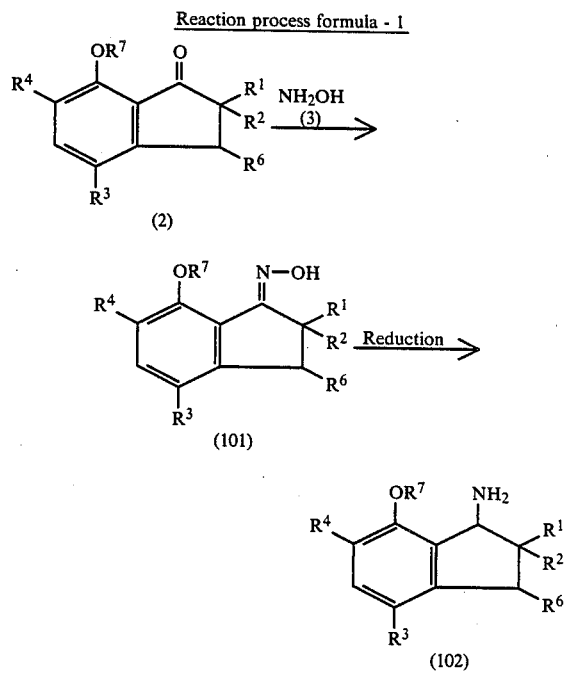

[wherein $R^1$, $R^2$, $R^3$, $R^4$, $R^6$ and $R^7$ are the same as defined above].

The reaction of a compound of the general formula (2) with hydroxylamine (3) can be carried out in a suitable solvent in the absence or presence of a basic compound.

As to the basic compound used in this reaction, an inorganic basic compound such as sodium hydroxide, potassium hydroxide, sodium carbonate or potassium carbonate; an organic basic compound such as piperidine, pyridine, triethylamine, 1,5-diazabicyclo[4,3,0]nonene-5 (DBN), 1,8-diazabicyclo[5,4,0]undecene-7 (DBU) or 1,4-diazabicyclo[2,2,2]octane (DABCO) may be exemplified.

As to the inert solvent used in this reaction, any solvent which does not give any adverse effect to the reaction can be used, for example lower alcohols such as methanol, ethanol and isopropanol; ethers such as dioxane, tetrahydrofuran, diethyl ether and ethylene glycol monomethyl ether; aromatic hydrocarbons such as benzene toluene and xylene; halogenated hydrocarbons such as dichloromethane, dichloroethane, chloroform and carbon tetrachloride; dimethylformamide, dimethyl sulfoxide and hexamethylphosphoric triamide can be exemplified.

The ratio of the amount of hydroxylamine (3) to the amount of a compound of the general formula (2) may generally be at least an equimolar quantity, preferably an equimolar quantity to 5 times the molar quantity of the former to the latter.

The reaction can be carried out generally at room temperature to 200° C., preferably at 50° to 150° C., and the reaction is completed generally within about 1 to 10 hours.

The reduction of a compound of the general formula (101) can be carried out under conditions similar to those employed in the reduction of a compound of the general formula (104) in the after-cited Reaction process formula - 2, preferably can be carried out by catalytic hydrogenation in a suitable solvent in the presence of a catalyst.

As to the solvent used in the catalytic hydrogenation, water, acetic acid, alcohols such as methanol, ethanol, isopropanol; hydrocarbons such as hexane and cyclohexane; ethers such as diethylene glycol dimethyl ether, dioxane, tetrahydrofuran and diethyl ether; esters such as ethyl acetate and methyl acetate; aprotic polar solvents such as dimethylformamide; and mixed solvent thereof can be exemplified.

As to the catalyst used in this catalytic hydrogenation, palladium, palladium black, palladium-carbon, platinum, platinum oxide, copper chromite and Raney-nickel can be exemplified. The amount of the catalyst used in the catalytic hydrogenation, generally 0.02 to 1 time quantity may be used to the amount of a compound of the general formula (101). The catalytic hydrogenation may be carried out generally at about −20° C. to 100° C., preferably at about 0° C. to 70° C., and generally under 1 to 10 atmospheric pressure of hydrogen, the catalytic hydrogenation is generally completed within about 0.5 to 20 hours.

When the catalytic hydrogenation of a compound of the general formula (101) wherein $R^1$, $R^2$ or $R^4$ is a phenyl group, a phenyl-lower alkyl group or a pyridinium-lower alkanoylamino-lower alkyl group, is carried out under the conditions as mentioned above, sometimes a compound of the general formula (102) in which $R^1$, $R^2$ or $R^4$ is a cyclohexyl group, a cyclohexyl-lower alkyl group or piperidinium-lower alkyl group may be formed. Further the halogen atom in $R^3$ or $R^4$ in the general formula (102) may be reduced to change to hydrogen atom.

Reaction process formula - 2

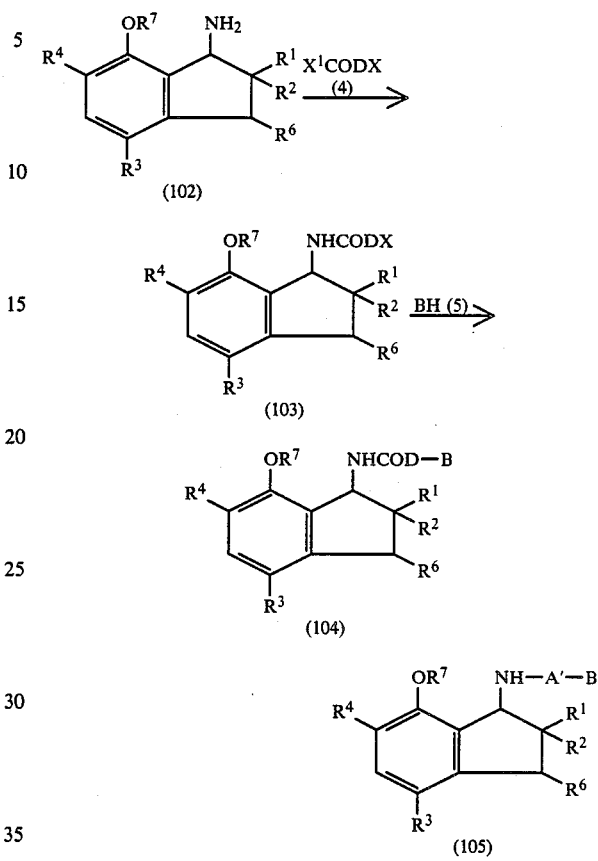

[wherein $R^1$, $R^2$, $R^3$, $R^4$, $R^6$, $R^7$, B and D are the same as defined above; $X^1$ is a halogen atom; X is a hydrogen atom or a halogen atom; A' is a lower alkylene group].

The reaction of a compound of the general formula (102) with a compound of the general formula (4) is carried out in a suitable inert solvent, in the presence of a dehydrohalogenating agent. As to the inert solvent used in this reaction, halogenated hydrocarbons such as dichloromethane and chloroform; ethers such as tetrahydrofuran and diethyl ether; aromatic hydrocarbons such as benzene, toluene and xylene; esters such as methyl acetate and ethyl acetate, polar solvents such as dimethylformamide, dimethyl sulfoxide, hexamethylphosphoric triamide, acetonitrile, acetone, acetic acid, pyridine and water can be exemplified. As to the dehydrohalogenating agent used in this reaction, organic basic compounds such as triethylamine, trimethylamine, pyridine, dimethylaniline, N-methylmorpholine, 4-dimethylaminopyridine, 4-(1-pyrrolidinyl)pyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and sodium acetate; and inorganic basic compounds such as potassium carbonate, sodium carbonate, potassium bicarbonate, sodium bicarbonate, potassium hydroxide and sodium hydroxide can be exemplified.

The ratio of the amount of a compound of the general formula (4) to the amount of a compound of the general formula (102) may be generally at least an equimolar quantity, preferably an equimolar quantity to 2 times the molar quantity of the former to the latter. The reaction is carried out generally about at −20° C. to 150° C., preferably about at 0° C. to 100° C., and is completed within about 5 minutes to 7 hours. Thus, a compound of the general formula (103) is prepared.

In the case of using a compound of the general formula (103) in which X is a halogen atom, a compound of the general formula (104) can be introduced by reacting such compound of the geeral formula (103) with a compound of the general formula (5). The reaction of the compound of the general formula (103) with a compound of the general formula (5) is carried out in a suitable inert solvent in the presence of a dehydrohalogenating agent. As to the inert solvent used in this reaction, alcohols such methanol, ethanol, propanol, butanol, 3-methoxy-1-butanol, ethyl cellosolve and methyl cellosolve; ethers such as tetrahydrofuran, diethyl ether; aromatic hydrocarbons such as benzene, toluene, xylene; aprotic polar solvents such as acetone, acetonitrile, dimethylformamide, dimethyl sulfoxide and hexamethylphosphoric triamide; halogenated hydrocarbons such as methylene chloride, dichloroethane and chloroform; esters such as methyl acetate and ethyl acetate; and mixed solvents thereof can be exemplified. As to the dehydrohalogenating agent used in this reaction, usual basic compounds for example, organic basic compounds such as triethylamine, trimethylamine, pyridine, dimethylaniline, N-methylmorpholine, 4-dimethylaminopyridine, 4-(1-pyrrolidinyl)pyridine, DBN, DBU, DABCO and sodium acetate; inorganic basic compounds such as potassium carbonate, sodium carbonate, potassium bicarbonate, sodium bicarbonate, potassium hydroxide, sodium hydroxide, potassium hydride, sodium hydride and sodium amide; alkali metal alcoholates such as sodium methylate and sodium ethylate, can be exemplified.

The ratio of the amount of a compound of the formula (5) to the amount of a compound of the general formula (103) may be generally at least an equimolar quantity, preferably an equimolar quantity to 3 times the molar quantity of the former to the latter. Further, an excess amount of a compound of the formula (5) may also be used as the dehydrohalogenating agent.

The reaction is generally carried out about at 0° C. to 120° C., preferably about room temperature to 100° C., and is completed within about 0.5 to 10 hours. Thus compound of the general formula (104) can be obtained.

In some cases, a compound of the general formula (120),

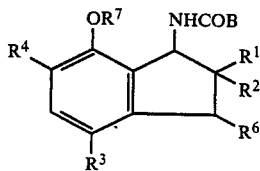

(120)

may also be obtained in the above-mentioned reaction under similar conditions. The compound of the general formula (120) and the compound of the general formula (104) can easily be separated from each other by usual separating means.

The reaction for obtaining a compound of the general formula (105) by reducing a compound of the general formula (104) can be carried out by various method, for example, the reduction conditions of a compound of the general formula (101) employed in the above-mentioned Reaction process formula - 1, preferably, reduction by using hydrogenating agent may be employed. As to the hydrogenating agent, lithium aluminum hydride, sodium boron hydride and diborane can be exemplified. The ratio of the amount of said hydrogenating agent to the amount of a compound of the general formula (104) is generally at least an equimolar quantity, preferably about an equimolar quantity to 10 times the molar quantity of the former to the latter. The reduction is generally carried out in a suitable solvent, for example water, lower alcohol such as methanol, ethanol or isopropanol; ether such as tetrahydrofuran, diethyl ether or diglyme; or acetic acid, and generally at about 0° to 200° C., preferably about at 0° to 170° C., for about 10 minutes to 10 hours. In case of using lithium aluminum hydride or diborane as the reducing agent, an anhydrous solvent such as diethyl ether, tetrahydrofuran or diglyme may be used.

Reaction process formula - 3

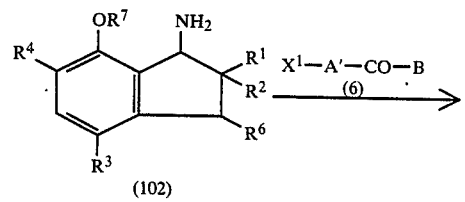

(102)

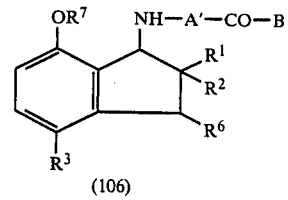

(106)

[wherein $R^1$, $R^2$, $R^3$, $R^4$, $R^6$, $R^7$, $X^1$, A' and B are the same as defined above].

The reaction of a compound of the general formula (102) with a compound of the general formula (6) can be carried out under conditions similar to those employed in the reaction of a compound of the general formula (102) with a compound of the genral formula (4) in the above-mentioned Reaction process formula -2.

Reaction process formula - 4

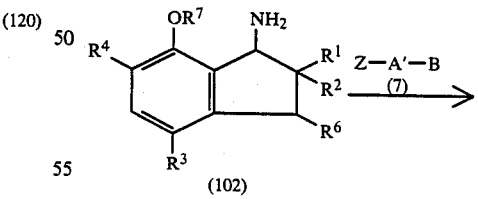

(102)

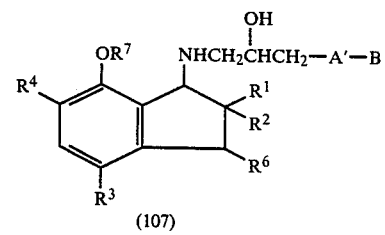

(107)

[wherein $R^1$, $R^2$, $R^3$, $R^4$, $R^6$, $R^7$, A' and B are the same as defined above; Z is a group of the formula

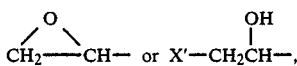

provided that the number of carbon atoms in a group of the formula

should not be exceeded 6].

The reaction of a compound of the general formula (102) with a compound of the general formula (7) is carried out with or without in a suitable solvent, in the presence of a basic compound. As to the solvent used in this reaction, ethers, such as dioxane, tetrahydrofuran and ethylene glycol diethyl ether; aromatic hydrocarbons such as benzene toluene and xylene; alcohols such as methanol, ethanol and isopropanol; aprotic polar solvents such as acetone, acetonitrile, dimethylformamide, dimethyl sulfoxide and hexamethylphosphoric triamid can be exemplified. As to the basic compound used in the reaction, inorganic basic compounds such as potassium carbonate, sodium carbonate, potassium hydroxide, sodium hydroxide, sodium bicarbonate and sodium amide; organic basic compounds such as triethylamine, tripropylamine, pyridine, quinoline, DBN, DBU and DABCO can be exemplified. The ratio of the amount of a compound of the general formula (7) to the amount of a compound of the general formula (102) may be generally at least an equimolar quantity, preferably an equimolar quantity to 5 times the molar quantity of the former to the latter. The reaction is carried out generally at about 0° C. to 200° C., preferably at about 50° to 100° C., and is completed within about 1 to 12 hours.

Reaction process formula - 5

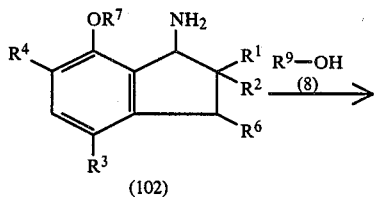

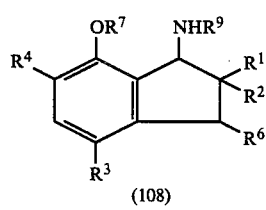

[wherein $R^1$, $R^2$, $R^3$, $R^4$, $R^6$ and $R^7$ are the same as defined above; and $R^9$ is a halogen-substituted lower alkanoyl group].

The reaction of a compound of the general formula (102) with a compound of the general formula (8) is carried out by an usual method of amide bond formation reaction. In carrying out said amide bond formation reaction, an activated compound of a carboxylic acid of the general formula (8) may be used. As to the amide bond formation reaction, reaction conditions usually employed in amide bond formation reaction can be used. For example, (a) a mixed acid anhydride method, i.e., by reacting a carboxylic acid of the general formula (8) with an alkylhalocarboxylic acid to form the corresponding mixed acid anhydride, then a compound of the general formula (102) is reacted therewith; (b) an activated ester method or activated amide method, i.e., by converting a carboxylic acid of the general formula (8) into the corresponding activated ester such as p-nitrophenyl ester, N-hydroxysuccinimide ester or 1-hydroxybenzotriazol ester, or into the corresponding activated amide such as benzoxazolin-2-thion, then a compound of the general formula (102) is reacted with said activated ester or with said activated amide; (c) a carbodiimide method, i.e., by condensing a carboxylic acid of the general formula (8) with a compound of the general formula (102) in the presence of a dehydrating agent such as dicyclohexylcarbodiimide or carbonyl diimidazol; (d) a carboxylic acid halide method, i.e., by converting a carboxylic acid of the general formula (8) into the corresponding halide, then a compound of the general formula (102) is reacted therewith; (e) other method, a carboxylic acid anhydride method, i.e., by converting a carboxylic acid of the general formula (8) into the corresponding carboxylic acid anhydride by using dehydrating agent such as acetic anhydride, then a compound of the general formula (102) is reacted therewith; and (f) a high pressure-high temperature methode, i.e., by reacting an ester prepared from a carboxylic acid of the general formula (8) with a lower alcohol, with a compound of the general formula (102) under a high pressure at a high temperature, can be exemplified. Further, other method, (g) by activating a carboxylic acid of the general formula (8) with a phosphorus compound such as triphenylphosphine or diethylchlorophosphate, then a compound of the general formula (102) is reacted with said activated carboxylic acid, can be employed.

As to the alkylhalocarboxylic acid used in the above-mentioned (a) mixed acid anhydride method, methyl chloroformate, methyl bromoformate, ethyl chloroformate, ethyl bromoformate and isobutyl chloroformate can be exemplified. The mixed acid anhydride is prepared by an usual Schötten-Baumann reaction, and generally, said mixed acid anhydride may be used without isolated, and reacted with a compound of the general formula (102) to prepare a compound of the general formula (1). Schötten-Baumann reaction is generally carried out in the presence of a basic compound. As to the basic compound used in the reaction, any basic compound used conventionally in Schötten-Baumann reaction may be used, for example organic basic compounds such as triethylamine, trimethylamine, pyridine, dimethylaniline, N-methylmorpholine, 4-dimethylaminopyridine, DBN, DBU and DABCO; and inorganic basic compounds such as potassium carbonate, sodium carbonate, potassium bicarbonate and sodium bicarbonate can be exemplified. The reaction is carried out at about −20° C. to 100° C., preferably at about 0° C. to 50° C., for about 5 minutes to 10 hours, preferably for about 5 minutes to 2 hours. The reaction of thus obtained mixed acid anhydride with a compound of the general formula (102) is carried out at about −20° C. to 150° C., preferably at about 10° to 50° C., for about 5 minutes to 10 hours, preferably for about 5 minutes to 5 hours. The reaction of mixed acid anhydride may not specifically be carried in a solvent, but generally is carried out in a solvent. As to the solvent used in the reaction, any solvent employed conventionally in the mixed acid anhydride method can be used, and specifically, halogenated hydrocarbons such as methylene chloride, chloroform and dichloroethane; aromatic hydrocarbons such as benzene, toluene and xylene; ethers such as diethyl ether, diisopropyl ether, tetrahydrofuran and dimethoxyethane; esters such as methyl acetate and ethyl acetate; aprotic polar solvents such as dimethylformamide, dimethyl sulfoxide and hexamethylphosphoric triamide can be exemplified. The ratios of the amount of a carboxylic acid of the general formula (8), the amount of an alkylhalocarboxylic acid and the amount of a compound of the general formula (102) are generally at least an equimolar quantity of each, and preferably 1 to 2 times the molar quantity each of an alkylhalocarboxylic acid and a compound of the general formula (102) may be used to a carboxylic acid of the general formula (8).

In carrying out the above-mentioned (b) an activated ester method or an activated amide method, in case of using benzoxazolin-2-thionamide, the reaction is carried out in a suitable solvent which does not give any adverse effect to the reaction, for example a solvent similar to that used in the above-mentioned mixed acid anhydride methode, and further using 1-methyl-2-pyrrolidone, at about 0° to 150° C., preferably at about 10° to 100° C., for 0.5 to 75 hours. The ratio of the amount of a compound of the general formula (102) to the amount of benzoxazolin-2-thionamide is generally at least an equimolar quantity, preferably an equimolar to 2 times the molar quantity of the latter is used to the former. In case of using N-hydroxysuccinimide ester, the reaction is carried out advantageously by using a suitable basic compound similar to that employed in the after cited (d) carboxylic acid halide method.

In carrying out the above-mentioned (d) carboxylic acid halide method, the reaction is conducted by reacting a carboxylic acid of the general formula (8) with a halogenating agent to prepare the corresponding carboxylic acid halide, then said carboxylic acid halide is isolated and purified from the reaction system or without isolated and purified, then is reacted with a compound of the general formula (102). The reaction of said carboxylic acid halide with a compound of the general formula (102) is carried out in a suitable solvent in the presence of a dehydrohalogenating agent. As to the dehydrohalogenating agent used in the reaction, generally a basic compound is used, and other than the basic compounds used in the above-mentioned Schötten-Baumann reaction, sodium hydroxide, potassium hydroxide, sodium hydride, potassium hydride, silver carbonate, an alkali metal alcoholate such as sodium methylate or sodium ethylate can be exemplified. Further, an excess amount of a compound of the general formula (102) can also be used as the dehydrohalogenating agent. As to the solvent used in this reaction, other than the solvents used in the above-mentioned Schötten-Baumann reaction, water, alcohols such as methanol, ethanol, propanol, butanol, 3-methoxy-1-butanol and ethyl cellosolve; pyridine, acetone, and acetonitrile; and mixed solvents of at least 2 or more of the above-mentioned solvents can be exemplified. The ratio of the amount of a carboxylic acid of the general formula (102) to the amount of said carboxylic acid halide is not restricted within the specific range, and can be selected from a wide range, generally at least an equimolar quantity, preferably an equimolar to 2 times the molar quantity of the latter is used to the former. The reaction is generally carried out at about −30° C. to 180° C., preferably at about 0° C. to 150° C., and is completed generally in about 5 minutes to 30 hours. The carboxylic acid halide is prepared by reacting a carboxylic acid of the general formula (8) with a halogenating agent in the presence or absence of a solvent. As to the solvent, any solvent which does not give any adverse effect to the reaction can be used, for example aromatic hydrocarbons such as benzene, toluene and xylene; halogenated hydrocarbons such as chloroform, methylene chloride, and carbon tetrachloride; ethers such as dioxane, tetrahydrofuran, and diethyl ether; dimethylformamide and dimethyl sulfoxide can be exemplified. As to the halogenating agent, a usual halogenating agents which can be able to convert the hydroxyl group in carboxy group into halogen atoms can be used, for example thionyl chloride, phosphorus oxychloride, phosphorus oxybromide, phosphorus pentachloride and phosphorus pentabromide can be exemplified. Ratio of the amount of carboxylic acid (8) to the amount of halogenating agent is not specifically restricted, and can be selected from a wide range. In the case of carrying out the halogenation in the absence of solvent, a large excess amount of the latter is used to the former. While, when the halogenation is carried out in the presence of a solvent, at least an equimolar quantity, preferably 2 to 4 times the molar quantity of the latter is used to the former. The reaction temperature and the reaction time may not be specifically restricted, and generally the reaction is carried out at about room temperature to 100° C., preferably at about 50° to 80° C., for about in 30 minutes to 6 hours.

In carrying out the above-mentioned method (g) in which a carboxylic acid (8) is activated by using a phosphorus compound such as triphenylphosphine or diethylchlorophosphate, the reaction is carried out in a suitable solvent. As to the solvent used in this reaction, any inert solvent which does not give any adverse effect to the reaction can be used, for example halogenated hydrocarbons such as methylene chloride, chloroform and dichloroethane; aromatic hydrocarbons such as benzene, toluene and xylene; ethers such as diethyl ether, tetrahydrofuran and dimethoxyethane; esters such as methyl acetate and ethyl acetate; aprotic polar solvents such as dimethylformamide, dimethyl sulfoxide and hexamethylphosphoric triamide can be exemplified. In this reaction, since a compound (102) per se acts as the basic compound, the reaction is proceeded advantageously by using said compound (102) in an amount over stoichiometric quantity. If necessary, other basic compounds, for example organic basic compounds such as triethylamine, trimethylamine, pyridine, dimethylaniline, N-methylmorpholine, 4-dimethylaminopyridine, DBN, DBU and DABCO; and inorganic basic compounds such as potassium carbonate, sodium carbonate, potassium bicarbonate and sodium bicarbonate can be used. The reaction is achieved at a temperature of 0° C. to 150° C., preferably at about 0° C. to 100° C., for about in 1 to 30 hours. Ratios of the amounts of the phosphorus compound and a carboxylic acid (8) to the amount of a compound (102) are generally at least equimolar quantities, preferably equimolar to 3 times the molar quantity, respectively.

Reaction process formula - 6

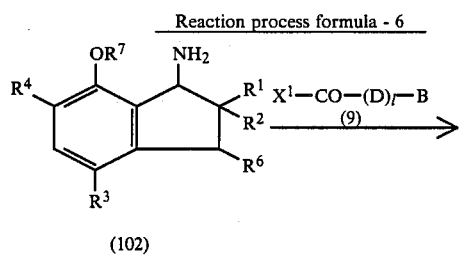

(102)

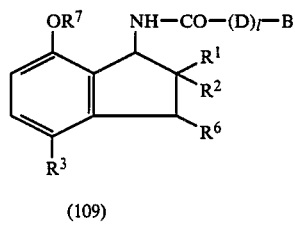

(109)

[$R^1$, $R^2$, $R^3$, $R^4$, $R^6$, $R^7$, B, D, l and $X^1$ are the same as defined above].

The reaction of a compound (102) with a compound (9) can be carried out under conditions similar to those employed in the reaction of a compound (102) with a compound (4) in the above-mentioned Reaction process formula - 2.

The compounds (102) used as the starting materials in the above-mentioned Reaction process formulas - 1, -2, -3, -4, -5 and -6 contain novel compounds, and are prepared through the following methods.

Reaction process formula - 7

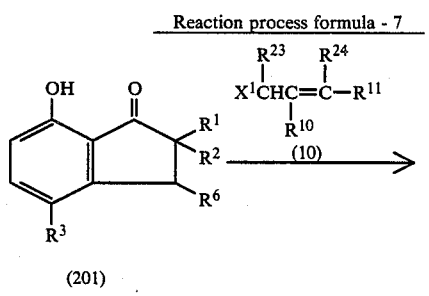

(201)

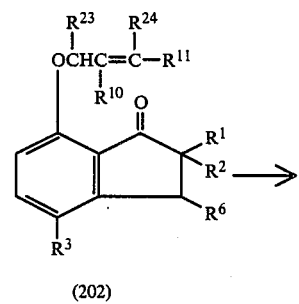

(202)

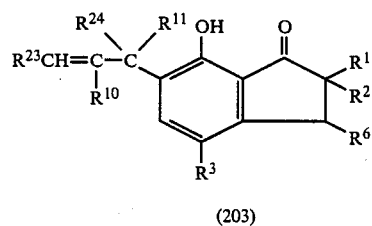

(203)

[wherein $R^1$, $R^2$, $R^3$, $R^6$ and $X^1$ are the same as defined above; and $R^{10}$, $R^{11}$, $R^{23}$ and $R^{24}$ are each a hydrogen atom, a lower alkyl group, a phenyl group or a cycloalkyl group].

The reaction of a compound of the general formula (201) with a compound of the general formula (10) is carried out in the presence of a basic compound. As to the basic compound used in this reaction, any known basic compound can be used, for example inorganic basic compounds such assodium hydroxide, potassium hydroxide, sodium carbonate, potassium carbonate, sodium bicarbonate, potassium bicarbonate and silver carbonate; alkali metals such as sodium metal and potassium metal; alkali metal clcoholates such as sodium methylate and sodium ethylate; organic basic compounds such as triethylamine, pyridine, N,N-dimethylaniline, N-methylmorpholine, 4-dimethylaminopyridine, DBN, DBU and DABCO can be exemplified. The reaction is carried out without or in a solvent. As to the solvent used in this reaction, any inert solvent which does not give any adverse effect to the reaction can be used, for example water, alcohols such as methanol, ethanol, propanol, butanol, ethylene glycol; ethers such as dimethyl ether, tetrahydrofuran, dioxane, monoglyme and diglyme; ketones such as acetone, methyl ethyl ketone; aromatic hydrocarbons such as benzene, toluene and xylene; esters methyl acetate and ethyl acetate; aprotic polar solvents such as N,N-methylformamide, dimethyl sulfoxide, hexamethylphosphoric triamide; and mixed solvents thereof can be exemplified. Further, the reaction is advantageously carried out in the presence of a metal iodide such as sodium iodide or potassium iodide.

Ratio of the amount of a compound of the general formula (201) to the amount of a compound of the general formula (8) is not specifically restricted, and can be selected from a wide range, generally an equimolar quantity to 5 times the molar quantity, preferably an equimolar quantity to 2 times the molar quantity of the latter is used to the former. The reaction temperature is also not specifically restricted, and generally the reaction is carried out within room temperature to 200° C., preferably at 50° to 150° C., and the reaction time is generally in 1 to 30 hours, preferably in 1 to 15 hours.

The reaction for obtaining a compound of the general formula (203) from a compound of the general formula (202) is generally called as "Claisen Rearrangement", and can be carried out by heating a compound of the general formula (202) in a suitable solvent to introduced to a compound of the general formula (203). As to the solvent used in this rearrangement reaction, a solvent having higher boiling point such as dimethylformamide and tetrahydronaphthalene can be exemplified. The rearrangement reaction is generally carried out at 100° to 250° C., preferably at 150° to 250° C., and is completed in 1 to 20 hours.

Reaction process formula - 8

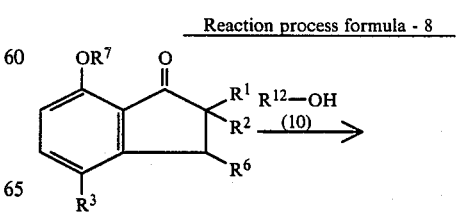

(201)

-continued

Reaction process formula - 8

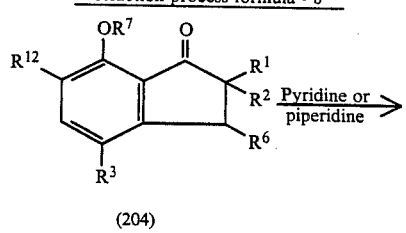

(204)

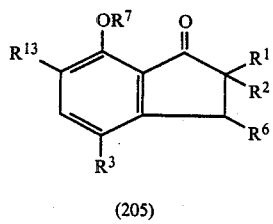

(205)

[wherein $R^1$, $R^2$, $R^3$, $R^6$ and $R^7$ are the same as defined above; $R^{12}$ is a lower alkanoylamino-lower alkyl group having halogen atoms as the substituents; and $R^{13}$ is a pyridinium-lower alkanoylamino-lower alkyl group or piperidinyl-lower alkanoylamino-lower alkyl group].

The reaction of a compound of the general formula (201) with a compound of the general formula (10) is carried out in the presence of a dehydro-condensing agent, without or in a suitable solvent. As to the dehydro-condensing agent used in this reaction, condensed phosphoric acids such as polyphosphoric acids; phosphoric acids such as orthophosphoric acid, pyrophosphoric acid, metaphosphoric acid; phosphorous acids such as orthophosphorous acid; phosphoric acid anhydrides such as phosphorous pentoxide; mineral acids such as hydrochloric acid, sulfuric acid, boric acid; metal phosphates such as sodium phosphate, boron phosphate, ferric phosphate and aluminum phosphate; activated alumina, sodium bisulfate and Raney-nickel can be exemplified. As to the solvent used in this reaction, dimethylformamide and tetrahydronaphthalene can be exemplified.

Ratio of the amount of a compound of the general formula (201) to the amount of a compound of the general formula (10) is not specifically restricted, and can be selected from a wide range, and generally an equimolar quantity, preferably an equimolar to 2 times the molar quantity of the latter is used to the former. The amount of the dehydro-condensing agent is not restricted specifically, and can be selected from a wide range, generally a catalytic amount, preferably a large excess amount thereof may be used to a compound of the general formula (201). The reaction is generally advantageously carried out at −30° to 50° C., preferably at about 0° C. to room temperature, and is completed in about 1 to 30 hours.

The reaction of a compound of the general formula (204) with pyridine or piperidine can be carried out under conditions similar to those employed in the reaction of a compound of the general formula (102) with a compound of the general formula (4).

Both compound of the general formula (6) and compound of the general formula (9) include novel compounds and can be prepared by, for example the following processes.

Reaction process formula - 9

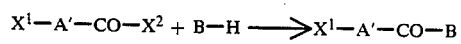

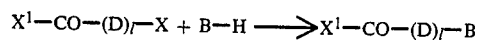

[wherein X, $X^1$, $X^2$, A, l, D and B are the same as defined above].

Both reaction of a compound (11) with a compound (5) and reaction of a compound (4) with a compound (5) can be carried out under conditions similar to those employed in the reaction of a compound (102) with a compound (4) in the above-mentioned Reaction process formula - 2.

Compound represented by the general formula (7) contain some novel compounds, and they can be prepared by methode for example the following process.

Reaction process formula - 10

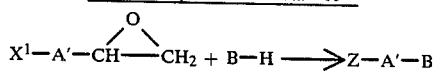

[wherein $X^1$, A', Z and B are the same as defined above].

The reaction of a compound (12) with a compound (5) is carried out in a suitable solvent or without the solvent in the presence of a basic compound. As to the basic compound inorganic basic materials such as sodium hydroxide, potassium hydroxide, sodium carbonate, potassium carbonate, sodium methoxide, sodium ethoxide, sodium hydride, metallic sodium and metallic potassium; and organic basic compounds such as piperidine, pyridine, triethylamine, DBN, DBU and DABCO can be exemplified. As to the solvent used in this reaction, ketones such as acetone and methyl ethyl ketone; ethers such as diethyl ether, dioxane and diethylene glycol dimethyl ether; aromatic hydrocarbons such as benzene, toluene and xylene; acetonitrile and water can be exemplified. Furthermore, a compound (12) may be used as the solvent. Ratio of the amount of a compound (12) to the amount of a compound (5) may be generally an excess quantity, preferably 5 to 10 times the molar quantity of the former to the latter. The reaction is carried out generally at about 0° C. to 150° C., preferably 50° to 100° C., and is finished generally within 1 to 12 hours.

Reaction process formula - 11

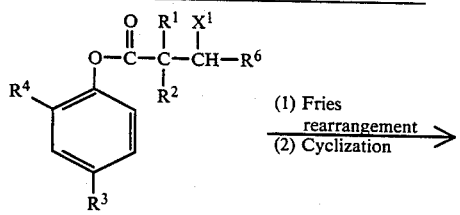

(206)

(1) Fries rearrangement
(2) Cyclization

-continued
Reaction process formula - 11

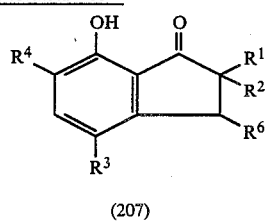
(207)

[wherein $R^1$, $R^2$, $R^3$, $R^4$, $R^6$ and $X^1$ are the same as defined above].

The Fries rearrangement subsequent cyclization reaction of a compound of the general formula (206) to form a compound of the general formula (207) can be carried out in the presence of an acid, in a suitable solvent or without the solvent. As tw the acid used in the reaction, aluminum chloride, zinc chloride, iron chloride, tin chloride, born trifluoride, born tribromide and concentrated sulfuric acid can be exemplified. As to the solvent used in this reaction, carbon disulfide, aromatic hydrocarbons such as nitrobenzene, chlorobenzens; halogenated hydrocarbons such as dichloromethane, dichloroethane, trichloroethane and tetrachloroethane can be exemplified. The amount of the Lewis acid to be used may be determined properly, and generally at least an equimolar quantity, preferably an equimolar quantity to 6 times the molar quantity thereof is used to a compound of the general formula (206). The Fries rearrangement subsequent cyclization reaction is generally carried out at room temperature to 200° C., preferably at about 50° to 180° C., for about 10 minutes to 7 hours.

Reaction process formula - 12

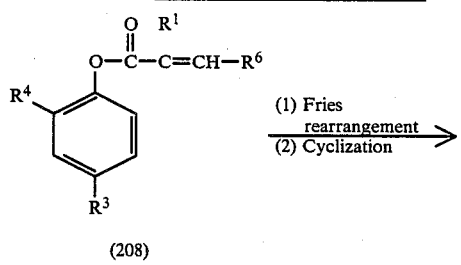
(208)

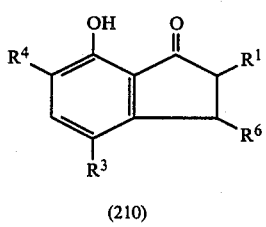
(210)

[wherein $R^1$, $R^3$, $R^4$ and $R^6$ are the same as defined above].

The Fries rearrangement subsequent cyclization of a compound of the general formula (208) can be carried out under conditions similar to those employed in the cyclization of a compound of the general formula (206) in the above-mentioned Reaction process formula - 11.

Reaction process formula - 13

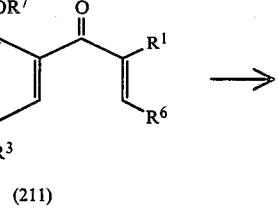
(211)

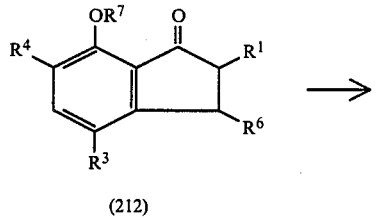
(212)

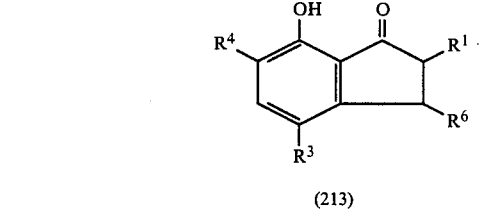
(213)

[wherein $R^1$, $R^3$, $R^4$, $R^6$ and $R^7$ are the same as defined above].

The cyclization of a compound of the general formula (211) can be carried out in the presence of an acid, in a suitable solvent. As to the acid used in this reaction, inorganic acids such as hydrochloric acid, sulfuric acid, hydrobromic acid; organic acids for example alkanoic acids such as acetic acid, trifluoroacetic acid and other organic acids such as p-toluenesulfonic acid can be exemplified. As to the solvent used in this cyclization, alcohols such as methanol, ethanol and isopropanol; aromatic hydrocarbons such as benzene, toluene and xylene; halogenated hydrocarbons such as dichloromethane, dichloroethane, chloroform and carbon tetrachloride; ethers such as diethyl ether, tetrahydrofuran, dioxane, diglyme and monoglyme; aprotic polar solvents such as dimethylformamide, dimethyl sulfoxide and hexamethylphosphoric triamide can be exemplified. The cyclization can be carried out, generally at about 0° to 150° C., preferably at about 0° to 100° C., for about 30 minutes to 24 hours to complete the reaction.

The reaction for introducing a compound of the general formula (212) to a compound of the general formula (213) can be carried out by treating the former in a suitable solvent, for example water, a lower alcohol such as methanol, ethanol or isopropanol; an ether such as dioxane or tetrahydrofuran; or acetic acid; or a mixed solvent thereof, in the presence of a catalytic reduction catalyst such as palladium-carbon or palladium-black, at a temperature of about 0° to 100° C., under 1 to 10 atmospheric pressure of hydrogen gas, for 0.5 to 3 hours, or by heat treating a compound of the general formula (212) with a mixture of an acid such as hydrobromic acid or hydrochloric acid and a solvent such as water, methanol, ethanol or isopropanol, at a temperature of 30° to 150° C., preferably at 50° to 120° C., to introduce a compound of the general formula (213).

Furthermore, a compound of the general formula (213) can also be obtained by hydrolyzing a compound of the general formula (212). This hydrolysis can be carried out in a suitable solvent in the presence of an acid or basic compound. As to the solvent used in this hydrolysis, water, lower alcohols such as methanol, ethanol and isopropanol; ethers dioxane and tetrahydrofuran; aprotic polar solvents such as acetonitrile; and mixtures of these solvents can be exemplified. As to the acid used in this hydrolysis, mineral acids such as hydrochloric acid, hydrobromic acid and sulfuric acid; Lewis acids such as aluminum chloride; metal iodides such as sodium iodide and potassium iodided; and mixtures of the Lewis acid with the iodide can be exemplified. As to the basic compound used in the hydrolysis, metal hydroxides such as sodium hydroxide, potassium hydroxide and calcium hydroxide can be exemplified. The hydrolysis can advantageously be carried out generally at room temperature to 150° C., preferably at room temperature to 100° C., and completed in 0.5 to 15 hours.

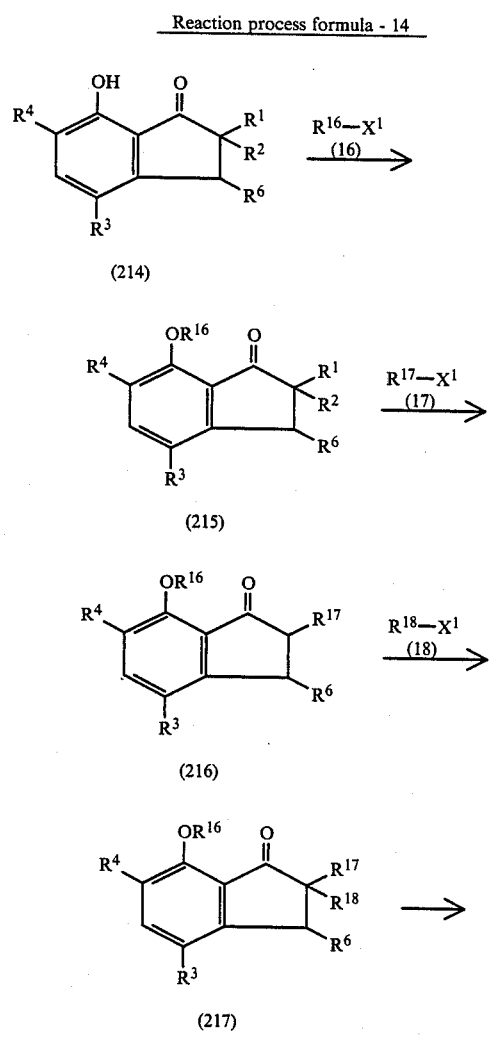

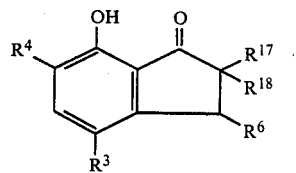

[wherein $R^3$, $R^4$, $R^6$ and $X^1$ are the same as defined above; $R^{16}$ is a lower alkyl group; $R^{17}$ and $R^{18}$ are each a lower alkyl group, a cycloalkyl group, an unsubstituted phenyl-lower alkyl group or a substituted phenyl-lower alkyl group having halogen atoms, a lower alkylenedioxy group and/or lower alkyl groups as the substituents on the phenyl ring].

The reaction of a compound of the general formula (214) with a compound of the general formula (16) is carried out in a suitable solvent in the presence of a basic compound. As to the basic compound used in the reaction, sodium hydroxide, potassium hydroxide, sodium ethylate, sodium hydride, potassium hydride, sodium amide and potassium amide can be exemplified. As to the solvent, alcohols such as methanol, ethanol and isopropanol; ethers such as dioxane and diethylene glycol dimethyl ether; aromatic hydrocarbons such as benzene, toluene and xylene; aprotic polar solvents such as dimethylformamide, dimethyl sulfoxide and hexamethylphosphoric triamide can be exemplified. The amount of a compound of the general formula (16) is not specifically restricted and can be selected from a wide range, generally, at least an equimolar quantity, preferably an equimolar to 5 times the molar quantity thereof may be used to a compound of the general formula of (214). The reaction is generally carried out at about 0° to 70° C., preferably at about 0° C. to room temperature, and is completed in 0.5 to 12 hours.

The reaction of a compound of the general formula (215) in which $R^1$ and $R^2$ are hydrogen atoms with a compound of the general formula (17), and the reaction of a compound (216) with a compound of the general formula (16) can be carried out under conditions similar to those employed in the reaction of a compound of the general formula (214) with a compound of the general formula (16).

A compound of the general formula (218) can be prepared from a compund of the general formula (217) under conditions similar to those employed in the reaction for obtaining a compound of the general formula (212).

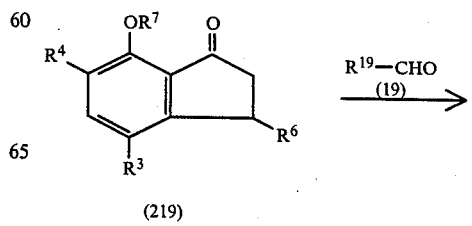

-continued
Reaction process formula - 15

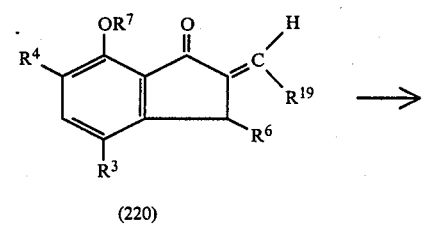

(220)

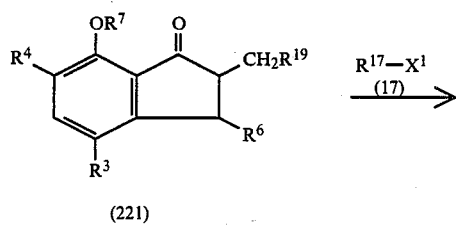

(221)

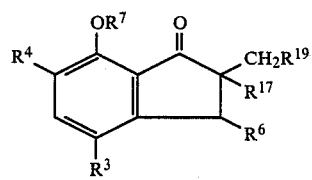

(221a)

[wherein $R^3$, $R^4$, $R^6$, $R^7$ and $R^{17}$ are same as defined above; $R^{19}$ is an unsubstituted phenyl-lower alkyl group or a substituted phenyl-lower alkyl group having halogen atoms and/or lower alkyl groups as the substituents on the phenyl ring].

The reaction of a compound of the general formula (219) with a compound of the general formula (19) can be carried out in a suitable solvent or without the solvent, in the presence of a basic compound. As to the solvent used in the reaction, any solvent which does not give adverse effect to the reaction can be used, for example water, alcohols such as methanol, ethanol and isopropanol; aromatic hydrocarbons such as benzene, toluene and xylene; ethers such as diethyl ether, tetrahydrofuran, dioxane, diglyme and monoalyme; halogenated hydrocarbons such as dichloromethane, chloroform and carbon tetrachloride; aprotic polar solvents such as dimethylformamide, dimethyl sulfoxide and hexamethylphosphoric triamide can be exemplified. As to the basic compound used in the reaction, inorganic basic compounds such as sodium hydroxide, potassium hydroxide, potassium carbonate, sodium carbonate, potassium bicarbonate, sodium bicarbonate and sodium hydride; metal alcoholates such as sodium ethylate and sodium methylate; organic basic compounds such as 1,5-diazabicyclo[4,3,0]non-5-ene (DBN), 1,8-diazabicyclo[5,4,0]undec-7-ene (DBU) and 1,4-diazabicyclo[2,2,2]octane (DABCO) and triethylamine can be exemplified.

The amount of a compound of the general formula (19) may be at least an equimolar, preferably an equimolar to 2 times the molar quantity thereof used to a compound of the general formula (219). As to the amount of the basic compound, at least an equimolar quantity, preferably an equimolar to 5 times the molar quantity thereof used to a compound of the general formula (219). The reaction is generally carried out at about 0° to 150° C., preferably at about room temperature to 100° C., and is completed in about 0.5 to 8 hours.

The reduction of a compound of the general formula (220) can be carried out under the conditions similar to those employed in the reduction of a compound of the general formula (101) in the above-mentioned Reaction process formula-1.

The reaction of a compound of the general formula (221) with a compound of the general formula (17) can be carried out under conditions similar to those employed in the reaction of a compound of the general formula (215) with a compound of the general formula (17), except the reaction temperature, that at generally about 0° to 90° C., preferably at about 0° to 60° C.

Reaction process formula - 16

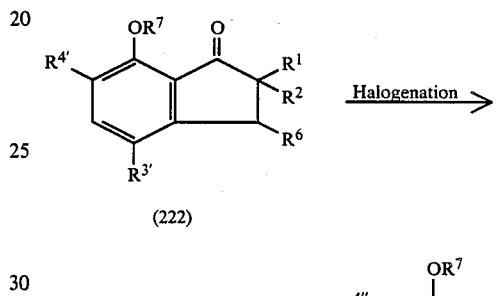

(222)

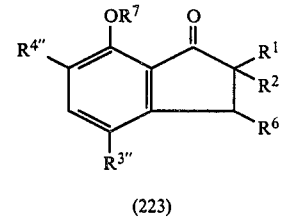

(223)

[wherein $R^1$, $R^2$, $R^6$ and $R^7$ are the same as defined above; $R^{3'}$ and $R^{3''}$ are the same as defined in $R^3$; $R^{4'}$ and $R^{4''}$ are the same as defined in $R^4$; provided that at least any one of $R^{3'}$ and $R^{4'}$ is a hydrogen atom, and at least any one of $R^{3''}$ and $R^{4''}$ is a halogen atom].

The halogenation of a compound of the general formula (222) can be carried out in a suitable solvent, in the presence of a usual halogenating agent. As to the halogenating agent, any one used can be applied, for example halogen molecule such as bromine and chlorine; iodine monochloride, sulfuryl chloride, N-halogenosuccinimides such as N-bromosuccinimide and N-chlorosuccinimide can be exemplified. The amount of halogenating agent may be generally an equimolar to 10 times the molar quantity, preferably an equimolar to 5 times the molar quantity thereof to a compound of the general formula (222). As to the solvent used in the halogenation, halogenated hydrocarbons such as dichloromethane, dichloroethane, chloroform and carbon tetrachloride; fatty acids such as acetic acid and propionic acid; and water can be exemplified. The halogenation is generally carried out at 0° C. to the boiling point of the solvent, preferably at about 0° to 40° C., and is completed in about 1 to 10 hours.

A compound of the general formula (211) being used as the starting material in the above-mentioned Reaction process formula - 13 can be prepared by a methode as shown in the following Reaction process formula - 17.

Reaction process formula - 17

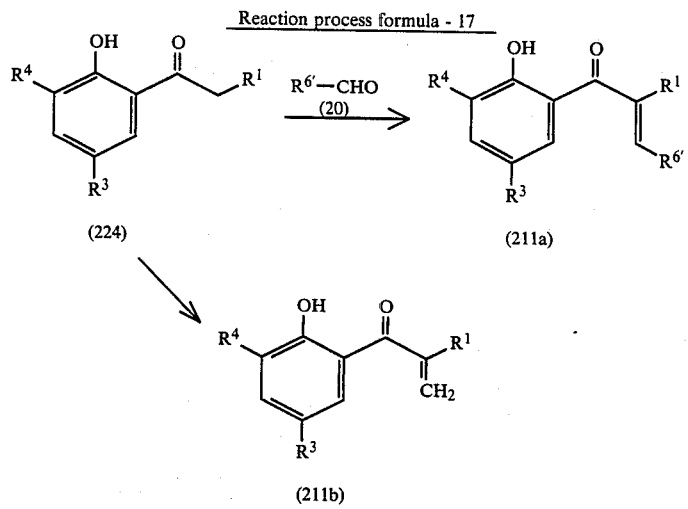

[wherein $R^1$, $R^3$ and $R^4$ are the same as defined above; and $R^{6''}$ is a phenyl group].

The reaction of a compound of the general formula (224) with a compound of the general formula (20) can be carried out under conditions similar to those employed in the reaction of a compound of the general formula (219) with a compound of the general formula (19).

Process for introducing a compound of the general formula (224) to a compound of the general formula (211b) can be conducted by the following methods.

(i) Method for reacting a compound of the general formula (224) with a compound of the general formula

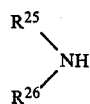

(wherein $R^{25}$ and $R^{26}$ are each a lower alkyl group) and with formaldehyde, which is called as "Mannich Reaction".

This reaction can be carried out in a suitable solvent in the presence of an acid. As to the solvent used in the reaction, any solvent which can be generally used in Mannich reaction can also be used, for example water, alcohols such as methanol, ethanol and isopropanol; alkanoic acids such as acetic acid and propionic acid; acid anhydrides such as acetic anhydride; polar solvents such as acetone and dimethylformamide; and mixed solvents thereof can be exemplified. As to the acid used in the reaction, mineral acids such as hydrochloric acid and hydrobromic acid; organic acids such as acetic acid can be exemplified. As to the formaldehyde used in the reaction, as aqueous solution of formaldehyde containing 20 to 40% by weight thereof, trimer of formaldehyde or paraformaldehyde can be used. The amount of a compound of the general formula

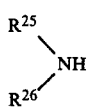

is at least an equimolar quantity, preferably an equimolar to 2 times the molar quantity may be used to a compound of the general formula (224). The amount of formaldehyde is at least as equimolar quantity, generally a large excess quantity may be used to a compound of the general formula (224). The reaction is generally carried out at about 0° to 200° C., preferably at about room temperature to 150° C., and is completed in 0.5 to 10 hours.

(ii) Method for reacting a compound of the general formula (224) with a compound of the general formula

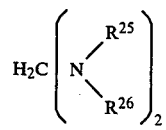

(wherein $R^{25}$ and $R^{26}$ are the same as defined above).

This reaction can be carried out in the presence of an acid in a suitable solvent or without the solvent. As to the acid used in the reaction, mineral acids such as sulfuric acid, hydrochloric acid and hydrobromic acid; organic acids such as acetic acid and acetic anhydride can be exemplified, preferably, acetic anhydride may be used. As to the solvent used in the reaction, any solvent which can be used in the above-mentioned Mannich reaction can also be used. The amount of a compound of the general formula

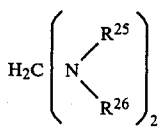

may be at least an equimolar quantity, preferably an equimolar to 5 times the molar quantity to the amount of a compound of the general formula (224). The reaction is carried out generally at 0° to 150° C., preferably at about room temperature to 100° C., and is completed in about 0.5 to 5 hours.

Reaction process formula - 18

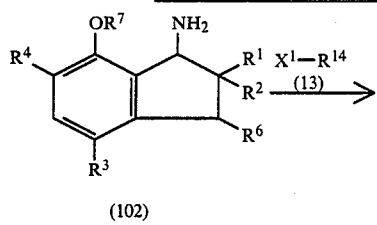

(102)

(110)

[wherein $R^1$, $R^3$, $R^4$, $R^6$, $R^7$ and $X^1$ are the same as defined above; $R^{14}$ is an alkyl group having 7 to 10 carbon atoms, a lower alkenyl group, a lower alkylamino-lower alkyl group, a phenyl-lower alkyl group, or a group of the formula —A″-B (wherein A″ is a lower alkylene group which may have hydroxyl groups as the substituents; B is the same as defined above)].

The reaction of a compound of the general formula (102) with a compound of the general formula (13) can be carried out under conditions similar to those employed in the reaction of a compound of the general formula (102) with a compound of the general formula (4) in the above-mentioned Reaction process formula - 2.

Reaction process formula - 19

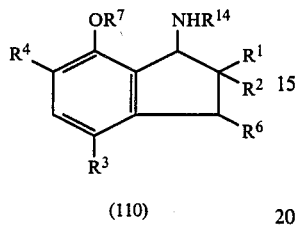

(2)

(111)

(112)

[wherein $R^1$, $R^2$, $R^3$, $R^4$ and $R^7$ are the same as defined above; $R^{15}$ is a lower alkenyl group, a lower alkylamino-lower alkyl group, a phenyl-lower alkyl group, a lower alkyl group having 7 to 10 carbon atoms].

The reaction of a compound of the general formula (2) with a compound of the general formula (14) is carried out in a suitable solvent or without the solvent, in the presence or absence of a dehydrating agent. As to the solvent used in the reaction, alcohols such as methanol, ethanol and isopropanol; aromatic hydrocarbons such as benzene, toluene xylene; halogenated hydrocarbons such as dichloromethane, dichloroethane, chloroform and carbon tetrachloride; aprotic polar solvents such as dimethylformamide, dimethylacetamide and N-methylpyrrolidone; and mixtures of these solvents can be exemplified. As to the dehydrating agent drying agents which can be used for dehydrating usual solvent such as molecular sieves, mineral acids such as hydrochloric acid, sulfuric acid and boron trifluoride; organic acids such as p-toluenesulfonic acid can be exemplified.

The reaction is generally carried out at room temperature to 250° C., preferably at about 50° to 200° C., and is completed generally in about 1 to 48 hours. The amount of a compound of the general formula (14) is not specifically restricted, and generally at least an equimolar quantity, preferably an equimolar to a large excess quantity thereof may be used to a compound of the general formula (2). As to the amount of the dehydrating agent, in case of using a drying agent a large excess quantity thereof may be used, and in case of using an acid a catalytic amount of acid may be used. A compound of the general formula (111) thus obtained is subjected to the next reducing reaction without isolated from the reaction system.

In carrying out the reducing reaction of a compound of the general formula (111), various methods can be applied, for example, the method for reducing a compound of the general formula (101) in the above-mentioned Reaction process formula-1 can be applied, preferably a method by using a hydrogenating reducing agent can be applied. As to the hydrogenating reducing agent, lithium aluminum hydride, sodium boron hydride and diborane can be exemplified. The amount of the hydrogenating reducing agent used in the reduction is at least an equimolar quantity, preferably an equimolar to 10 times the molar quantity thereof to a compound of the general formula (111). In the case of using lithium aluminum hydride as the reducing agent, 2 times the molar quantity thereof may advantageously be used to a compound of the general formula (111). This reducing reaction is generally carried out in a suitable solvent for example, water, lower alcohols such as methanol, ethanol and isopropanol; ethers such as tetrahydrofuran, diethyl ether and diglyme, and generally at about −60° to 50° C., preferably at about −30° C. to room temperature, for about 10 minutes to 5 hours. Furthermore, in the case of using lithium aluminum hydride or diborane as the reducing agent, an anhydrous solvent such as diethyl ether, tetrahydrofuran or diglyme may be used.

Reaction process formula - 20

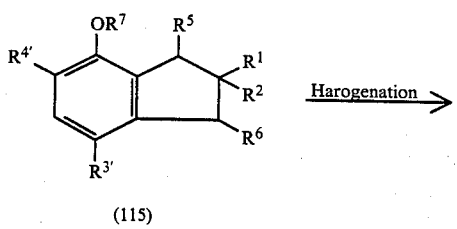

(115)

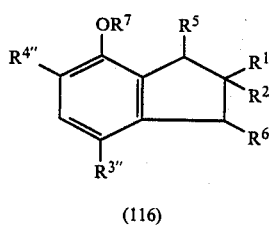

(116)

[wherein $R^1$, $R^2$, $R^5$, $R^6$, $R^{3'}$, $R^{4'}$, $R^{3''}$ and $R^{4''}$ are the same as defined above].

The halogenation of a comound of the general formula (115) can be carried out under conditions those empolyed in the halogenation of a compound of the general formula (222) in the above-mentioned Reaction process formula - 16.

Reaction process formula - 21

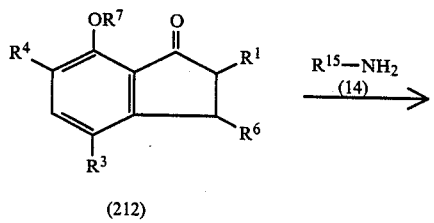

(212)

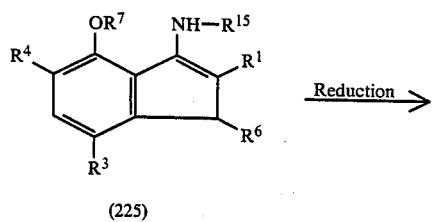

(225)

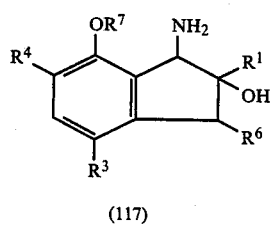

(117)

[wherein $R^1$, $R^3$, $R^4$, $R^6$, $R^7$ and $R^{15}$ are the same as defined above].

The reaction of a compound of the general formula (212) with a compound of the general formula (14) is carried out in a suitable solvent, in the presence of a dehydrating agent. As to the solvent used in the reaction, alcohols such as methanol, ethanol and isopropanol; aromatic hydrocarbons such as benzene, toluene and xylene; halogenated hydrocarbons such as dichloromethane, dichloroethane, chloroform and carbon tetrachloride; aprotic polar solvents such as dimethylformamide, dimethylacetamide and N-methylpyrrolidone, and mixtures of these solvents can be exemplified. As to the dehydrating agent, drying agents used for dehydrating usual solvents such as molecular sieves, mineral acids such as hydrochloric acid, sulfuric acid and boron trifluoride; organic acids such as p-toluenesulfonic acid can be exemplified. The reaction is generally carried out at about 0° to 150° C., preferably at about at room temperature to 100° C., and is completed in about 1 to 48 hours. The amount of a compound of the general formula (14) used in the reaction is not particularly restricted, and generally at least an equimolar quantity, preferably an equimolar to 2 times the molar quantity thereof may be used to a compound of the general formula (212). The amount of the dehydrating agent used in the reaction, in the case of using a drying agent as the dehydrating agent, generally a large excess amount thereof is used, and in the case of using an acid as the dehydrating agent, generally a catalytic amount thereof may be used.

The reducing reaction of a compound of the general formula (225) can be carried out under conditions similar to those employed in the reducing reaction of a compound of the general formula (101) in the above-mentioned Reaction process formula - 1. In some cases, when a compound of the general formula (225) wherein $R^{15}$ is a phenyl-lower alkyl group, a compound represented by the general formula (118)

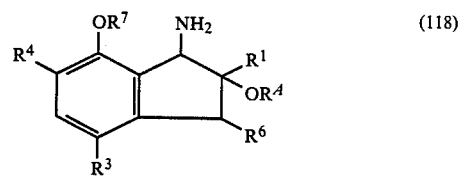

(118)

[wherein $R^4$ is a phenyl-lower alkyl group]. may also be obtained under the above-mentioned reducing conditions. The compound of the general formula (118) and a compound of the general formula (117) can easily be separated by usual separating means.

The desired products prepared in the above-mentioned various reaction process formulas can be isolated and purified by usual separation means, such as solvent extraction, dilution, recrystallization, column chloromatography, preparative thin-layer chromatography, etc.

The compounds of the present invention including inevitably their optical isomers.

2,3-Dihydro-1H-indene derivatives represented by the general formula can easily be converted into their acid-addition salts by reacting with pharmaceutically acceptable acids, and the present invention also including said acid-addition salts. As to the pharmaceutically acceptable acids, inorganic acids such as hydrochloric acid, hydrobromic acid, sulfuric acid, phosphoric acid; organic acids such as acetic acid, oxalic acid, succinic acid, maleic acid, fumaric acid, malic acid, tartaric acid, citric acid, malonic acid, methanesulfonic acid and benzoic acid can be exemplified and used.

2,3-Dihydro-1H-indene derivatives of the present invention and salts thereof can be used in any of usual preparations of pharmaceutical compositions together with usual pharmaceutically acceptable carriers. Examples of pharmaceutically acceptable carriers which are selected depend on the desired form of pharmaceutical compositions including diluents and excipients such as fillers, diluents, binders, wetting agents, disintegrating agents, surface active agents and lubricants, etc. No particular restriction is made to the administration unit forms and the pharmaceutical compositions can be selected from any desired unit form including tablets, pills, powders, liquors, suspensions, granules, capsules, suppositories, injection preparations (including solutions, suspensions, etc.), ointments, etc. For the purpose of shaping in the form of tablets, carriers which are widely used in this field can be used, for example excipients such as lactose, sucrose, sodium chloride, glucose, urea, starch, calcium carbonate, kaolin, crystalline cellulose and silicic acid; binding agents such as water, ethanol, propanol, simple sirup, glucose solutions, starch solutions, gelatin solutions, carboxymethyl cellulose, shelac, methyl cellulose, calcium phosphate and polyvinylpyrrolidone; disintegrating agents such as dried starch, sodium alginate, agar-agar powder, laminalia powder, sodium bicarbonate, calcium carbonate, esters of polyoxyethylene sorbitan fatty acids, sodium laurylsulfate, monoglyceride of stearic acid, starch and lactose, etc.; disintegration inhibitors such as sucrose, stearine, coconut butter and hydrogenated oils; absorption accelerators such as quaternary ammonium bases and sodium laurylsulfonate; wetting agents such as glycerin and starch; adsorbing agents such as starch, lactose, kaolin, bentonite and colloidal silicic acid; and lubricants such as purified talc, stearic acid salts, boric acid powder and polyethylene glycols can be exemplified.

If necessary, the tablets can further be coated with usual coating materials to make them into coated tablets, for example tablets coated with sugar, tablets coated with gelatin film, tablets coated with enteric coating layers, tablets coated with films or double layer tablets as well as multiple layer tablets.

For the purpose of shaping in the form of pills, any carrier which is known and used widely in this field can be used, for example, excipients such as glucose, lactose, starch, coconut butter, hydrogenated vegetable oils, kaolin, and talc, etc.; binding agents such as powdered arabic gum, powdered tragacnthe gum, geletin and ethanol, etc; disintegrating agents such as laminarial and agar-agar, etc. can be exemplified.

For the purpose of shaping in the form of suppositories, carriers which are known and widely used in this field can also be used, for example polyethylene glycols, coconut butter, higher alcohols, esters of higher alcohols, geletin and semi-synthesized glycerides, etc. can be exemplified.

For the purpose of making in the form of injection preparations, solutions and suspensions prepared are further sterilized and are preferably isotonic to the blood. In preparing the injection preparations in the form of solutions, emulsions and suspensions, any carrier which is known and is widely used in this field can also be used, for example water, ethanol, prorylene glycol, ethoxylated isostearyl alcohol, polyoxylated isostearyl alcohol and polyoxyethylene sorbitan fatty acid esters, etc. In these instances, adequate amounts of sodium chloride, glucose or glycerin may be added to the desired injection preparation to make them isotonic. Furthermore, usual dissolving agents, buffer agents, analgesic agents may be added. Also coloring materials, preservatives, perfumes, seasoning agents, sweetening agents and other medicines may be added in the desired pharmaceutical preparations, if necessary.

For the purpose of making the preparations in the form of pastes, creams and gels, diluents which are known and used widely in this field can also be used, for example white petrolatum, paraffin, glycerin, cellulose derivatives, polyethylene glycols, silicons, bentonite, etc. can be exemplified.

The amount of 2,3-dihydro-1H-indene derivatives and their salts represented by the general formula (1) to be contained in pharmaceutical compositions is not specifically restricted, and can be suitably be selected from a wide range, and generally 1 to 70% by weight thereof is contained in the compositions.

Methods for administering the above-mentioned pharmaceutical compositions are not specifically restricted, the compositions can be used in various forms of preparations depending upon the age of the patient, the distinction of sex, the degree of symptoms and other conditions of the patient, without any restriction. For example, tablets, pills, solutions, suspensions, emulsions, granules and capsules are administered orally. Injection preparations are administered intraveneously singly, or administered with usual injectable transfusions such as glucose solutions, amino acids solutions, etc.; and further, if necessary, the injection preparations are administered singly intramuscularly, intracutaneously, subcutaneously or intraperitoneally. Suppositories are administered into rectum.

The dosage of the above-mentioned pharmaceutical preparations can be selected suitable according to the methods for administrations, the age of the patient, the distinction of sex and other conditions as well as the degree of the symptoms, and generally pharmaceutical compositions containing 0.2 to 200 mg per kg of the body weight per day of the 2,3-dihydro-1H-indene derivative or its acid-addition salt represented by the general formula (1) may be used.

The present invention is now illustrated by referring to the following examples, in which the preparations of the starting materials are explained in Reference Examples, further the preparations of the objective 2,3-dihydro-1H-indene derivatives are explained in Examples. However, the present invention is not restricted only to these examples.

REFERENCE EXAMPLE 1

A mixture of 196 g of 2,3-dihydro-7-hydroxy-4-methyl-1H-inden-1-one, 80 g of potassium hydroxide and 2.5 liters of methanol was refluxed for 30 minutes. Then the reaction mixture was cooled to room temperature, then 250 g of cinnamyl bromide was added dropwise to the reaction mixture under vigorous stirring condition. The reaction mixture was further stirred for 8 hours at the same temperature, then the crystals separated therein were collected by filtration, washed with cold methanol and dried. Recrystallized from ethanol to yield 126 g of 7-cinammyloxy-2,3-dihydro-4-methyl-1H-inden-1-one. Colorless needle-like crystals. Melting point: 110°–111° C.

REFERENCE EXAMPLE 2

A mixture of 7 g of 7-cinammyloxy-2,3-dihydro-4-methyl-1H-inden-1-one and 40 ml of tetrahydronaphthalene was refluxed for 3 hours under nitrogen gas stream. After the reaction was completed, the reaction mixture was cooled to room temperature, then was purified by a silica gel column chromatography (eluent:

n-hexane:ethyl acetate=10:1). Recrystallized from ethanol to yield 2.64 g of 2,3-dihydro-7-hydroxy-4-methyl-6-(1-phenyl-2-propenyl)-1H-inden-1-one. Colorless flake-like crystals. Melting point: 131°–131.5° C.

REFERENCE EXAMPLE 3

16.2 Grams of 7-hydroxy-4,6-dimethyl-1-indane oxime was dissolved in 200 ml of acetic acid, then 1.0 g of platinum oxide catalyst was added thereto, and the whole mixture was catalytically reduced under 5 atmospheric hydrogen gas pressure at room temperature for 8 hours. After the reaction was completed, the catalyst was removed by filtration, then the filtrate was concentrated to dryness under a reduced pressure. The residue thus obtained was dissolved in 200 ml of ethanol, then hydrogen chloride gas was saturated in this solution by blowing. The solution was concentrated to dryness by removing the solvent under a reduced pressure to yield 3.40 g of 1-amino-2,3-dihydro-7-hydroxy-4,6-dimethyl-1H-indene hydrochloride in the form of colorless needle-like crystals. Melting point: 229°–230° C. (Decomposed)

REFERENCE EXAMPLES 4–5

By a method similar to that described in reference Examples 3, and by using suitable starting materials, there were prepared compounds as follows.

| Reference Example No. | Name of Compound |
|---|---|
| 4 | 1-Amino-2,3-dihydro-7-hydroxy-4-methyl-6-sec-butyl-1H—indene hydrochloride Colorless powdery crystals (Recrystallized from methanol-diethyl ether) Melting point: 177.5–179° C. |
| 5 | 1-Amino-2,3-dihydro-7-hydroxy-2,2,4,6-tetramethyl-1H—indene hydrochloride Colorless needle-like crystals (Recrystallized from ethanol) Melting point: 231–233° C. |

REFERENCE EXAMPLE 6

A solution containing 17.7 g of 1-amino-4,6-dimethyl-7-hydroxy-2,3-dihydro-1H-indene and 15.2 g of triethylamine in 200 ml of chloroform was ice-cooled under stirring condition, then 13.56 g of chloroacetyl chloride was added dropwise thereto. After the dropwise addition was finished, the reaction mixture was stirred at 25° C. for 3 hours. After the reaction was completed, the reaction mixture was washed with 100 ml of 1N-hydrochloric acid aqueous solution, further washed three times with 100 ml of water, then dried with anhydrous magnesium sulfate, and the solvent was removed by evaporation under a reduced pressure. Recrystallized from ethanol to obtain 21 g of 1-chloroacetylamino-2,3-dihydro-4,6-dimethyl-7-hydroxy-1H-indene. Colorless needle-like crystals. Melting point: 131°–132° C.

REFERENCE EXAMPLES 7–9

By a method similar to that described in Reference Example 6, and by using suitable starting materials, there were prepared compounds of Reference Examples 7–9 shown in Table 1 as follows.

TABLE 1

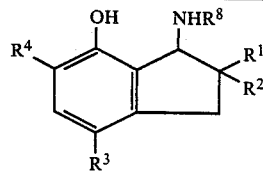

| Reference Example No. | $R^1$ | $R^2$ | $R^3$ | $R^4$ | $R^8$ | Crystal form (Recrystallization solvent) | Melting point (°C.) |
|---|---|---|---|---|---|---|---|
| 7 | $CH_3$ | $CH_3$ | $CH_3$ | $CH_3$ | $-COCH_2Cl$ | Colorless needle-like crystals (Ethanol) | 200–201 |
| 8 | H | H | $CH_3$ | $-CHCH_3$<br>$\|$<br>$C_2H_5$ | $-COCH_2Cl$ | Colorless needle-like crystals (Ethanol) | 111.5–114.5 |
| 9 | $CH_3$ | $CH_3$ | $CH_3$ | $-CHCH_3$<br>$\|$<br>$C_2H_5$ | $-COCH_2Cl$ | Colorless needle-like crystals (Ethanol) | 158–160 |

REFERENCE EXAMPLE 10

2.00 Grams of (3-methoxyphenyl)piperazine was dissolved in 20 ml of chloroform, then 1.40 ml of triethylamine was added to this solution, further 0.92 ml of chloroacetyl chloride was added dropwise gradually thereto at 0° C., after the dropwise addition was finished, the reaction mixture was further stirred at the same temperature for 30 minutes. After the reaction was completed, the reaction mixture was washed with water, and was dried with anhydrous magnesium sulfate. The solvent was removed by evaporation to obtain 3.2 g of 1-chloroacetyl-4-(3-methoxyphenyl)piperazine in the form of an oily substance.

REFERENCE EXAMPLE 11

To a mixture of 1.50 g of 4-(3-chlorophenyl)piperazine and 0.31 g of sodium hydride was added 2.4 ml of epichlorohydrin and the reaction mixture was stirred at room temperature for 30 minutes. After the reaction was completed, the reaction mixture was extracted with 100 ml of ethyl acetate, and the extract was washed 5 times with 100 ml of water, then dried with anhydrous magnesium sulfate. The solvent was removed by evaporation to obtain the residue which was purified by means of a silica gel column chromatography (eluent-:ethyl acetate:n-hexane=1:1) to obtain 1.66 g of 4-(3- chlorophenyl)-1-(2,3-epoxypropyl)piperazine as in the form of an oily substance.

REFERENCE EXAMPLE 12

10 Grams of 2,4-dimethylphenyl cinnamate was melted at 80° C., then under stirring condition, 7.93 g of finely pulverized aluminium chloride was added thereto, and stirred at the same temperature for 10 minutes. 100 Grams of ice was added to the reaction mixture and extracted with 200 ml of methylene chloride. The extract was washed with water, dried then concentrated under a reduced pressure. The residue thus obtained was purified by means of a silica gel column chromatography (eluent:chloroform:n-hexane=1:1), then the purified product was recrystallized from ethanol to obtain 2.89 g of 2,3-dihydro-7-hydroxy-3-phenyl-1H-inden-1-one. Light yellow powdery crystals. Melting point: 137°–138° C.

REFERENCE EXAMPLE 13

212.6 Grams of 4,6-dimethyl-2-(2-phenylacetyl)phenol was dissolved in 350 ml of N,N,N',N'-tetramethyldiaminomethane, then under ice-cooled condition with stirring, 350 ml of acetic anhydride was added dropwise thereto. The reaction mixture was further stirred at room temperature for 2 hours, then was poured in 1 kg of ice and stirred vigorously. The crystals separated in the mixture were collected by filtration, washes with water, then dried. Recrystallized from ethanol to obtain 186 g of 2,4-dimethyl-6-(2-phenylacryloyl)phenol. Colorless needle-like crystals. Melting point: 83°–84° C.

REFERENCE EXAMPLE 14

Into 15 ml of concentrated sulfuric acid, under ice-cooled condition with stirring, 3.0 g of 2,4-dimethyl-6-(2-phenylacryloyl)phenol was added gradually, then the whole mixture was stirred at room temperature for 1 hour. The reaction mixture was poured in 100 g of ice and extracted with 200 ml of methylene chloride. The extract was washed with water and dried with anhydrous magnesium sulfate, then was concentrated under a reduced pressure to obtain the residue. The residue was recrystallized from ethanol to obtain 2.11 g of 2,3-dihydro-4,6-dimethyl-2-phenyl-7-hydroxy-1H-inden-1-one.

Colorless prism-like crystals. Melting point: 90.5°–91° C.

NMR (CDCl$_3$) δ: 9.03 (s, 1H), 7.42–7.08 (m, 6H), 3.92 (d-d, 1H, J=8.4 Hz, 3.6 Hz), 3.52 (d-d, 1H, J=16.8 Hz, 8.4 Hz), 3.02 (d-d, 1H, J=16.8 Hz, 3.6 Hz), 2.23 (s, 6H)

REFERENCE EXAMPLES 15–20

By a method similar to that described in REFERENCE EXAMPLE 14, by using a suitable starting material, there were prepared compounds of Reference Examples 15–20 as shown in Table 2 as follows.

TABLE 2

[Structure: indanone core with substituents OR$^7$, R$^4$, R$^3$ on aromatic ring and R$^1$, R$^2$, R$^6$ on cyclopentanone ring]

| Reference Example No. | R$^1$ | R$^2$ | R$^3$ | R$^4$ | R$^6$ | R$^7$ | Crystal form (Recrystallization solvent) | Melting point (°C.) |
|---|---|---|---|---|---|---|---|---|
| 15 | 2-methylphenyl | H | CH$_3$ | CH$_3$ | H | H | Light brown needle-like crystals (Ethanol-water) | 118–120 |
| 16 | 4-chlorophenyl | H | CH$_3$ | CH$_3$ | H | H | Colorless Powdery crystals (Ethanol) | 89–90 |
| 17 | 2-chlorophenyl | H | CH$_3$ | CH$_3$ | H | H | Light brown powdery crystals (Ethanol) | 92–93 |
| 18 | CH$_3$ | CH$_3$ | CH$_3$ | 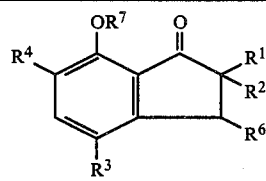 (2-chlorobenzoyl) | H | H | Colorless needle-like crystals (Ethanol) | 192–193 |
| 19 | phenyl | CH$_3$ | CH$_3$ | CH$_3$ | H | H | Light yellow granular crystals (Ethanol) | 93–94 |

TABLE 2-continued

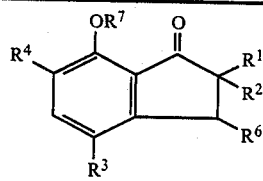

| Reference Example No. | R¹ | R² | R³ | R⁴ | R⁶ | R⁷ | Crystal form (Recrystallization solvent) | Melting point (°C.) |
|---|---|---|---|---|---|---|---|---|
| 20 | (phenyl) | H | Cl | CH₃ | H | H | Colorless powdery crystals (Ethanol) | 107–109 |

REFERENCE EXAMPLE 21

To a mixture of 140 g of 2'-methoxy-5'-methylpropiophenone, 83.4 g of benzaldehyde and 1.5 liters of ethanol was added 154 ml of 20%-sodium hydroxide aqueous solution under stirring. The reaction mixture was stirred overnight at room temperature, then 10%-hydrochloric acid was added to make the reaction mixture acidic, and extracted with benzene. The benzene extract was washed with water and an aqueous solution saturated with sodium chloride in this order, then dried to obtain 212 g of 2'-methoxy-5'-methyl-2-benzylidenepropiophenone. Yellow oily substance.

NMR (CDCl₃) δ: 2.20 (s, 3H), 2.30 (s, 3H), 3.73 (s, 3H), 6.81 (d, 2H, J=7 Hz), 7.00–7.60 (m, 8H).

REFERENCE EXAMPLE 22

To 210 g of 2'-methoxy-5'-methyl-2-benzylidenepropiophneone was added 1 kg of trifluoroacetic acid, and the mixture was refluxed for 10 hours under stirring condition. After the reaction was completed, the reaction mixture was concentrated and extracted with methylene chloride. The extract was washed with an aqueous solution saturated with sodium bicarbonate, water and an aqueous solution saturated with sodium chloride in this order, then dried and concentrated. Recrystallized from benzene to obtain 40 g of 2,3-dihydro-2,4-dimethyl-3-phenyl-7-methoxy-1H-inden-1-one as in the form of a mixture of cis-form and trans-form of 2- and 3-positions in the indene skeleton (hereinafter referred to as cis-trans mixture).

cis-Isomer: NMR (CDCl₃) δ: 0.81 (d, J=7Hz, 3H), 1.95 (s, 3H), 300 (d, q, 1H, J=7Hz), 3.95 (s, 3H), 4.57 (d, 1H, J=7Hz), 6.70–7.47 (m, 7H)

trans-Isomer: NMR (CDCl₃) δ: 1.34 (d, J=7Hz, 3H), 1.84 (s, 3H), 2.50 (d, q, 1H, J=4Hz, J-7Hz), 3.90–4.07 (m, 4H), 6.70–7.47 (m, 7H).

REFERENCE EXAMPLE 23

A solution of 19.6 g of 2,3-dihydro-2,4-dimethyl-3-phenyl-7-methoxy-1H-inden-1-one, 11.5 g of sodium iodide and 10.3 g of aluminium chloride in 200 ml of acetonitrile was stirred at room temperature for 2 hours. After the reaction was completed, the reaction mixture was poured in water, and was extracted with dichloromethane. The extract was once filtered through Celite (a trademark for diatomaceous earth, manufactured by Johns-Manville Products Corp., Celite Division, Manville, N.J., U.S.A.) and washed with an aqueous solution of sodium bicarbonate and with an aqueous solution saturated with sodiun chloride. After dried the extract, it was concentrated and the residue obtained was purified by means of a silica gel column chromatography. Recrystallized from n-hexane to obtain 11.4 g of cis-trans mixture of 2,3-dihydro-2,4-dimethyl-3-phenyl-7-hydroxy-1H-inden-1-one. Colorless prism-like crystals.

cis-Isomer: NMR (CDCl₃) δ: 0.81 (d, 3H, J=7Hz), 1.89 (s, 3H), 3.08 (d, q, 1H, J=7Hz), 4.61 (d, 1H, J=7Hz), 6.57–7.47 (m, 7H), 8.94 (s, 1H).

trans-Isomer: NMR (CDCl₃) δ: 1.37 (d, 3H, J=7Hz), 1.80 (s, 3H), 2.58 (d, q, J=4Hz, 7Hz), 3.98 (d, J=7Hz, 1H), 6.57–7.47 (m, 7H), 9.04 (s, 1H).

REFERENCE EXAMPLE 24

A solution of 19.0 g of 2,3-dihydro-2,4-dimethyl-3-phneyl-7-hydroxy-1H-inden-1-one, 13.98 g of crotyl bromide and 5.47 g of postassium hydroxide in 200 ml of acetone was heated and refluxed under stirring condition. After the reaction was completed, the reaction mixture was concentrated and extracted with ethyl acetate, then the extract was washed with water and with an aqueous solution saturated with sodium chloride, then dried. The extract was concentrated by removing the solvent under a reduced pressure, then recrystallized from methanol to obtain 11.8 g of 2,3-dihydro-2,4-dimethyl-3-phenyl-7-crotyloxy-1H-inden-1-one as in the form of cis-trans mixture. Colorless stick-like crystals. Melting point: 138.5°–139.5° C.

cis-Isomer: NMR (CDCl₃) δ: 0.78 (d, 3H, J=7Hz), 1.66–1.78 (m, 3H), 1.93 (s, 3H), 2.98 (d, q, 1H, J=7Hz), 4.70–4.83 (m, 2H), 5.56–6.20 (m, 2H), 6.67–7.43 (m, 7H)

trans-Isomer: NMR (CDCl₃) δ: 1.67 (d, 3H, J=7Hz), 1.66–1.78 (m, 3H), 1.82 (s, 3H), 2.48 (d, q, 1H, J=4Hz, 7Hz), 4.53–4.67 (m, 2H), 5.56–6.20 (m, 2H), 6.67–7.43 (m, 7H).

REFERENCE EXAMPLE 25

11 Grams of 2,3-dihydro-2,4-dimethyl-3-phenyl-4-methyl-7-crotyloxy-1H-inden-1-one was added to 55 ml of tetrahydronaphthalene and the mixture was heated and refluxed for 6 hours with stirring condition. After the reaction was completed, the reaction mixture was concentrated by removal of the solvent, and the residue thus obtained was purified by means of a silica gel column chromatography. 11.2 Grams of 2,3-dihydro-2,4-dimethyl-3-phenyl-6-(1-buten-3-yl)-7-hydroxy-1H-inden-1-one was obtained as cis-trans mixture. Yellow oily substance.

cis-Isomer: NMR (CDCl₃) δ: 0.80 (d, 3H, J=7Hz), 1.36 (d, 3H, J=8Hz), 1.87 (s, 3H), 3.10 (d, q, 1H, J=7Hz), 3.70–4.06 (m, 1H), 4.57 (d, 1H, J=7Hz), 4.93–5.23 (m, 2H), 5.80–6.26 (m, 1H), 6.66–7.43 (m, 6H), 9.23 (s, 1H).

trans-Isomer NMR (CDCl$_3$) δ: 1.34 (d, 3H, J=7Hz), 1.36 (d, 3H, J=8Hz), 1.80 (s, 3H), 2.58 (d, q, 1H, J=4Hz, 7Hz), 3.94 (d, 1H, J=4Hz), 3.70–4.06 (m, 1H), 4.93–5.23 (m, 2H), 5.80–6.26 (m, 1H), 6.66–7.43 (m, 6H), 9.33 (s, 1H).

REFERENCE EXAMPLE 26

10 Grams of 2,3-dihydro-4,6-dimethyl-7-hydroxy-1H-inden-1-one was dissolved in 200 ml of dimethylformamide, then 5.45 g of 60%-sodium hydride was added gradually thereto and the reaction mixture was stirred at room temperature for 30 minutes. Next, 6.91 ml of p-anisaldehyde was added to the reaction mixture and further stirred at room temperature for 1 hour. The reaction mixture was poured into 500 ml of ice-water, then acidified by adding hydrochloric acid, and the crystals formed were collected by filtration. The crystals were washed with water and with n-hexane and dried. Recrystallized from ethanol to obtain 16.09 g of 2,3-dihydro-4,6-dimethyl-7-hydroxy-2-(4-methoxybenzylidene)-1H-inden-1-one. Yellow needle-like crystals. Melting point: 192°–193° C.

REFERENCE EXAMPLE 27

16.09 Grams of 2,3-dihydro-4,6-dimethyl-7-hydroxy-2-(4-methoxybenzylidene)-1H-inden-1-one was dissolved in a mixed solvent of 150 ml of ethyl acetate with 100 ml of acetic acid, this solution was let subjected to catalytic reduction at room temperature under 3 atmospheric hydrogen gas pressure in the presence of 1.5 g of palladium black as the hydrogenation catalyst. After the catalytic reduction, the catalyst was removed by filtration, and the filtrate was concentrated by removing the solvent under reduced pressure. The residue thus obtained was purified by a silica gel column chromatography (eluent: n-hexane: ethyl acetate =9:1) to obtain 8.5 g of 2,3-dihydro-4,6-dimethyl-7-hydroxy-2-(4-methoxybenzyl)-1H-inden-1-one as in the form of colorless oily substance.

NMR (CDCl$_3$) δ: 2.12 (s, 3H), 2.18 (s, 3H), 2.40–3.40 (m, 5H), 3.76 (s, 3H) 6.81 (d, 2H, J=8Hz), 7.09 (s, 1H), 7.11 (d, 2H, J=8Hz), 9.03 (s, 1H).

REFERENCE EXAMPLES 28–30

By a method similar to that described in Reference Example 27 and by using suitable starting material, there were prepared compounds of References Examples 28–30 as follows.

| Reference Example No. | Name of compound |
|---|---|
| 28 | 2,3-Dihydro-4,6-dimethyl-y-hydroxy-2-benzyl-1H—inden-1-one<br>Colorless prism-like crystals (from ethanol)<br>Melting point: 107–108° C.<br>NMR (CDCl$_3$) δ: 2.11 (s, 3H), 2.19 (s, 3H), 2.40–3.50 (m, 5H), 7.13 (s, 1H), 7.25 (m, 5H), 9.04 (s, 1H). |
| 29 | 2,3-Dihydro-4,6-dimethyl-7-hydroxy-2-(4-chlorobenzyl)-1H—inden-1-one<br>Colorless prism-like crystals (from n-hexane) Melting point: 108–109° C.<br>NMR (CDCl$_3$) δ: 2.12 (s, 3H), 2.19 (s, 3H), 2.20–3.40 (m, 5H), 7.09 (s, 1H), 7.10–7.40 (m, 4H), 8.70–9.30 (broad, s, 1H). |
| 30 | 2,3-Dihydro-4,6-dimethyl-7-hydroxy-2-(3,4-methylenedioxybenzyl)-1H—inden-1-one<br>Colorless prism-like crystals (from ethanol)<br>Melting point: 108–109° C.<br>NMR (CDCl$_3$) δ: 2.17 (s, 3H), 2.21 (s, 3H), 2.40–3.40 (m, 5H), 5.90 (s, 2H), 6.71 (m, 3H), 7.13 (s, 1H), 9.04 (s, 1H). |

REFERENCE EXAMPLES 31–33

By a method similar to that described in Reference Example 26, by using suitable starting materials, there were prepared compounds of REFERENCE EXAMPLEs 31–33 as follows.

| Reference Example No. | Name of compound |
|---|---|
| 31 | 2,3-Dihydro-4,6-dimethyl-7-hydroxy-2-benzylidene-1H—inden-1-one<br>Light yellow prism-like crystals (from ethanol) Melting point: 161–162° C.<br>NMR (CDCl$_3$) δ: 2.18 (s, 3H), 2.22 (s, 3H), 3.71 (sm 2H), 7.08 (s, 1H), 7.30–7.70 (m, 5H), 9.23 (s, 1H). |
| 32 | 2,3-Dihydro-4,6-dimethyl-7-hydroxy-2-(4-chlorobenzylidene)-1H—inden-1-one<br>Light yellow needle-like crystals (from ethanol) Melting point: 184–185° C.<br>NMR (CDCl$_3$) δ: 2.19 (s, 3H), 2.23 (s, 3H), 3.69 (s, 2H), 7.10 (s, 1H), 7.30–7.60 (m, 4H), 9.20 (s, 1H). |
| 33 | 2,3-Dihydro-4,6-dimethyl-7-hydroxy-2-(3,4-methylenedioxybenzylidene)-1H—inden-1-one<br>Light yellow needle-like crystals (from ethanol) Melting point: 243–244° C.<br>NMR (DMSO-d$_6$) δ: 2.18 (s, 3H), 2.30 (s, 3H), 3.90 (s, 2H), 6.10 (s, 2H), 7.02 (d, J=9 Hz, 1H), 7.25 (s, 1H), 7.28 (d, 1H, J=2 Hz), 7.36 (d-d, 1H, J=9 Hz, 2 Hz). |

REFERENCE EXAMPLE 34

28.3 Grams of 2,3-dihydro-4,6-dimethyl-7-hydroxy-2-benzyl-1H-inden-1-one was dissolved in 350 ml of dimethylformamide, then 5.2 g of 60%-sodium hydride was added thereto at 55°–60° C. and the mixture was stirred for 40 minutes. Next 8 ml of methyl iodide was added thereto, and the whole mixture was heated to the same temperature for 1 hour. Followed by 5.2 g of 60%-sodium hydride was added and stirred for 40 minutes at the same temperature. Next, 8 ml of methyl iodide was further added and heated for 10 minutes at the same temperature. Furthermore, 5.2 g of 60%-sodium hydride was added to the reaction mixture and stirred for 55 minutes at the same temperature, and 8 ml of methyl iodide was added to the reaction mixture and heated to the same temperature for 3 hours and 20 minutes. After the reaction was completed, dimethylformamide was removed under a reduced pressure and the residue obtained was extracted with ethyl acetate. The extract was washed with water and with an aqueous solution saturated with sodium chloride in this order, then the solvent was removed under a reduced pressure to obtain the residue. The residue was purified by means of a silica gel column chromtagraphy (eluent: n-hexane: ethyl acetate) to obtain 23.0 g of 2,3-dihydro-2,4,6-trimethyl-7-methoxy-2-benzyl-1H-inden-1-one.

NMR (CDCl₃) δ: 1.25 (s, 3H), 2.14 (s, 3H), 2.21 (s, 3H), 2.30–3.20 (m, 4H), 3.91 (s, 3H), 7.15 (m, 5H), 7.23 (s, 1H).

REFERENCE EXAMPLE 35

23.0 Grams of 2,3-dihydro-2,4,6-trimethyl-7-methoxy-2-benzyl-1H-inden-1-one and 25.8 g of sodium iodide were dissolved in 90 ml of acetonitrile. To this solution was added 22.9 g of aluminium chloride at room temperature and stirred for 1 hour. Then the solvent was removed by evaporation under a reduced pressure, and the residue thus obtained was extracted with ethyl acetate. The extract was washed with an aqueous solution saturated with sodium chloride, an aqueous solution of sodium thiosulfate and an aqueous solution saturated with sodium chloride in this order, and the insoluble matters were removed by filtration. The solvent was removed by evaporation and the residue thus obtained was recrystallized from n-hexane to obtain 19.7 g of 2,3-dihydro-2,4,6-trimethyl-7-hydroxy-2-benzyl-1H-indene-1-one. Colorless prism-like crystals.

Melting point: 86°–87° C.

NMR (CDCl₃) δ: 1.22 (s, 3H), 2.08 (s, 3H) 2.15 (s, 3H), 2.30–3.20 (m, 4H), 7.02 (s, 1H), 7.08–7.40 (m, 5H), 9.03 (s, 1H).

REFERENCE EXAMPLE 36

5.0 Grams of 4,6-dimethyl-7-hydroxy-2-phenyl-1-indanone was dissolved in 10 ml of diethyl ether and 10 ml of dichloromethane, then this solution was added dropwise gradually to a mixture of a solution of 2.55 ml of benzylamine in 10 ml of diethyl ether with 8 g of Molecular sieves 5A. The whole mixture was stirred at room temperature for 2 days and filtered by using Celite to obtain filtrate. The Celite used was washed with dichloromethane and ethanol, then these washing liquors were combihed with the above-mentioned filtrate and concentrated. Recrystallized from dichloromethane-ethanol to obtain 3.83 g of 4,6-dimethyl-7-hydroxy-1-benzylamino-2-phenyl-3H-indene. Orange needle-like crystals.

Melting point: 214°–215° C.

EXAMPLE 1

An ethanol solution containing 120 g of 2,3-dihydro-7-hydroxy-4-methyl-6-(1-phenyl-2-propenyl)-1H-inden-1-one, 45 of hydroxylamine hydrochloride and 200 ml of pyridine in 1,200 ml of ethanol was refluxed for 4 hours. After the reaction was completed, the reaction mixture was concentrated to dryness under a reduced pressure, then the residue thus obtained was dissolved in 2 liters of ethyl acetate and washed three times with 1 liter of water each time, and the residue was dried again under a reduced pressure. Recrystallized from ethyl acetate/n-hexane mixture to obtain 90 g of 2,3-dihydro-7-hydroxy-4-methyl-6-(1-phenyl-2-propenyl)-1H-inden-1-one oxime. Light yellow flake-like crystals. Melting point: 146° C. (Decomposed).

EXAMPLES 2-21

By a method similar to that described in Example 1, and by using a suitable starting material, there were prepared compounds of Examples 2–21 shown in Table 3 as follows.

TABLE 3

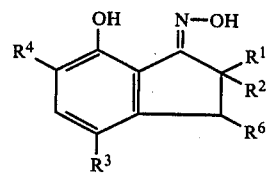

| Example No. | R¹ | R² | R³ | R⁴ | R⁶ | Crystal form (Recrystallization solvent) | Melting point (°C.) |
|---|---|---|---|---|---|---|---|
| 2 | H | H | CH₃ | —NHCCH₂N⁺(pyridinium).Cl⁻ (O=) | H | Colorless flake-like crystals (Water) | 279 (decomposed) |
| 3 | H | H | CH₃ | —CH(C₂H₅)—C₆H₅ | H | Colorless powdery crystals (Ethanol-diethyl ether) | 187.5–189.5 |
| 4 | —C₆H₄—Cl | H | CH₃ | CH₃ | H | Orange granular crystals (Ethanol) | 190–191 (decomposed) |
| 5 | —C₆H₅ | H | CH₃ | CH₃ | H | Colorless prism-like crystals (Ethanol) | 173–175 |

TABLE 3-continued $$\text{structure: indanone oxime with } R^1, R^2, R^3, R^4, R^6 \text{ substituents; 7-OH, 1-position =N-OH}$$

| Example No. | $R^1$ | $R^2$ | $R^3$ | $R^4$ | $R^6$ | Crystal form (Recrystallization solvent) | Melting point (°C.) |
|---|---|---|---|---|---|---|---|
| 6 | H | H | $CH_3$ | $CH_3$ | phenyl | Colorless powdery crystals (Ethanol) | 156.5–158 |
| 7 | $CH_3$ | H | $CH_3$ | $-CHCH=CH_2$ <br> $\quad\|$ <br> $\quad CH_3$ | phenyl | Colorless flake-like crystals (n-Hexane) | 121.5–124 |
| 8 | 4-methylphenyl | H | $CH_3$ | $CH_3$ | H | Light yellow needle-like crystals (Ethanol-water) | 156–158 |
| 9 | 2-methylphenyl | H | $CH_3$ | $CH_3$ | H | Light yellow needle-like crystals (Ethanol-water) | 175–177 |
| 10 | 2-chlorophenyl | H | $CH_3$ | $CH_3$ | H | Colorless powdery crystals (Ethanol-water) | 182–183 |
| 11 | $CH_3$ | $CH_3$ | $CH_3$ | 2-chlorobenzoyl | H | Yellow needle-like crystals (Methanol) | 246–248 |
| 12 | phenyl | $CH_3$ | $CH_3$ | $CH_3$ | H | Colorless granular crystals (Ethanol) | 181–183 |
| 13 | $-CH_2-C_6H_4-OCH_3$ (4-) | H | $CH_3$ | $CH_3$ | H | Yellow prism-like crystals (Ethanol) | 152–153 |
| 14 | phenyl | H | Cl | $CH_3$ | H | Light yellow powdery crystals (Ethanol) | 169–171 |
| 15 | phenyl | H | $CH_3$ | $-Br$ | H | Colorless powdery crystals (Ethanol) | 162–165 (decomposed) |
| 16 | $-CH_2-$phenyl | H | $CH_3$ | $CH_3$ | H | Colorless prism-like crystals (Ethanol) | 163–168 |

TABLE 3-continued

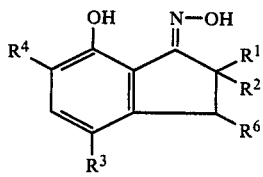

| Example No. | R¹ | R² | R³ | R⁴ | R⁶ | Crystal form (Recrystallization solvent) | Melting point (°C.) |
|---|---|---|---|---|---|---|---|
| 17 | —CH₂—(phenyl) | CH₃ | CH₃ | CH₃ | H | Colorless powdery crystals (Ethanol) | 161–162 |
| 18 | —CH₂—(phenyl) | CH₃ | CH₃ | CH₃ | H | Colorless prism-like crystals (Ethanol) | 164–165 |
| 19 | —CH₂—(4-chlorophenyl) | H | CH₃ | CH₃  CH₃ | H | Colorless prism-like crystals (Ethanol) | 164–165 |
| 20 | —CH₂—(3,4-methylenedioxyphenyl) | H | CH₃ | CH₃ | H | Colorless prism-like crystals (Ethanol-n-hexane) | 170–171 |
| 21 | —CH₂—(cyclohexyl) | CH₃ | CH₃ | CH₃ | H | Colorless prism-like crystals (n-Hexane) | 109–110 |

EXAMPLE 22

2.93 Grams of 2,3-dihydro-7-hydroxy-4-methyl-6-(1-phenyl-2-propenyl)-1H-inden-1-one oxime and 0.293 g of platinum oxide were suspended in 200 ml of acetic acid, then the suspension was reduced at room temperature under 3 atmospheric hydrogen pressure for 8 hours. After the completion of hydrogenation, the catalyst was removed by filtration, and the filtrate thus obtain was concentrated to dryness under a reduced pressure. The residue thus obtained was dissolved in 100 ml of ethanol and the pH of the solution was adjusted to about pH=1 by adding an ethanol solution saturated with hydrogen chloride gas, then this solution was again concentrated to dryness under a reduced pressure. The residue thus obtained was recrystallized from ethanoldiethyl ether to obtain 0.88 g of 1-amino-2,3-dihydro-7-hydroxy-4-methyl-6-(1-phenylpropyl)-1H-indene hydrochloride. Colorless powdery crystals. Melting point: 187.5°–189.5° C.

EXAMPLE 23

2.93 Grams of 2,3-dihydro-y-hydroxy-4-methyl-6-(1-phenyl-2-propenyl)-1-H-inden-1-one oxime and 0.293 g of platinum oxide were suspended in 200 ml of acetic acid, then the suspension was reduced at room temperature under 7 atmospheric hydrogen pressure for 8 hours. After the completion of the hydrogenation, the catalyst was removed by filtration, and the filtrate thus obtained was concentrated to dryness under a reduced pressure. The residue thus obtained was dissolved in 100 ml of ethanol, and the pH of this solution was adjusted to about pH=1 by adding an ethanol solution saturated with hydrogen chloride gas, then this solution was again concentrated to dryness under a reduced pressure. The residue thus obtained was recrystallized from diethyl ether-n-hexane to obtain 1.0 g of 1-amino-2,3-dihydro-7-hydroxy-4-methyl-6-(1-cyclohexylpropyl)-1H-indene hydrochloride. Colorless powdery crystals. Melting point: 184°–185.5° C.

EXAMPLE 24

4.79 Grams of 2,3-dihydro-4,6-dimethyl-2-phenyl-7-hydroxy-1H-inden-1-one was dissolved in 88 ml of glacial acetic acid, and this solution was subjected to catalytic hydrogenation in the presence of 0.71 g of platinum oxide, at 50° C., under 4 atmospheric hydrogen gas pressure for 18 hours. After the completion of the dydrogenation, the catalyst was removed by filtration and the filtrate was concentrated under a reduced pressure. To the residue thus obtained was added 100 ml of water, neutralized with an aqueous solution saturated with sodium bicarbonate, then extracted with 300 ml of chloroform. The insoluble matters were collected by filtration, and washed with water and diethyl ether, then recrystallized from ethanol to obtain 2.50 g of 1-amino-2-cyclohexyl-2,3-dihydro-4,6-dimethyl-7-hydroxy-1H-indene acetate (in which the substituents bonded at 1- and 2-positions in the indene skeleton are oriented as trans-form). Light yellow powdery crystals.

Melting point: 170°–172° C. (Decomposed)

NMR (DMSO-d$_6$) δ: 6.74 (s, 1H), 447 (d, 1H, J=6Hz), 2.80–2.45 (m, 2H), 2.09 (s, 6H), 1.85 (s, 3H), 1.97–0.83 (m, 12H).

The filtrate obtained after removal of the insoluble matters was washed with water and dried with anhydrous magnesium sulfate. The solvent was removed by evaporation under a reduced pressure to obtain the residue. Recrystallized from ethanol to obtain 1.40 g of 1-amino-2-cyclohexyl-2,3-dihydro-4,6-dimethyl-7-hydroxy-1H-indene (in which the substituents bonded at 1- and 2-positions in the indene skeleton are oriented as cis-form). Colorless needle-like crystals. Melting point: 125°–126° C. NMR (CDCl$_3$) δ: 677 (s, 1H), 4.30 (d, 1H, J=7.5Hz), 3.03–2.70 (m, 1H0, 2.87 (d-d, 1H, J=15Hz, 7.5Hz), 2.42 (d-d, 1H, J=15Hz, 3Hz), 2.18 (s, 3H), 2.12 (s, 3H), 1.07–1.97 (m, 11H).

EXAMPLE 25

3.00 Grams of 2,3-dihydro-4,6-dimethyl-7-hydroxy-2-phenyl-1H-inden-1-one oxime was dissolved in 55 ml of glacial acetic acid, and this solution was subjected to catalytic hydrogenation in the presence of 0.3 g of platinum oxide at room temperature under 4 atmospheric hydrogen gas pressude. The hydrogenation was terminated at the point when the stoichiometric amount of hydrogen was absorbed. The catalyst was removed by filtration and the filtrate thus obtained was concentrated. The residue thus obtained was dissolved in water and the pH of this solution was adjusted to about pH 8 by adding an aqueous solution of sodium bicarbonate, then extracted with 200 ml of chloroform. The chloroform extract was washed with water, dried with anhydrous magnesium sulfate, then concentrated under a reduced pressure. Recrystallized from ethanol to obtain 0.24 g of 1-amino-2,3-dihydro-4,6-dimethyl-7-hydroxy-2-phenyl-1H-indene. Colorless needle-like crystals. Melting point: 135°–136° C.

NMR (CDCl$_3$) δ: 7.30–7.13 (m, 3H), 7.03–6.87 (m, 2H), 6.80 (s, 1H), 4.89 (d, 1H, J=7.5Hz), 3.68 (d-d-d, 1H, J=7.5Hz, 7.5Hz, 3.0Hz), 3.25 (d-d, 1H, J=16.5Hz, 7.5Hz), 2.95 (d-d, 1H, J=16.5, 3.0Hz), 2.18 (s, 6H).

EXAMPLES 26–44

By methods similar to those described in Examples 22–25, and by using suitable starting materials, there were prepared compounds of Examples 26–44 shown in Table 4 as follows.

TABLE 4

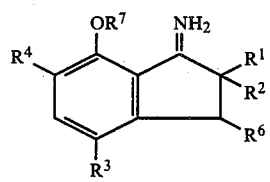

| Example No | R$^1$ | R$^2$ | R$^3$ | R$^4$ | R$^6$ | R$^7$ | Crystal form (Recrystallization solvent) | Melting point (°C.) | Salt |
|---|---|---|---|---|---|---|---|---|---|
| 26 | –⟨phenyl⟩ | CH$_3$ | CH$_3$ | H | H | H | Colorless powdery crystals (Ethanol) | 206–208 (NMR *1) | Hydrochloride |
| 27 | –⟨phenyl⟩–Cl | H | CH$_3$ | CH$_3$ | H | H | Light yellow needle-like crystals (Ethanol) | 124–126 (NMR *2) | Acetate |
| 28 | –⟨phenyl⟩–Cl | H | CH$_3$ | CH$_3$ | H | H | Light yellow needle-like crystals (Ethanol) | 131.5–132.5 (NMR *3) | — |
| 29 | H | H | CH$_3$ | CH$_3$ | –⟨phenyl⟩ | H | Colorless powdery crystals (Ethanol) | 212–214 (decomposed) (NMR *10) | — |
| 30 | CH$_3$ | H | CH$_3$ | –CHCH$_3$ \| C$_2$H$_5$ | –⟨phenyl⟩ | H | Colorless powdery crystals (Diethyl ether) | 128–129 | Acetate |
| 31 | –⟨phenyl⟩–CH$_3$ | H | CH$_3$ | CH$_3$ | H | H | Colorless powdery crystals (Ethanol-diethyl ether) | 134–138 (NMR *4) | Semifumarate |

TABLE 4-continued

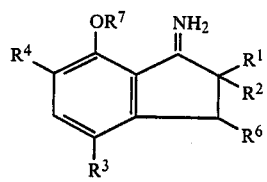

| Example No | R¹ | R² | R³ | R⁴ | R⁶ | R⁷ | Crystal form (Recrystallization solvent) | Melting point (°C.) | Salt |
|---|---|---|---|---|---|---|---|---|---|
| 32 | (2-methylphenyl, CH₃) | H | CH₃ | CH₃ | H | H | Colorless powdery crystals (Ethanol-ethyl acetate) | 198 (NMR *5) | Hydrochloride |
| 33 | (2-chlorophenyl) | H | CH₃ | CH₃ | H | H | Colorless powdery crystals (Ethanol) | 194–197 (NMR *11) | Fumarate |
| 34 | —CH₂—(4-methoxyphenyl)—OCH₃ | H | CH₃ | CH₃ | H | H | Colorless prism-like crystals (Ethanol) | 193–194 (NMR *6) | Semi-fumarate |
| 35 | phenyl | H | CH₃ | Br | H | H | Colorless powdery crystals (Ethanol) | 123–124 (NMR *13) | — |
| 36 | phenyl | H | Cl | CH₃ | H | H | Colorless powdery crystals (Ethanol) | 113–115 (NMR *7) | — |
| 37 | phenyl | H | CH₃ | C₂H₅ | H | H | Colorless prism-like crystals (Ethanol) | 79–80 (NMR *8) | — |
| 38 | —CH₂—phenyl | H | CH₃ | CH₃ | H | H | Colorless powdery crystals (Ethanol) | 145–146 (NMR *12) | Semi-fumarate monohydrate |
| 39 | —CH₂—(4-chlorophenyl)—Cl | H | CH₃ | CH₃ | H | H | Colorless needle-like crystals (Ethanol) | 215–216 (NMR *15) | Fumarate |
| 40 | —CH₂—(3,4-methylenedioxyphenyl) | H | CH₃ | CH₃ | H | H | Colorless powdery crystals (Ethanol) | 184–185 (NMR *16) | Semi-fumarate |
| 41 | (2-chlorocyclohexyl) | H | CH₃ | CH₃ | H | H | Colorless needle-like crystals (Ethanol) | 196–197 (NMR *9) | Hydrochloride |

TABLE 4-continued

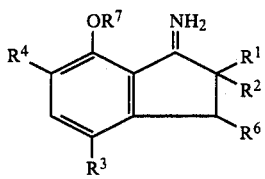

| Example No | R¹ | R² | R³ | R⁴ | R⁶ | R⁷ | Crystal form (Recrystallization solvent) | Melting point (°C.) | Salt |
|---|---|---|---|---|---|---|---|---|---|
| 42 | phenyl | CH₃ | CH₃ | CH₃ | H | CH₃ | Colorless needle-like crystals (Ethanol) | 247–249 (decomposed) | Hydrochloride ·¼ hydrate |
| 43 | phenyl | H | CH₃ | H | H | H | Colorless granular crystals (Ethanol) | 192–196 (NMR *14) | Hydro chloride |
| 44 | –CH₂–cyclohexyl | CH₃ | CH₃ | CH₃ | H | H | Colorless needle-like crystals (Ethanol) | 189–190 (NMR *17) | Hydrochloride |

(*1) NMR (CDCl₃)δ: 7.26–7.00 (m, 5H), 6.78 (s, 1H), 4.40 (s, 1H), 4.0 (br, 2H), 3.30 (d, 1H, J=18Hz), 2.86 (d, 1H, J=17Hz), 2.15 (s, 6H), 1.59 (s, 3H)

(2*) NMR (DMSO—d₆)δ: 7.35 (d, 2H, J=8.5Hz), 7.14 (d, 2H, J=8.5Hz), 6.77 (s, 1H), 4.74 (d, 1H, J=6Hz), 3.85–3.60 (m, 1H), 3.20–2.95 (m, 2H), 2.15 (s, 3H), 2.10 (s, 3H)

(*3) NMR (CDCl₃)δ: 7.20 (d, 2H, J=8.5Hz), 6.88 (d, 2H, J=8.5Hz), 6.83 (s, 1H), 4.90 (d, 1H, J=7.0Hz), 3.75–3.50 (m, 1H), 3.24 (d-d, 1H, J=15Hz, 7.0Hz), 3.95 (d-d, 1H, J=15Hz, 3Hz), 2.19 (s, 6H)

(*4) NMR (CDCl₃—DMSO—D₆)δ: 7.05 (s, 4H), 6.80 (s, 1H), 6.60 (s, 1H), 4.78 (d, 1H, J=7.5Hz), 3.65 (m, 1H), 3.15–2.90 (m, 2H), 2.25 (s, 3H), 2.12 (s, 6H)

(*5) NMR (DMSO—d₆)δ: 2.17 (s, 6H), 2.40 (s, 3H), 2.91 (d-d, 1H, J=15Hz, 6Hz), 3.60 (d-d, 1H, J=15Hz, 12Hz), 3.80–4.17 (m, 1H), 4.80–5.10 (m, 1H), 6.95 (s, 1H), 7.10–7.30 (m, 3H), 7.43–8.00 (m, 3H), 9.10 (br, 1H)

(*6) NMR (DMSO—d₆)δ: 2.01 (s, 3H), 2.06 (s, 3H), 2.30–3.20 (m, 5H), 4.21 (m, 1H), 6.46 (s, 1H), 6.73 (s, 1H), 6.87 (d, 2H, J=8Hz), 7.13 (d, 2H, J=8Hz)

(*7) NMR (CDCl₃)δ: 7.40–7.18 (m, 3H), 7.10–6.90 (m, 3H), 4.90 (d, 1H, J=7.5Hz), 3.84–3.60 (m, 1H), 3.50–3.10 (m, 2.20 (s, 3H)

(*8) NMR (CDCl₃)δ: 7.25–7.10 (m, 3H), 6.92 (m, 2H), 6.80 (s, 1H), 4.88 (d, 1H, J=7.5Hz), 3.68 (t-d, 1H, J=7.0Hz, 3Hz), 3.25 (d-d, 1H, J=15Hz, 7.5 Hz), 2.95 (d-d, 1H, J=15Hz, 3Hz), 2.80–2.35 (m, 2H), 1.20 (t, 3H)

(*9) NMR (CDCl₃—DMSO—d₆)δ: 8.60–7.70 (br, 4H), 6.83 (s, 1H), 4.73 (d, 1H, J=6Hz), 3.50–3.20 (m, 1H), 2.85–2.60 (m, 2H), 2.18 (s, 3H), 2.12 (s, 3H), 2.20–0.80 (m, 10H)

(*10) NMR (CDCl₃)δ: 2.18 (s, 6H), 2.95 (d-d, 1H, J=15Hz, 3Hz), 3.25 (d-d, 1H, J=16.5Hz, 7.5Hz), 3.68 (d-d-d, 1H, J=7.5Hz, 7.5Hz, 3.0Hz), 4.89 (d, 1H, J=7.5Hz), 6.80 (s, 1H), 6.87–7.03 (m, 2H), 7.13–.30 (m, 3H)

(*11) NMR (CDCl₃—DMSO—d₆)δ: 7.40–7.15 (m, 5H), 6.83 (s, 1H), 6.68 (s, 2H), 4.85 (d, J=7.5Hz, 1H), 3.90–3.60 (m, 1H), 3.25–3.10 (m, 2H), 2.18 (s, 6H)

(*12) NMR (DMSO—d₆)δ: 2.06 (s, 3H), 2.11 (s, 3H), 2.30–3.30 (m, 5H), 4.70 (m, 1H), 6.50 (s, 1H), 6.79 (s, 1H), 7.20–7.40 (m, 5H), 7.00–8.20 (broad, 6H)

(*13) NMR (CDCl₃)δ: 2.20 (3H, s), 2.99 (1H, ddd, J=7.5Hz, 3Hz), 4.91 (1H, d, J=7.5Hz), 6.89 (1H, d, J=6Hz), 6.93 (1H, d, J=6.0Hz), 7.20 (4H, s)

(*14) NMR (DMSO—d₆)δ: 2.20 (3H, s), 3.03 (1H, dd, J=15Hz, 7.5 Hz), 3.27–4.03 (2H, m), 4.67–4.93 (1H, brm), 6.90 (2H, ABq, J=22.5Hz, 8.5Hz), 7.23–7.63 (5H, m), 7.67–8.03 (3H, brm), 9.77–10.07 (1H, brm)

(*15) NMR (DMSO—d₆)δ: 2.02 (s, 3H), 2.10 (s, 3H), 2.15–3.15 (m, 5H), 4.35 (m, 1H), 6.50 (s, 2H), 6.82 (s, 1H), 7.20–7.50 (m, 4H), 8.20–10.00 (broad, 5H)

(*16) NMR (DMSO—d₆)δ: 2.01 (s, 3H), 2.10 (s, 3H), 2.20–3.20 (m, 5H), 4.65 (s, 1H), 5.97 (s, 2H), 6.45 (s, 1H), 6.50–7.00 (m, 4H), 7.90–9.00 (broad, 4H)

(*17) NMR (DMSO—d₆)δ: 0.98 (s, 3H), 0.50–2.00 (m, 13H), 2.09 (s, 3H), 2.15 (s, 3H), 2.55 (d, 1H, J=15Hz), 3.94 (d, 1H, J=15Hz), 4.23 (s, 1H), 6.90 (s, 1H), 8.2–9.5 (broad, 4H)

EXAMPLE 45

To a chloroform solution containing 31.8 g of 1-amino-2,3-dihydro-7-hydroxy-4-methyl-6-(1-phenylpropyl)-1H-indene hydrochloride and 15.2 g of triethylamine dissolved in 200 ml of chloroform was added dropwise 13.56 g of chloroacetyl chloride under ice-cooled with stirring condition. After finished the dropwise addition, the reaction mixture was stirred at 25° C for 3 hours. After the reaction was completed, the reaction mixture was washed with 100 ml of 1N-hydrochloric acid aqueous solution, then washed three times with 100 ml of water each time. After dried with anhydrous magnesium sulfate, the reaction mixture was concentrated by evaporating the solvent under a reduced pressure. The residue thus obtained was recrystallized from diethyl ether-n-hexane to obtain 14.7 g of 1-chloroacetylamino-2,3-dihydro-4-methyl-6-(1-phenylpropyl)-7-hydroxy-1H-indene. Colorless powdery crystals. Melting point: 172°–174° C.

EXAMPLES 46–49

By a method similar to that described in Example 45, and by using a suitable starting material, there were prepared compounds of Examples 46–49 as shown in Table 5 as follows.

TABLE 5

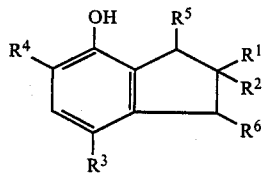

| Example No. | R¹ | R² | R³ | R⁴ | R⁵ | R⁶ | Crystal form (Recrystallization solvent) | Melting point (°C.) |
|---|---|---|---|---|---|---|---|---|
| 46 | H | H | | CH₃ | —CH(C₂H₅)—cyclohexyl | —NHCOCH₂Cl | H | Colorless powdery crystals (n-Hexane) | 131–132 |
| 47 | cyclohexyl | H | CH₃ | CH₃ | —NHCOCH₂Cl | H | Colorless needle-like crystals (Ethanol) | 189–190 |
| 48 | phenyl | H | CH₃ | CH₃ | —NHCOCH₂Cl | H | Colorless powdery crystals (Ethanol) | 123–124 |
| 49 | 4-Cl-phenyl | H | CH₃ | CH₃ | —NHCOCH₂Cl | H | Colorless needle-like crystals (Ethanol) | 186–187 |

EXAMPLE 50

6.64 Grams of 1-chloroacetylamino-2,3-dihydro-7-hydroxy-2,2,4,6-tetramethyl-1H-indene was dissolved in 100 ml of acetonitrile. Under stirring condition, 9.27 g of 4-(3-chlorophenyl)piperazine was added thereto, then the reaction mixture was refluxed for 2 hours. After the reaction was completed, the reaction mixture was ice-cooled and an excess of 4-(3-chlorophenyl)piperazine being separated was removed by filtration, the filtrate thus obtained was concentrated under a reduced pressure. The residue thus obtained was recrystallized from ethanol to obtain 8.10 g of 1-[4-(3-chlorophenyl)-1-piperazinyl]-acetylamino-2,3-dihydro-7-hydroxy-2,2,4,6-tetramethyl-1H-indene. Colorless powdery crystals. Melting point: 125°–126° C.

EXAMPLES 51–65

By a method similar to that described in Example 50, and by using a suitable starting material, there were prepared compounds of Examples 51–65 as shown in Table 6 as follows.

TABLE 6

[Structure: indane with OH, R¹, R², R³, R⁴, R⁵, R⁶ substituents]

| Example No. | R¹ | R² | R³ | R⁴ | R⁵ | R⁶ | Crystal form (Recrystallization solvent) | Melting point (°C.) | salt |
|---|---|---|---|---|---|---|---|---|---|
| 51 | $CH_3$ | $CH_3$ | $CH_3$ | $CH_3$ | $-NHCOCH_2CH_2N\overset{\displaystyle\frown}{\underset{\displaystyle\smile}{\text{N}}}-\!\!\left\langle\!\!\begin{array}{c}\\ \end{array}\!\!\right\rangle\!\!-Cl$ (3-Cl-phenyl piperazinyl) | H | Colorless powdery crystals (Ethanol) | 157–158 | — |
| 52 | $CH_3$ | $CH_3$ | $CH_3$ | $CH_3$ | $-NHCOCH_2-N\!\!\left\langle\!\!\begin{array}{c}\\ \end{array}\!\!\right\rangle\!\!-OCH_3$ (3-OCH₃-phenyl piperazinyl) | H | Colorless powdery crystals (Ethanol) | 103.5–106 | — |
| 53 | H | H | $CH_3$ | $-CHCH_3$ $\;\;\;\;\;\;\;\;\;\;\; C_2H_5$ | $-NHCOCH_2-N\!\!\left\langle\!\!\begin{array}{c}\\ \end{array}\!\!\right\rangle\!\!-\text{phenyl}$ | H | Colorless powdery crystals (Ethanol) | 131–132 | — |
| 54 | H | H | $CH_3$ | $-CHCH_3$ $\;\;\;\;\;\;\;\;\;\;\; C_2H_5$ | $-NHCOCH_2-N\!\!\left\langle\!\!\begin{array}{c}\\ \end{array}\!\!\right\rangle\!\!-CH_3$ (3-CH₃-phenyl piperazinyl) | H | Colorless powdery crystals (Ethanol) | 106–107 | — |
| 55 | H | H | $CH_3$ | $-CHCH_3$ $\;\;\;\;\;\;\;\;\;\;\; C_2H_5$ | $-NHCOCH_2-N\!\!\left\langle\!\!\begin{array}{c}\\ \end{array}\!\!\right\rangle\!\!-OCH_3$ (3-OCH₃-phenyl piperazinyl) | H | Colorless powdery crystals (Acetone) | 165–166 | Dihydrochloride |

TABLE 6-continued

![Structure: indane with R1, R2, R6 on saturated ring, R5 on benzylic carbon, OH at position 1, R4 at position 2, R3 at position 5 of aromatic ring]

| Example No. | R¹ | R² | R³ | R⁴ | R⁵ | R⁶ | Crystal form (Recrystallization solvent) | Melting point (°C.) | salt |
|---|---|---|---|---|---|---|---|---|---|
| 56 | H | H | CH₃ | —CHCH₃<br>C₂H₅ | —NHCOCH₂—N(piperazine)—(3,5-dichlorophenyl) | H | Colorless powdery crystals (Ethanol) | 156 | — |
| 57 | H | H | CH₃ | —CHCH₃<br>C₂H₅ | —NHCOCH₂—N(piperazine)—(3-chlorophenyl) | H | Colorless powdery crystals (Acetone) | 184.5–186 | Hydrochloride |
| 58 | H | H | CH₃ | —CHCH₃<br>C₂H₅ | —NHCOCH₂—N(piperazine)—(2,3-dichlorophenyl) | H | Colorless plate-like crystals (Ethanol) | 149–150 | — |
| 59 | CH₃ | CH₃ | CH₃ | —CHCH₃<br>C₂H₅ | —NHCOCH₂—N(piperazine)—(3-chlorophenyl) | H | Colorless powdery crystals (Ethanol) | 130–131 | — |
| 60 | CH₃ | CH₃ | CH₃ | CH₃ | —NHCOCH₂—N(piperazine)—(2,6-dimethyl-4-methylphenyl) | H | Colorless powdery crystals (Ethanol) | 210–211 | — |

TABLE 6-continued

Structure:

R¹, R² on one carbon; R⁶ on adjacent carbon; R⁵ on carbon attached to aromatic ring; aromatic ring bears OH, R⁴, R³.

| Example No. | $R^1$ | $R^2$ | $R^3$ | $R^4$ | $R^5$ | $R^6$ | Crystal form (Recrystallization solvent) | Melting point (°C.) | salt |
|---|---|---|---|---|---|---|---|---|---|
| 61 | $CH_3$ | $CH_3$ | $CH_3$ | $CH_3$ | $-NHCOCH_2-N$(piperazine)-(4-$NO_2$-phenyl) | H | Colorless powdery crystals (Ethanol) | 201–202 | — |
| 62 | H | H | $CH_3$ | $CH_3$ | $-NHCOCH_2-N$(piperazine)-(3-Cl-phenyl) | H | Colorless needle-like crystals (Ethanol) | 174–176 | Hydrochloride |
| 63 | H | H | $CH_3$ | $CH_3$ | $-NHCOCH_2-N$(piperazine)-(2,3-di-$CH_3$-phenyl) | H | Colorless needle-like crystals (Ethanol) | 196–198 | Hydrochloride |
| 64 | H | H | $CH_3$ | $-CH(C_2H_5)$-phenyl | $-NHCOCH_2-N$(piperazine)-(3-Cl-phenyl) | H | Colorless powdery crystals (Diethyl ether–n-hexane) | 177–178 | — |
| 65 | H | H | $CH_3$ | $-CH(C_2H_5)$-cyclohexyl | $-NHCOCH_2-N$(piperazine)-(3-Cl-phenyl) | H | Colorless powdery crystals (Diethyl ether–n-hexane) | 141–143.0 | Hydrochloride |

Examples 66-101

By a method similar to that described in Example 50, and by using a suitable starting material, there were prepared compounds of Examples 66-101 as shown in Table 7 as follows.

TABLE 7

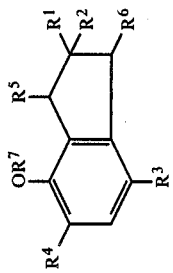

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 66 | CH₃ | CH₃ | CH₃ | CH₃ | —NHCOCH₂—N(piperazine)—N(2-pyridyl) | H | H | Colorless powdery crystals (Ethanol) | 142–143 | — |
| 67 | CH₃ | CH₃ | CH₃ | CH₃ | —NHCOCH₂—N(piperazine)—N(3-methoxyphenyl), with CH₃ on piperazine | H | H | Colorless needle-like crystals (Ethanol) | 84–87 | — |
| 68 | CH₃ | CH₃ | CH₃ | CH₃ | —NHCOCH₂—N(piperazine)—N(3-methoxyphenyl) | H | CH₃ | Colorless powdery crystals (Ethanol) | 170–171 | — |
| 69 | —CH(CH₃)—CH₃ | H | CH₃ | CH₃ | —NHCOCH₂—N(piperazine)—N(3-methoxyphenyl) | H | H | Colorless powdery crystals (Ethanol) | 134.5–136.5 | Semifumarate |
| 70 | 4-chlorophenyl | H | CH₃ | CH₃ | —NHCOCH₂—N(piperazine)—N(3-chlorophenyl) | H | H | Colorless needle-like crystals (Ethanol) | 204–205 | — |

TABLE 7-continued

Structure:

OR⁷ position on fused benzene ring of indane with R¹ (on sp3 C adjacent to OR⁷-bearing ring), R² and R⁶ on the 2-position carbons, R⁵ on the 1-position carbon; R³ and R⁴ on the aromatic ring.

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 71 | H | H | CH₃ | CH₃ | —NHCOCH₂—N(piperazinyl)—(3-methoxyphenyl) | H | H | Colorless powdery crystals (Ethanol) | 152–157 | Oxalate |
| 72 | 4-chlorophenyl | H | CH₃ | CH₃ | —NHCOCH₂—N(piperazinyl)—(3-methoxyphenyl) | H | H | Colorless needle-like crystals (Ethanol) | 175.5–179 | — |
| 73 | —CHCH(CH₃)CH₃ | H | CH₃ | CH₃ | —NHCOCH₂—N(piperazinyl)—(3-methoxyphenyl) | H | H | Colorless prism-like crystals (Ethanol) | 174–176 | — |
| 74 | CH₃ | CH₃ | CH₃ | CH₃ | —NHCOCH₂—N(piperazinyl)—(3-trifluoromethylphenyl) | H | H | Colorless prism-like crystals (Diethyl ether) | 83–84 | Oxalate |
| 75 | CH₃ | CH₃ | CH₃ | CH₃ | —NHCOCH₂—N(piperazinyl)—CH₂—phenyl | H | H | Colorless powdery crystals (Ethanol) | 195–196 | Dihydrochloride |

TABLE 7-continued structure: indane core with substituents OR⁷, R¹, R², R³, R⁴, R⁵, R⁶

| Example No. | $R^1$ | $R^2$ | $R^3$ | $R^4$ | $R^5$ | $R^6$ | $R^7$ | Crystal form (Recrystallization solvent) | Melting point (°C.) | Salt |
|---|---|---|---|---|---|---|---|---|---|---|
| 76 | $CH_3$ | $CH_3$ | $CH_3$ | $CH_3$ | $-NHCOCH_2-N\bigcirc N-C(=O)-C_6H_4-OCH_3$ (p) | H | H | Colorless powdery crystals (Ethanol) | 112 (decomposed) | — |
| 77 | $CH_3$ | $CH_3$ | $CH_3$ | $CH_3$ | $-NHCOCH_2-N\bigcirc N-C_6H_4-OCH_3$ (p) | H | H | Colorless needle-like crystals (Ethanol/diethyl ether) | 104–108 | — |
| 78 | $CH_3$ | $CH_3$ | $CH_3$ | $CH_3$ | $-NHCOCH_2-N\bigcirc N-CH_2-CH_2-OH$ | H | H | Colorless powdery crystals (Ethanol) | 216–219 | Dihydrochloride |
| 79 | cyclohexyl | H | $CH_3$ | $CH_3$ | $-NHCOCH_2-N\bigcirc N-C_6H_4-OCH_3$ (m) | H | H | Colorless powdery crystals (Ethanol) | 128–130 | Semifumarate |
| 80 | cyclohexyl | H | $CH_3$ | $CH_3$ | $-NHCOCH_2-N\bigcirc N-C_6H_4-OCH_3$ (m) | H | H | Colorless needle-like crystals (Ethanol) | 155–156 | — |

TABLE 7-continued

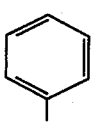

| Example No. | $R^1$ | $R^2$ | $R^3$ | $R^4$ | $R^5$ | $R^6$ | $R^7$ | Crystal form (Recrystallization solvent) | Melting point (°C.) | Salt |
|---|---|---|---|---|---|---|---|---|---|---|
| 81 | ⌬ | H | $CH_3$ | $CH_3$ | —NHCOCH$_2$—N⌬N—⌬—OCH$_3$ | H | H | Colorless needle-like crystals (Ethanol) | 143–144 | — |
| 82 | $CH_3$ | $CH_3$ | $CH_3$ | H | —NHCOCH$_2$—N⌬N—⌬—OCH$_3$ | H | H | Colorless prism-like crystals (Ethanol/diethyl ether) | 167–168 | Semifumarate |
| 83 | $CH_3$ | $CH_3$ | $CH_3$ | —CH$_2$—CH$_2$—CH$_2$— | —NHCOCH$_2$—N⌬N—⌬—OCH$_3$ | H | H | Colorless prism-like crystals (Ethanol/diethyl ether) | 135–137 | Dihydrochloride |
| 84 | $CH_3$ | $CH_3$ | $CH_3$ | $CH_3$ | —NHCOCH$_2$—N⌬N—⌬—F | H | H | Colorless powdery crystals (Diethyl ether-n-hexane) | 142–143 | Semifumarate |
| 85 | $CH_3$ | $CH_3$ | $CH_3$ | $CH_3$ | —NHCOCH$_2$—N⌬N—⌬—Br | H | H | Colorless needle-like crystals (Ethanol) | 125–126.5 | — |

TABLE 7-continued

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 86 | CH₃ | CH₃ | CH₃ | CH₃ |  | H | H | Colorless powdery crystals (Ethanol-water) | 125–126 | — |
| 87 | CH₃ | CH₃ | CH₃ | CH₃ |  | H | H | Colorless needle-like crystals (Ethanol) | 160–161.5 | — |
| 88 | CH₃ | CH₃ | CH₃ | CH₃ |  | H | H | Colorless needle-like crystals (Ethanol) | 187–188 | — |
| 89 | CH₃ | CH₃ | CH₃ | CH₃ |  | H | H | Colorless flake-like crystals (Ethanol) | 205–207 | — |
| 90 | CH₃ | CH₃ | CH₃ | CH₃ |  | H | H | Colorless needle-like crystals (Ethanol-water) | 168–170 | — |

TABLE 7-continued

Structure: Indane/indene core with substituents R¹, R², R³, R⁴, R⁵, R⁶, R⁷, OR⁷

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 91 | CH₃ | CH₃ | CH₃ | CH₃ | —NHCOCH₂—N(piperazine)—(3,4-dichlorophenyl) | H | H | Colorless needle-like crystals (Ethanol-water) | 177–178 | — |
| 92 | CH₃ | CH₃ | CH₃ | CH₃ | —NHCOCH₂—N(piperazine)—(2-chlorophenyl) | H | H | Colorless needle-like crystals (Ethanol-water) | 176–177 | — |
| 93 | CH₃ | CH₃ | CH₃ | CH₃ | —NHCOCH₂—N(piperazine)—CH₂—C(=O)—N(pyrrolidine) | H | H | Colorless needle-like crystals (Ethanol-water) | 107–108 | — |
| 94 | CH₃ | H | CH₃ | CH₃ | —NHCOCH₂—N(piperidine)—(benzimidazolinone) | H | H | Colorless needle-like crystals (Ethanol-water) | 224–226 | — |
| 95 | (o-tolyl, H₃C-C₆H₄-) | H | CH₃ | CH₃ | —NHCOCH₂—N(piperazine)—(3,4-dichlorophenyl) | H | H | Colorless needle-like crystals (Ethyl acetate-n-hexane) | 187–189 | — |

TABLE 7-continued structure: indane with OR⁷ at position, R¹, R², R³, R⁴, R⁵, R⁶ substituents

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 96 | $CH_3$ | $CH_3$ | $CH_3$ | $CH_3$ | —NHCOCH₂—N(piperazine)—(2-fluorophenyl) | H | H | Colorless needle-like crystals (Ethanol) | 165–166 | — |
| 97 | $CH_3$ | $CH_3$ | $CH_3$ | $CH_3$ | —NHCOCH₂—N(piperazine)—(4-fluorophenyl) | H | H | Colorless needle-like crystals (Ethanol) | 166–167 | — |
| 98 | $CH_3$ | $CH_3$ | $CH_3$ | $CH_3$ | —NHCOCH₂—N(piperazine)—(2,3-dichlorophenyl) | H | H | Colorless needle-like crystals (Ethanol) | 178–179 | — |
| 99 | $CH_3$ | $CH_3$ | $CH_3$ | $CH_3$ | —NHCOCH₂—N(piperazine)—(2,5-dichlorophenyl) | H | H | Colorless needle-like crystals (Ethanol) | 197–198.5 | — |
| 100 | $CH_3$ | $CH_3$ | $CH_3$ | $CH_3$ | —NHCOCH₂—N(piperazine)—(2-ethoxyphenyl) | H | H | Colorless needle-like crystals (Ethanol-water) | 172–174 | — |

TABLE 7-continued

| Example No. | R¹ | R² | R³ | R⁴ | R⁵ | R⁶ | R⁷ | Crystal form (Recrystallization solvent) | Melting point (°C.) | Salt |
|---|---|---|---|---|---|---|---|---|---|---|
| 101 | C₆H₅ | CH₃ | CH₃ | CH₃ | —NHCOCH₂—N(piperazine)—C₆H₄(3-OCH₃) | H | CH₃ | Colorless powdery crystals (Ethanol) | 139.5–141.0 | Fumarate |

EXAMPLE 102

3.63 Grams of 2-pyrrolidone was dissolved in 40 ml of dimethylformamide, then to this solution was added gradually 1.71 g of 60%-sodium hydride, and the whole mixture was stirred for 30 minutes. To this suspension was added 4.00 g of 1-chloroacetylamino-2,3-dihydro-7-hydroxy-2,2,4,6-tetramethyl-1H-indene and the reaction mixture was stirred at room temperature for 30 minutes. After the reaction was completed, the reaction mixture was poured in 100 ml of ice-water, and extracted with 200 ml of methylene chloride. The extract was washed with water, then dried with anhydrous magnesium sulfate and the solvent was removed by evaporation under a reduced pressure. The residue thus obtained was purified by a silica gel column chromatography (eluent: ethyl acetate:n-hexane =1:2), and recrystallized from ethanol to obtain 2.27 g of 2,3-dihydro-7-hydroxy-1-(2-pyrrolidon-1-yl)acetylamino-2,2,4,6-tetramethyl-1H-indene. Colorless needle-like crystals. Melting point: 165°–168° C.

EXAMPLE 103

A mixture of 1.07 g of 4-methylpiperazine, 1.5 g of 1-chloroacetylamino-2,3-dihydro-7-hydroxy-2,2,4,6-tetramethyl-1H-indene and 24 ml of acetonitrile was refluxed for 2 hours. After the reaction was completed, the reaction mixture was ice-cooled, and the crystals being separated were removed by filtration, and the filtrate was concentrated under a reduced pressure. The residue thus obtained was purified by a silica gel column chromatography (eluent: ethyl acetate:n-hexane=1:2), next recrystallized from ethanol to obtain 1.20 g of 2,3-dihydro-7-hydroxy-1-(4-methyl-1-piperazinyl)acetylamino-2,2,4,6-tetramethyl-1H-indene. Colorless needle-like crystals. Melting point: 189°–190° C.

EXAMPLES 104–111

By a method similar to that described in Example 103, and by using suitable starting materials, there were prepared compounds of Examples 104–111 as shown in Table 8 as follows.

TABLE 8

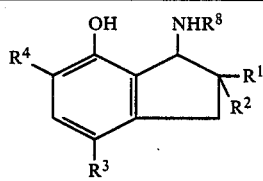

| Example No. | $R^1$ | $R^2$ | $R^3$ | $R^4$ | $R^8$ | Crystal form (Recrystallization solvent) | Melting point (°C.) |
|---|---|---|---|---|---|---|---|
| 104 | $CH_3$ | $CH_3$ | $CH_3$ | $CH_3$ | —COCH₂—N(morpholino, O) | Colorless needle-like crystals (Ethanol) | 168–169 |
| 105 | $CH_3$ | $CH_3$ | $CH_3$ | $CH_3$ | —COCH₂—N(thiomorpholino, S) | Colorless needle-like crystals (Ethanol) | 198–199 |
| 106 | $CH_3$ | $CH_3$ | $CH_3$ | $CH_3$ | —COCH₂—N(piperazinyl, NH) | Colorless powdery crystals (Ethanol) | 250–252 |
| 107 | $CH_3$ | $CH_3$ | $CH_3$ | $CH_3$ | —COCH₂—N(piperidinyl) | Colorless needle-like crystals (Ethanol) | 147.5–148 |
| 108 | $CH_3$ | $CH_3$ | $CH_3$ | $CH_3$ | —COCH₂—N(pyrrolidinyl) | Colorless needle-like crystals (Ethanol) | 127–128 |
| 109 | $CH_3$ | $CH_3$ | $CH_3$ | $CH_3$ | —COCH₂—N(pyrrolidinyl-COOH) | Colorless needle-like crystals (Ethanol) | 209–211 (decomposed) |
| 110 | $CH_3$ | $CH_3$ | $CH_3$ | $CH_3$ | —COCH₂—N(imidazolyl) | Colorless needle-like crystals (Ethanol) | 242 (decomposed) |

TABLE 8-continued

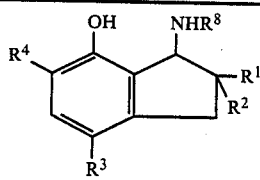

| Example No. | R¹ | R² | R³ | R⁴ | R⁸ | Crystal form (Recrystallization solvent) | Melting point (°C.) |
|---|---|---|---|---|---|---|---|
| 111 | CH₃ | CH₃ | CH₃ | —CHCH₃<br>\|<br>C₂H₅ | —COCH₂—N⌒N—CH₃ | Colorless needle-like crystals (n-Hexane) | 129–131 |

EXAMPLE 112

To an acetonitrile solution containing 2.50 g of 1-amino-2,3-dihydro-2,2,4,6-tetramethyl-7-hydroxy-1H-indene hydrochloride, 4.33 ml of triethylamine in 30 ml of acetonitrile was added 3.0 g of 1-chloroacetyl-4-(3-methoxyphenyl)piperazine, and the reaction mixture was refluxed for 10 hours. After the reaction was completed, the solvent was removed by evaporation, and the residue thus obtained was dissolved in 200 ml of chloroform, then this chloroform solution was washed with water and dried with anhydrous magnesium sulfate. The solvent was again removed under a reduced pressure to obtain the residue, then said residue was purified by a silica gel column chromatography (eluent: ethyl acetate:n-hexane=1:2). Recrystallized from ethanol to obtain 0.90 g of 1-(2,3-dihydro-7-hydroxy-2,2,4,6-tetramethyl-1H-inden-lyl)-aminoacetyl-4-(3-methoxyphenyl)piperazine. Colorless flake-like crystals. Melting point: 164.5°–166.0° C.

EXAMPLE 113

By a method similar to that described in Example 112, and using a suitable starting material, the following compound was prepared.

1-(2,3-Dihydro-7-hydroxy-2,2,4,6-tetramethyl-1H-inden-1-yl)aminoacetyl-4-(3-chlorophenyl)piperazine. Colorless powdery crystals (from ethanol). Melting point: 144.0°–145.5° C.

EXAMPLE 114

To a solution containing 5.00 g of 1-[4-(3-chlorophenyl)-1-piperazinyl]acetylamino-2,3-dihydro-7-hydroxy-2,2,4,6-tetramethyl-1H-indene and 100 ml of diglyme (diethylene glycol dimethyl ether) was added 4.3 g of lithium aluminium hydride gradully, under stirring condition. Then the reaction mixture was refluxed for 3 hours. After the reaction was completed, the reaction mixture was ice-cooled, then ice-water was added to the reaction mixture so as to decompose an excess amount of lithium aluminium hydride. The whole mixture was filtered, and the filtrate was extracted with 200 ml of methylene chloride, and the extract was washed with water, dried with anhydrous magnesium sulfate, then the solvent was removed by evaporation under a reduced pressure. The residue thus obtained was dissolved in 50 ml of ethanol, then an ethanol solution containing 1.31 g of fumaric acid was added thereto and concentrated to dryness under a reduced pressure. Recrystallized from ethanol to obtain 2.3 g of 1-{2-[4-(3-chlorophenyl)-1-piperazinyl]ethylamino}-2,3-dihydro-7-hydroxy-2,2,4,6-tetramethyl-1H-indene fumarate. Colorless powdery crystals. Melting point: 144°–146° C.

EXAMPLE 115

By a method similar to that described in Example 114, using a suitable starting material, there was prepared the following compound.

1-{2-[4-(3-Methoxyphenyl)-1-piperazinyl]ethylamino}-2,3-dihydro-7-hydroxy-2,2,4,6-1H-indene fumarate. Colorless powdery crystals (from ethanol). Melting point: 122°–125° C.

Example 116

To a solution containing 22.65 g of 1-amino-2,3-dihydro-7-hydroxy-2,2,4,6-tetramethyl-1H-indene hydrochloride and 15.2 g of triethylamine in 200 ml of chloroform was added dropwise 32.76 g of [4-(3-chlorophenyl)1-piperazinyl]acetyl chloride, under ice-cooled condition with stirring. After finished the dropwise addition, the reaction mixture was stirred at 25° C. for 3 hours. After the reaction was completed, the reaction mixture was washed with 100 ml of 1N-hydrochloric acid aqueous solution, then further washed three times with 100 ml of water, then dried with anhydrous magnesium sulfate. The solvent was removed by evaporation under a reduced pressure, the residue thus obtained was recrystallized from ethanol of obtain 17.6 g of 1-{[4-(3-chlorophenyl)-1-piperazinyl]acetylamino}-2,3-dihydro-2,2,4,6-tetramethyl-7-hydroxy-1H-indene. Colorless powdery crystals. Melting point: 125°–126° C.

By a method similar to that described in Example 115, and using suitable starting materials, there were prepared compounds of Examples 51–111.

EXAMPLE 117

To a solution containing 1.77 g of 1-amino-2,3-dihydro-4,6-dimethyl-7-hydroxy-1H-indene and 2 ml of triethylamine in 100 ml of chloroform was added dropwise 2.23 g of octyl chloride at room temperature. Then the reaction mixture was stirred at the same temperature for 4 hours. The reaction mixture was washed with a diluted hydrochloric acid, water, an aqueous solution saturated with sodium bicarbonate, water and an aqueous soluction saturated with sodium chloride in this order, then dried with anhydrous sodium sulfate. The solvent was removed by evaporation and the residue thus obtained was dissolved in ethanol, then an ethanol saturated with hydrogen chloride gas was added thereto form a hydrochloride. Recrystallized from acetonitrile to obtain 0.49 g of 2,3-dihydro-1-octylamino- 4,6-dimethyl-7-hydroxy-1H-indene hydrochloride. Colorless needle-like crystals. Melting point: 120°–121° C.

By a method similar to that described in Example 117, and by using suitable starting materials, there were prepared compounds of Examples 114 and 115, further prepared compounds of Examples 118–121, 124 as mentioned below.

EXAMPLE 118

A solution containing 1.76 g of 2,3-dihydro-4,6-dimethyl-7-hydroxy-1H-inden 1-one and 25.8 g of n-octylamine in 100 ml ethanol was refluxed for 8 hours. After cooled the reaction mixture to room temperature, 1 g of sodium born hydride was added thereto, then the whole reaction mixture was further stirred at room temperature for 1 hour. The reaction mixture was concentrated to dryness, and the residue thus obtained was dissolved in 100 ml of water, then this solution was acidified with a concentrated hydrochloric acid, next the pH of this solution was adjusted by adding an aqueous solution saturated with sodium acetate to about pH 9. The separated matter was extracted with ethyl acetate, washed with water and dried. The solvent was removed by evaporation and the residue thus obtained was dissolved in 100 ml of ethanol, then an ethanol solution saturated with hydrogen chloride gas was added thereto to form hydrochloride. Recrystallized from acetonitrile to obtain 3.40 g of 2,3-dihydro-1-n-octylamino-4,6-dimethyl-7-hydroxy-1H-indene hydrochloride. Colorless needle-like crystals. Melting point: 120°–121° C.

EXAMPLES 119–121

By a method similar to that described in Example 118, and by using suitable starting materials, there were prepared compounds of Examples 119–121 shown in Table 9 as follows.

EXAMPLE 122

200 Grams of 6-chloroacetylaminomethyl-2,3-dihydro-7-hydroxy-4-methyl-1H-indene-1-one, 77.9 g of hydroxylamine hydrochloride, 300 ml of pyridine and 1,800 ml of ethanol were refluxed for 3 hours. After the reaction was completed, the solvent was removed by evaporation under a reduced pressure, then to the residue thus obtained was added 2 liters of water and the mixture was stirred vigorously, cooled and crystallized. The crystals were collected by filtration, washed with water, and recrystallized from water to obtain 167 g of (2,3-dihydro-7-hydroxy-1-hydroxyimino-4-methyl-1H-indene-6-yl)-methylaminocarbonylmethylpyridinium chloride. Colorless flake-like crystals. Melting point: 279° C. (Decomposed).

EXAMPLE 123

10 Grams of (2,3-dihydro-7-hydroxy-1-hydroxyimino-4-methyl-1H-indene-6-yl)methylaminocarbonylmethylpyridinium chloride, 200 ml of acetic acid and 1.0 g of platinum oxide were subjected to catalytic hydrogenation under 3 atmospheric hydrogen gas pressure at room temperature for 8 hours. After the hydrogenation was completed, the catalyst was removed by filtration, and the filtrate was concentrated to dryness under a reduced pressure. The residue thus obtained was dissolved in 100 ml of methanol and under ice-cooled condition, a methanol solution saturated with hydrogen chloride gas was added thereto so as to adjust the pH of the solution to about pH 1, then the said solution was concentrated to dryness under a reduced pressure. The residue thus obtained was recrystallzed from ethanol-diethyl ether to obtain 4.8 g of 1-amino-2,3-dihydro-7-hydroxy-4-methyl-6-piperidinylacetylaminomethyl-1H-indene dihydrochloride. Colorless powdery crystals. Melting point: 146° C. (decomposed).

EXAMPLE 124

0.21 Gram of 4-(3-chlorophenyl)-1-(2,3-epoxypropyl)piperazine was added to a solution containing 0.21 g of 1-amino-2,3-dihydro-7-hydroxy-2,2,4,6-tetramethyl-1H-indene hydrochloride in 10 ml of ethanol solution, and the mixture was refluxed for 5 hours. After the reaction was completed, the reaction mixture was concentrated by removing the solvent under a reduced pressure, the residue thus obtained was alkalified with

TABLE 9

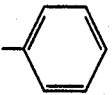

| Example No. | $R^1$ | $R^2$ | $R^3$ | $R^4$ | $R^5$ | $R^6$ | Crystal form (Recrystallization solvent) | Melting point (°C.) | Salt |
|---|---|---|---|---|---|---|---|---|---|
| 119 | H | H | $CH_3$ | $CH_3$ | $-NHC_{10}H_{21}$ | H | Colorless needle-like crystals (Acetonitrile) | 124–126 | Hydrochloride |
| 120 | 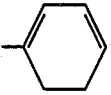 | H | $CH_3$ | $CH_3$ | $-NHCH_2CH_2-N(CH_3)(CH_3)$ | H | Colorless powdery crystals (Ethanol) | 221–223 | Dihydrochloride |
| 121 | 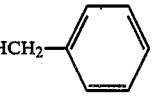 | H | $CH_3$ | $CH_3$ | $-NHCH_2-\text{phenyl}$ | H | Colorless needle-like crystals (Ethanol) | 122–123 | — |

10%-sodium bicarbonate aqueous solution, then extracted with 100 ml of methylene chloride. The extract was washed three times with 100 ml of water each time, then dried with anhydrous magnesium sulfate. The methylene chloride extract was concentrated by removing the solvent under a reduced pressure, and the residue was purified by a silica gel column chromatography (eluent: ethyl acetate:n-hexane=1:1) to obtain 0.21 g of 1-{3-[4-(3-chlorophenyl)-1-piperazinyl]-2-hydroxypropylamino}-2,3-dihydro-7-hydroxy-2,2,4,6-tetramethyl-1H-indene.

NMR (CDCl$_3$) δ:7.14 (t, 1H0, 6.90–6.70 (m, 4H), 4.60–3.70 (br., 2H), 4.20 (s, 1H), 3.90 (m, 1H), 3.20 (t, 6H), 2.90–2.30 (m, 8H), 2.18 (s, 3H), 2.80 (s, 3H), 1.20 (s, 2H), 0.85 (s, 3H).

EXAMPLE 125

2.60 Grams of 4,6-dimethyl-7-hydroxy-1-benzylamino-2-phenyl-3H-indene, 0.26 g of 10%-palladium carbon and 50 ml of acetic acid were catalytically hydrogenated under 4 atmospheric hydrogen gas pressure at room temperature. After completed the hydrogenation, the catalyst was separated from the reaction mixture and was washed with ethanol. The filtrate and the above-mentioned washing ethanol liquor were combined together and concentrated. The residue thus obtained was purified by a silica gel column chromatography (eluent: ethyl acetate:n-hexane=1:5) to obtain 0.67 g of 1-amino-2-phenyl-2-benzyloxy-4,6-dimethyl-2,3-dihydro-7-hydroxy-1H-indene (Compound A) and 0.37 g of 1-amino-2-phenyl-2-hydroxy-4,6-dimethyl-2,3-dihydro-7-hydroxy-1H-indene (Compound B) were obtained.

Compound A: Light yellow prism-like crystals (recrystallized from ethanol) Melting point: 166°–167° C.

Compound B: Colorless needle-like crystals (recrystallized from ethanol) Melting point: 151°–153° C.

EXAMPLE 126

7.04 Grams of 1-chloroacetylamino-2,3-dihydro-7-hydroxy-2,2,4,6-tetramethyl-1H-indene was dissolved in 200 ml of acetonitrile, then 10 ml of triethylamine and 5.0 g of m-methoxyphenylpiperazine were added thereto. The reaction mixture was refluxed for 2 hours. The reaction mixture was concentrated to dryness under a reduced pressure, and to the residue thus obtained was added 100 ml of water, then the pH of this solution was adjusted with an aqueous solution saturated with sodium bicarbonate to about pH=8. This solution was extracted with 500 ml of ethyl acetate, and the extract was washed with water, concentrated to dryness under a reduced pressure. The residue thus obtained was boiled with ethanol, and the ethanol-insoluble matter was collected by filtration and recrystallized from ethanol to obtain 3.9 g of 2,3-dihydro-7-hydroxy-1-[4-(3-methoxyphenyl-1-piperazinyl)]carbonylamino-2,2,4,6-tetramethyl-1H-indene. Colorless powdery crystals. Melting point: 206°–208° C.

NMR (CDCl$_3$-DMSO-d$_6$) δ: 1.10 (s, 3H), 1.23 (s, 3H), 2.10 (s, 3H), 2.15 (s, 3H), 2.46 (d, 1H, J=15 Hz), 2.92 (d, 1H, J=15 Hz), 3.05–3.30 (m, 4H), 3.50–3.65 (m, 4H), 3.76 (s, 3H), 4.46 (d, 1H, J=7.5 Hz), 6.25–6.60 (m, 3H), 6.74 (s, 1H), 7.14 (t, 1H, J=9 Hz), 7.50 (m, 1H).

The above-mentioned ethanol extract was concentrated under a reduced pressure, to the residue thus obtained was added an ethanol solution of fumaric acid to adjust the pH of the solution to about pH=4–5, then concentrated to dryness under a reduced pressure. The residue thus obtained was recrystallized from ethanol to obtain 5.2 g of 2,3-dihydro-7-hydroxy-1-[4-(3-methoxyphenyl-1-piperazinyl)]-acetylamino-2,2,4,6-tetramethyl-1H-indene fumarate. Colorless powdery crystals. Melting point: 167°–169° C.

NMR (CDCl$_3$-DMSO-d$_6$) δ: 1.13 (s, 3H), 1.26 (s, 3H), 2.10 (s, 3H), 2.18 (s, 3H), 2.48–2.92 (m, 6H), 3.10–3.34 (m, 6H), 3.78 (s, 3H), 4.68 (d, 1H, J=7.5 Hz), 6.30–6.60 (m, 3H), 6.74 (s, 2H), 6.80 (s, 1H), 7.15 (t, 1H, J=9 Hz), 8.08 (d, 1H, J=7.5 Hz), 8.70–10.0 (br., 2H).

The pharmacological activities of 2,3-dihydro-1H-indene derivatives and salts thereof represented by the general formula (1) are shown as follows.

PHARMACOLOGICAL TESTS

TEST COMPOUNDS 1. 1-[4-(3-Chlorophenyl-1-piperazinyl]acetylamino-2,3-dihydro-7-hydroxy-2,2,4,6-tetramethyl-1H-indene
2. 1-[4-(3-Methoxyphenyl)-1-piperazinyl]acetylamino-2,3-dihydro-7-hydroxy-4-methyl-6-(1-methylpropyl)-1H-indene dihydrochloride
3. 1-[4-(3,5-Dichlorophenyl)-1-piperazinyl]acetylamino-2,3-dihydro-7-hydroxy-4-methyl-6-(1-methylpropyl)1H-indene
4. 1-[4-(3-Chlorophenyl)-1-piperazinyl]acetylamino-2,3-dihydro-7-hydroxy-4-methyl-6-(1-methylpropyl)-1H-indene hydrochloride
5. 1-[4-(3-Chlorophenyl)-1-piperazinyl]acetylamino-2,3-dihydro-7-hydroxy-4,6-dimethyl-1H-indene hydrochloride
6. 1-[4-(3-Methoxyphenyl)-1-piperazinyl]acetylamino-2,3-dihydro-7-hydroxy-2,2,4,6-tetramethyl-1H-indene
7. 2,3-Dihydro-7-hydroxy-4-methyl-1-(4-methyl-1-piperazinyl)acetylamino-6-(1-methylpropyl)-1H-indene
8. 1-Amino-2-phenyl-4,6-dimethyl-7-hydroxy-2,3-dihydro-1H-indene
9. 1-Amino-2-(2-methylphenyl)-4,6-dimethyl-7-hydroxy-2,3-dihydro-1H-indene
10. 1-Amino-2-(4-chlorophenyl)-4,6-dimethyl-7-hydroxy-2,3-dihydro-1H-indene
11. 1-[4-(3-Chlorophenyl)-1-piperazinyl]acetylamino-4-methyl-6-(1-phenylpropyl)-7-hydroxy-2,3-dihydro-1H-indene
12. 1-[4-(3-Methoxyphenyl)-1-piperazinyl]acetylamino-2-cyclohexyl-4,6-dimethyl-7-hydroxy-2,3-dihydro-1H-indene
13. 1-[4-(3-Methoxyphenyl)-1-piperazinyl]amino-2,2,4,6-tetramethyl-7-hydroxy-2,3-dihydro-1H-indene
14. 1-Amino-4-methyl-6-(1-cyclohexylpropyl)-7-hydroxy-2,3-dihydro-1H-indene
15. 1-(4-Methyl-1-piperazinyl)acetylamino-2,2,4,6-tetramethyl-7-hydroxy-2,3-dihydro-1H-indene
16. 1-Amino-2-methyl-2-phenyl-4,6-dimethyl-7-methoxy-2,3-dihydro-1H-indene
17. 1-{2-[4-(3-Chlorophenyl)-1-piperazinyl]ethylamino}-2,2,4,6-tetramethyl-7-hydroxy-2,3-dihydro-1H-indene
18. 1-(2,3-Dihydro-7-hydroxy-2,2,4,6-tetramethyl-1H-indene-1-yl)aminoacetyl-4-(3-chlorophenyl)-piperazine
19. 1-(Pyrrolidinylacetylamino)-7-hydroxy-2,2,4,6-tetramethyl-2,3-dihydro-1H-indene
20. 1-(Piperidinylacetylamino)-7-hydroxy-2,2,4,6-tetramethyl-2,3-dihydro-1H-indene 21. 2,3-Dihydro-1-limino-2-phenyl-2-hydroxy-4,6-dimethyl-7-hydroxy-1H-indene
22. 2,3-Dihydro-1-[2-(dimethylamino)ethylamino]-2-phenyl-4,6-dimethyl-7-hydroxy-1H-indene
23. 2,3-Dihydro-1-benzylamino-2-phenyl-4,6-dimethyl-7-hydroxy-1H-indene
24. 2,3-Dihydro-1-amino-2-phenyl-2-benzyloxy-4,6-dimethyl-7-hydroxy-1H-indene
25. 2,3-Dihydro-1-amino-3-phenyl-4,6-dimethyl-7-hydroxy-1H-indene
26. 2,3-Dihydro-1-[4-(3-methoxyphenyl)-1-piperazinyl]-acetylamino-2,2,4-trimethyl-7-hydroxy-1H-indene
27. 2,3-Dihydro-1-[4-(4-methoxyphenyl)-1-piperazinyl]-acetylamino-2,2,4,6-tetramethyl-7-hydroxy-1H-indene
28. 2,3-Dihydro-1-[4-(4-methoxybenzoyl)-1-piperazinyl]-acetylamino-2,2,4,6-tetramethyl-7-hydroxy-1H-indene
29. 2,3-Dihydro-1-[4-(3-methoxyphenyl)-1-piperazinyl]-acetylamino-2,2,4,6-tetramethyl-7-methoxy-1H-indene
30. 2,3-Dihydro-1-[4-(2-hydroxyethyl)-1-piperazinyl]acetylamino-2,2,4,6-tetramethyl-7-hydroxy-1H-indene
31. 2,3-Dihydro-1-[4-(2,4,6-trimethylphenyl)-1-piperazinyl]acetylamino-2,2,4,6-tetramethyl-7-hydroxy-1H-indene
32. 2,3-Dihydro-2-(2-chlorohexyl)-1-amino-4,6-dimethyl-7-hydroxy-1H-indene
33. 2,3-Dihydro-1-amino-2-phenyl-4-chloro-6-methyl-7-hydroxy-1H-indene
34. 2,3-Dihydro-1-[4-(3-chlorophenyl)-piperazinyl]acetylamino-2-(2-methylphenyl)-4,6-dimethyl-7-hydroxy-1H-indene
35. 2,3-Dihydro-1-amino-2-benzyl-4,6-dimethyl-7-hydroxy-1H-indene
36. 2,3-Dihydro-1-amino-2-(4-methoxybenzyl)-4,6-dimethyl-7-hydroxy-1H-indene
37. 2,3-Dihydro-2,2,4,6-tetramethyl-1-(4- pyrrolidinylcarbonylmethyl-1-piperazinyl)-acetylamino-7-hydroxy-1H-indene
38. 2,3-Dihydro-2,4,6-trimethyl-2-phenyl-1-[4-(3-methoxyphenyl)-1-piperazinyl]acetylamino-7-methoxy- 1H-indene
39. 2,3-Dihydro-2,2,4,6-tetramethyl-1-[4-(2-ethoxyphenyl)-1-piperazinyl]acetylamino-7-hydroxy-1H-indene
40. 2,3-Dihydro-2,2,4,6-tetramethyl-1-[4-2,5-dichlorophenyl)-1-piperazingy]acetylamino-7-hydroxy-1H-indene
41. 2,3-Dihydro-2,2,4,6-tetramethyl-1-[4-(3-fluorophenyl)-1-piperaziny]acetylamino-7-hydroxy-1H-indene
42. 2,3-Dihydro-2,2,4,6-tetramethyl-1-[4-(3,4-dimethoxyphenyl)-1-piperazinyl]acetylamino-7-hydroxy-1H-indene
43. 2,3-Dihydro-2-(4-chlorobenzyl)-1-amino-4,6-dimethyl-7-hydroxy-1H-indene
44. 2,3-Dihydro-2-(cyclohexylmethyl)-2,4,6-trimethyl-7-hydroxy-1-amino-1H-indene
45. 2,3-Dihydro-1-amino-2-phenyl-4-methyl-6-bromo-7-hydroxy-1H-indene

PHARMACOLOGICAL TEST—1

Survival Test Under Hypoxic Condition

This test was conducted by a procedure similar to that described in "Arch. Int. Pharmacodyn. Ther., Vol. 233, page 137, (1987)".

ICR-strain male mice (weighing 20 to 30 g) were used as test animals. One test group was consisting of four (4) mice. The mice were placed in a glass desiccator with which a stop valve was equipped. Inside pressure of the desiccator was reduced until 210 or 240 mm Hg by sucking the inside air by using a vacuum pump, then the stop valve was closed. Each of the test compounds was administered orally or intraperitoneally to the mouse at 15 minutes before the beginning of the vacuum pump operation.

Survival time of the test mouse was determined as the length of time between the beginning of the vacuum pump operation and the cease of breathing of the test mouse.

Activity of the test compound in the survival test was defined as the ratio (%) of survival time of the test mouse under hypoxic condition in control group (A) and that of in the test group (B) being administered with test compound, calculated from the following formula:

Ratio of survival time $(\%) = B/A \times 100$ wherein
A: survival time of the test mouse in control group
B: survival time of the test mouse being administered with test compound (test group)

The test results are shown in Table 10 below.

TABLE 10

| Test compound | Method of administration | Dosage (mg/kg) | Ratio of survival time (%) |
|---|---|---|---|
| 1 | Orally | Control | 100 |
| | | 10 | 151 |
| | | 30 | 148 |
| 2 | Intraperitoneally | Control | 100 |
| | | 3 | 112 |
| | | 10 | 218 |
| | | 30 | 158 |
| 3 | Intraperitoneally | Control | 100 |
| | | 30 | 139 |
| 4 | Orally | Control | 100 |
| | | 10 | 119 |
| | | 30 | 145 |
| | | 100 | 225 |
| 5 | Orally | Control | 100 |
| | | 100 | 211 |
| 6 | Intraperitoneally | Control | 100 |
| | | 30 | 169 |
| 7 | Orally | Control | 100 |
| | | 100 | 132 |
| 8 | Intraperitoneally | Control | 100 |
| | | 30 | 186 |
| 9 | Orally | Control | 100 |
| | | 30 | 202 |
| 13 | Intraperitoneally | Control | 100 |
| | | 10 | 138 |
| 14 | Intraperitoneally | Control | 100 |
| | | 10 | 901 |
| 17 | Orally | Control | 100 |
| | | 30 | 141 |
| 18 | Orally | Control | 100 |
| | | 30 | 147 |
| 19 | Orally | Control | 100 |
| | | 30 | 134 |
| 25 | Orally | Control | 100 |
| | | 30 | 123 |
| 32 | Orally | Control | 100 |
| | | 100 | 121 |
| 34 | Orally | Control | 100 |
| | | 100 | 123 |

TABLE 10-continued

| Test compound | Method of administration | Dosage (mg/kg) | Ratio of survival time (%) |
|---|---|---|---|
| 35 | Orally | Control | 100 |
|  |  | 100 | 156 |
| 36 | Orally | Control | 100 |
|  |  | 100 | 148 |
| 37 | Orally | Control | 100 |
|  |  | 100 | 159 |
| 39 | Orally | Control | 100 |
|  |  | 100 | 131 |
| 40 | Orally | Control | 100 |
|  |  | 100 | 151 |
| 41 | Orally | Control | 100 |
|  |  | 100 | 123 |
| 43 | Orally | Control | 100 |
|  |  | 100 | 121 |
| 45 | Orally | Control | 100 |
|  |  | 100 | 125 |

PHARMACOLOGICAL TEST—2

Test for Determining Restoration From Disturbance of Consciousness in Mouse

This test was conducted for determining that whether compounds of the present invention will show effects for restoration from disturbance of consciousness.

The head of test mouse was fixed on a pillow made of foamed polystyrene resin, by holding the cervical skin of the mouse. The centriciput of the test mouse was let shocked by falling a cylindrical rod (weighing 20 g) made of polyacrylic resin.

As to the indication of effects for restoration from disturbance of consciousness, the length of time appearing righting reflex (RR-time) after giving the shock, and the length of time appearing spontaneous motor (SM-time) after giving the shock were used.

Each of the test compounds was administered orally or intraperitoneally in the rate of 0.1 ml/kg of the body weight, at 15 minutes before giving the shock. To the test mouse of the control group, the same amount of physiological saline water was administered.

After the test, the brains of all of the tested mice were subjected to postmortem examination, and those mice showing contused wound in the brain were excluded from the determination.

The RR-time obtained from the test mouse of control group (C) is defined as 100, and the ratio (%) of the RR-time obtained from the test mouse of test group (D) to the above-mentioned (C) is calculated from the formula as follows:

Ratio of RR-time (%) = D/C × 100

Similarly, the SM-time obtained from the test mouse of control group (E) is defined as 100, and ratio (%) of the SM-time obtained from the test mouse of test group (F) to the above-mentioned (E) is calculated from the formula as follows:

Ratio of SM-time (%) = F/E × 100

The results are shown in Table 11 as follows:

TABLE 11

| Test compound | Method of administration | Dosage (mg/kg) | Ratio of RR-time (%) | Ratio of SM-time (%) |
|---|---|---|---|---|
| 4 | Orally | Control | 100 | 100 |
|  |  | 10 | 84 | 80 |
| 6 | Intraperitoneally | Control | 100 | 100 |
|  |  | 10 | 48 | 46 |
|  |  | 30 | 53 | 61 |
| 7 | Orally | Control | 100 | 100 |
|  |  | 100 | 50 | 63 |
| 8 | Orally | Control | 100 | 100 |
|  |  | 30 | 34 | 29 |
| 10 | Orally | Control | 100 | 100 |
|  |  | 30 | 53 | 37 |
| 11 | Orally | Control | 100 | 100 |
|  |  | 30 | 31 | 38 |
| 12 | Orally | Control | 100 | 100 |
|  |  | 30 | 50 | 50 |
| 13 | Orally | Control | 100 | 100 |
|  |  | 10 | 45 | 78 |
| 15 | Orally | Control | 100 | 100 |
|  |  | 30 | 45 | 41 |
| 16 | Orally | Control | 100 | 100 |
|  |  | 30 | 25 | 24 |
| 17 | Orally | Control | 100 | 100 |
|  |  | 30 | 65 | 60 |
| 19 | Orally | Control | 100 | 100 |
|  |  | 100 | 59 | 46 |
| 20 | Orally | Control | 100 | 100 |
|  |  | 10 | 75 | 67 |
| 21 | Orally | Control | 100 | 100 |
|  |  | 30 | 74.5 | 85.1 |
| 22 | Oraally | Control | 100 | 100 |
|  |  | 30 | 66.6 | 78.7 |
| 23 | Orally | Control | 100 | 100 |
|  |  | 30 | 70.5 | 68.6 |
| 24 | Orally | Control | 100 | 100 |
|  |  | 30 | 82.3 | 80.7 |
| 26 | Orally | Control | 100 | 100 |
|  |  | 30 | 63 | 65 |
| 27 | Orally | Control | 100 | 100 |
|  |  | 30 | 82 | 63 |
| 28 | Orally | Control | 100 | 100 |
|  |  | 30 | 97 | 77 |
| 29 | Orally | Control | 100 | 100 |
|  |  | 30 | 73 | 62 |
| 30 | Orally | Control | 100 | 100 |
|  |  | 30 | 94 | 96 |
| 31 | Orally | Control | 100 | 100 |
|  |  | 30 | 87 | 84 |
| 32 | Orally | Control | 100 | 100 |
|  |  | 30 | 43.6 | 49.5 |
| 33 | Orally | Control | 100 | 100 |
|  |  | 30 | 64.5 | 76.9 |
| 34 | Orally | Control | 100 | 100 |
|  |  | 30 | 75.1 | 66.0 |
| 35 | Orally | Control | 100 | 100 |
|  |  | 30 | 47.0 | 38.6 |
| 36 | Orally | Control | 100 | 100 |
|  |  | 30 | 75.3 | 62.9 |
| 37 | Orally | Control | 100 | 100 |
|  |  | 30 | 53 | 53 |
| 38 | Orally | Control | 100 | 100 |
|  |  | 30 | 75.3 | 77.0 |
| 40 | Orally | Control | 100 | 100 |
|  |  | 30 | 74 | 69 |
| 41 | Orally | Control | 100 | 100 |
|  |  | 30 | 82.8 | 72.3 |
| 42 | Orally | Control | 100 | 100 |
|  |  | 30 | 59 | 81 |
| 43 | Orally | Control | 100 | 100 |
|  |  | 30 | 66.4 | 45.9 |
| 44 | Orally | Control | 100 | 100 |
|  |  | 30 | 50.8 | 45.7 |
| 45 | Orally | Control | 100 | 100 |
|  |  | 30 | 46.7 | 33.9 |

Pharmaceutical compositions according to the present invention, containing 2,3-dihydro-1H-indene derivative or salt thereof represented by the general formula (1), as the active ingredient are illustrated by referring to the following Examples of Pharmaceutical Preparations. Present invention, however, is not restricted only to these examples.

EXAMPLE OF PHARMACEUTICAL PREPARATION—1

| Injection Preparation | |
|---|---|
| 1-{3-[4-(3-Chlorophenyl)-1-piperazinyl]-propionyl}amino-7-hydroxy-2,2,4,6-tetra-methyl-2,3-dihydro-1Hpindene | 200 mg |
| Glucose | 250 mg |
| Distilled water for injection | q.s. |
| | 5 ml |

1-{3-[4-(3-Chlorophenyl)-1-piperazinyl]propionyl}-amino-7-hydroxy-2,2,4,6-tetramethyl-2,3-dihydro-1H-indene and glucose were dissolved in distilled water for injection, then this solution was filled in an ampule of 5 ml volume. After the air in the filled ampule was replaced with nitrogen gas, then said filled ampule was sterilized with steam under the pressure at 121° C. for 15 minutes to obtain the injection preparation having the above-mentioned formulation.

EXAMPLE OF PHARMACEUTICAL PREPARATION—2

| Film Coated Tablets | |
|---|---|
| 1-(2,3-Dihydro-7-hydroxy-2,2,4,6-tetra-methyl-1H—inden-1-yl)aminoacetyl-4-(3-methoxyphenyl)piperazine | 100 g |
| Avicel (a trademark for microcrystalline cellulose, manufactured by Asahi Chemical Industry Co., Ltd.) | 40 g |
| Corn starch | 30 g |
| Magnesium stearate | 2 g |
| TC-5 (a trademark for hydroxypropyl methylcellulose, manufactured by The Shin-Etsu Chemical Co., Ltd.) | 10 g |
| Polyethylene glycol-6000 | 3 g |
| Castor oil | 40 g |
| Methanol | 40 g |
| | 265 g |

1-(2,3-Dihydro-7-hydroxy-2,2,4,6-tetramethyl-1H-indene-1-yl)aminoacetyl-4-(3-methoxyphenyl)piperazine, Avicel, corn starch and magnesium stearate were admixed together and ground, then the mixture obtained was shaped into tablets by using a tablet machine (R=10 mm). The tablets obtained were coated with a film coating consisting of TC-5, polyethylene glycol-6000, castor oil and methanol to prepare the film coated tablets having a the above-mentioned formulation.

EXAMPLE OF PHARMACEUTICAL PREPARATION—3

| Ointment Preparation | |
|---|---|
| 1-{2-[4-(3-Methoxyphenyl)-1-piperazinyl]-ethylamino}-2,3-dihydro-7-hydroxy-2,2,4,6-tetramethyl-1H—indene | 2 g |
| Purified lanoline | 5 g |
| White bees wax | 5 g |
| White petrolatum | 88 g |
| | 100 g |

White bees wax was warmed to make it a liquid state, then 1-{2-[4-(3-methoxyphenyl)-1-piperazinyl]ethylamino}-2,3-dihydro-7-hydroxy-2,2,4,6-tetramethyl-1H-indene, purified lanolin and white petrolatum were added therein. The mixture was warmed to make it in a liquid state, then stirred until solidified to prepare the ointment preparation having the above-mentioned formulation.

What is claimed is:

1. 2,3-Dihydro-1H-indene compounds and salts thereof represented by the formula (1),

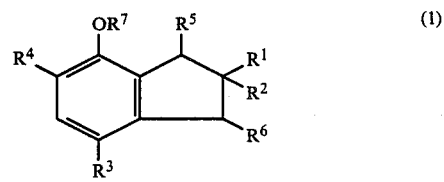

wherein
$R^1$ and $R^2$ are each a hydrogen atom, a $C_1$–$C_6$ alkyl group, an unsubstituted phenyl group, a substituted phenyl group having 1 to 3 substituents selected from the group consisting of a halogen atom and a $C_1$–$C_6$ alkyl group on the phenyl ring, an unsubstituted $C_3$–$C_8$ cycloalkyl group, a substituted $C_3$–$C_8$ cycloalkyl group having 1 to 3 halogen atoms as the substituent on the cycloalkyl ring, a $C_3$–$C_8$ cycloakyl-$C_1$–$C_6$ alkyl group, a hydroxyl group, a phenyl-$C_1$–$C_6$ alkoxy group, an unsubstituted phenyl-$C_1$–$C_6$ alkyl group, a substituted phenyl-$C_1$–$C_6$ alkyl group having 1 to 3 substituents selected from the group consisting of a halogen atom, and a $C_1$–$C_6$ alkoxy group on the phenyl ring or a substituted phenyl-$C_1$–$C_6$ alkyl group having a $C_1$–$C_4$ alkylenedioxy group on the phenyl ring;
$R^3$ is a halogen atom or a $C_1$–$C_6$ alkyl group;
$R^4$ is a hydrogen atom, a halogen atom, a phenyl-$C_1$–$C_6$ alkyl group, a $C_3$–$C_8$ cycloakyl-$C_1$–$C_6$ akyl group, a piperidinyl-$C_1$–$C_6$ alkanoylamino-$C_1$–$C_6$ alkyl group, a pyridinium-$C_2$–$C_6$ alkanoylamino-$C_1$–$C_6$ alkyl group, a $C_1$–$C_6$ alkyl group, a 1-phenyl-2 propenyl group, a 1-methyl-2-propenyl group, or a 2-chlorobenzoyl group;
$R^5$ is a hydroxyimino group, an alkylamino group having 7 to 10 carbon atoms or a group of the formula —$NHR^8$, wherein $R^8$ is a hydrogen atom, a halogen-substituted $C_1$–$C_6$ alkanoyl group, a $C_1$–$C_6$ alkylamino-$C_1$–$C_6$ alkyl group, or a phenyl-$C_1$–$C_6$ alkyl group;
$R^6$ is a hydrogen atom or a phenyl group; and
$R^7$ is a hydrogen atom or a $C_1$–$C_6$ alkyl group;
provided that, when $R^5$ is a hydroxyimino group, $R^6$ and $R^7$ are each hydrogen atoms, or when $R^5$ is a group of the formula —$NHR^8$ (wherein $R^8$ is a hydrogen atom or a halogen-substituted $C_1$–$C_6$ alkanoyl group) and $R^1$ and $R^2$ are each a hydrogen atom, or $C_1$–$C_6$ alkyl group, then $R^4$ should not be a hydrogen atom, a $C_1$–$C_6$ alkyl group or a halogen atom.

2. The 2,3-dihydro-1H-indene compounds of claim 1, wherein $R^5$ is a hydroxyimino group or an alkylamino group having 7 to 10 carbon atoms.

3. The 2,3-dihydro-1H-indene compounds of claim 1, wherein $R^5$ is a group of the formula —$NHR^8$.

4. The 2,3-dihydro-1H-indene compounds of claim 3, wherein $R^8$ is a halogen-substituted-$C_1$-$C_6$ alkanoyl group.

5. The 2,3-dihydro-1H-indene compounds of claim 3, wherein $R^8$ is a hydrogen atom.

6. The 2,3-dihydro-1H-indene compounds of claim 5, wherein $R^1$ and $R^2$ are each an unsubstituted phenyl group or a substituted phenyl group having 1 to 3 substituents selected from the group consisting of a halogen atom and a $C_1$-$C_6$ alkyl group on the phenyl ring.

7. The 2,3-dihydro-1H-indene compounds of claim 5, wherein $R^1$ and $R^2$ are each a hydrogen atom, a $C_1$-$C_6$ alkyl group, an unsubstituted $C_3$-$C_8$ cycloalkyl group, a substituted $C_3$-$C_8$ cycloalkyl group having 1 to 3 halogen atoms as the substituent on the cycloalkyl ring, a $C_3$-$C_8$ cycloakyl-$C_1$-$C_6$ alkyl group, a hydroxyl group, a phenyl-$C_1$-$C_6$ alkoxy group, an unsubstituted phenyl-$C_1$-$C_6$ alkyl group, a substituted phenyl-$C_1$-$C_6$ alkyl group having 1 to 3 substituents selected from the group consisting of a halogen atom, and a $C_1$-$C_6$ alkoxy group on the phenyl ring or a substituted phenyl-$C_1$-$C_6$ alkyl group having a $C_1$-$C_4$ akylenedioxy group on the phenyl ring.

8. The 2,3-dihydro-1H-indene compounds of claim 6 or 7, wherein $R^6$ and $R^7$ are each a hydrogen atom.

9. The 2,3-dihydro-1H-indene compounds of claim 8, wherein $R^3$ and $R^4$ are each a $C_1$-$C_6$ alkyl group.

10. 2,3-Dihydro-1-amino-2-phenyl-4,6-dimethyl-7-hydroxy-1H-indene.

11. 2,3-Dihydro-1-amino-2-(2-methylphenyl)-4,6-dimethyl-7-hydroxy-1H-indene.

12. 2,3-Dihydro-1-amino-2-(2-chlorophenyl)-4,6-dimethyl-7-hydroxy-1H-indene.

13. A pharmaceutical composition for improving anoxemic and hypoxic symptoms and syndromes acompanied therewith containing a 2,3-dihydro-1H-indene compound or salt thereof of claim 1 and a pharmaceutically acceptable carrier therefor.

14. An antioxidizing composition consisting essentially of, as the active ingredient, a 2,3-dihydro-1H-indene compound or salt thereof of claim 1.

* * * * *